US011767492B2

(12) United States Patent
Vejborg et al.

(10) Patent No.: US 11,767,492 B2
(45) Date of Patent: Sep. 26, 2023

(54) **METHODS OF TREATING FABRIC USING A *LACTOBACILLUS* HEXOSAMINIDASE**

(71) Applicant: Novozymes A/S, Bagsvaerd (DK)

(72) Inventors: Rebecca Munk Vejborg, Allerod (DK); Dorotea Raventos Segura, Rungsted (DK); Jesper Salomon, Holte (DK); Johanne M. Jensen, Brighton (AU); Rune Nygaard Monrad, Hillerod (DK); Anne Vindum Due, Bagsvaerd (DK); Martin Gudmand, Holte (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 16/759,635

(22) PCT Filed: Oct. 31, 2018

(86) PCT No.: PCT/EP2018/079853
§ 371 (c)(1),
(2) Date: Apr. 27, 2020

(87) PCT Pub. No.: WO2019/086530
PCT Pub. Date: May 9, 2019

(65) Prior Publication Data
US 2020/0308511 A1 Oct. 1, 2020

(30) Foreign Application Priority Data

Nov. 1, 2017 (EP) .................................. 17199594

(51) Int. Cl.
| | |
|---|---|
| *C11D 3/386* | (2006.01) |
| *C12N 9/24* | (2006.01) |
| *C11D 3/20* | (2006.01) |
| *C11D 11/00* | (2006.01) |
| *C11D 17/00* | (2006.01) |

(52) U.S. Cl.
CPC ........ *C11D 3/38636* (2013.01); *C11D 3/2065* (2013.01); *C11D 3/38609* (2013.01); *C11D 3/38627* (2013.01); *C11D 3/38645* (2013.01); *C11D 3/38672* (2013.01); *C11D 11/0017* (2013.01); *C11D 17/0039* (2013.01); *C12N 9/2402* (2013.01); *C12Y 302/01052* (2013.01)

(58) Field of Classification Search
None
See application file for complete search history.

(56) References Cited

U.S. PATENT DOCUMENTS 6,465,410 B1  10/2002  Bettiol

FOREIGN PATENT DOCUMENTS

| EP | 0425019 A1 | 5/1991 | |
|---|---|---|---|
| JP | 2005247981 A | 9/2005 | |
| WO | 1998/50512 A1 | 11/1998 | |
| WO | 1999/57155 A1 | 11/1999 | |
| WO | 2004/061117 A2 | 7/2004 | |
| WO | 2008/043175 A1 | 4/2008 | |
| WO | 2008/157350 A2 | 12/2008 | |
| WO | 2014/110675 A1 | 7/2014 | |
| WO | WO-2015185689 A1 * | 12/2015 | ......... C11D 3/38636 |
| WO | WO-2016176240 A1 * | 11/2016 | ......... C11D 11/0017 |
| WO | 2017/186937 A1 | 11/2017 | |
| WO | 2017/186943 A1 | 11/2017 | |
| WO | 2017/207770 A1 | 12/2017 | |
| WO | 2018/184873 A1 | 10/2018 | |

OTHER PUBLICATIONS

Claesson et al., FEMS Microbiol. Lett. 269:22-28, 2007 (Year: 2007).*
GenBank Database Accession No. AKP66020, Jul. 2015, 2 pages (Year: 2015).*
GenBank Database Accession No. KRL51886, Nov. 2015, 2 pages (Year: 2015).*
Wilson et al., J. Mol. Biol. 297:233-249, 2000 (Year: 2000).*
Yu et al., Cell Res. 25:1352-1367, 2015 (Year: 2015).*
Flemming et al., "The biofilm matrix", Nat. Rev. Microbiol. 8:623-633, 2010 (Year: 2010).*
Anonymous, 2017, EBI Accession No. A0A239SWH9.
Li et al., 2013, EBI Accession No. U2W2U5.
Sun et al., 2016, EBI Accession No. A0A0R1FZT1.
Tamarit et al., 2015, EBI Accession No. A0A0M9D3N9.

* cited by examiner

*Primary Examiner* — David Steadman
(74) *Attorney, Agent, or Firm* — Elias Lambiris

(57) ABSTRACT

The present invention relates to compositions such as cleaning compositions comprising enzymes. The invention further relates, use of compositions comprising such enzymes in cleaning processes.

20 Claims, 2 Drawing Sheets
Specification includes a Sequence Listing.

```
                                                         10         20         30         40
SEQ ID NO 3 Lactobacillus paraplantarum DSM 10667   ...NSSTLNTSQGVMLDLGRHPLDETAIKAVISAAAEQHMQYVELHLSDN
SEQ ID NO 6 Lactobacillus apinorum                  TLADTSNDTKRIGLSLDCSRTYYSPSTIKKYIDLLKKDHGTYLQLHLNDN
SEQ ID NO 9 Lactobacillus paraplantarum             ...NSSTLNTSQGVMLDLGRHPLDETAIKAVISAAAEQHMQYVELHLSDN 50                        60         70         80
SEQ ID NO 3 Lactobacillus paraplantarum DSM 10667   EHLCFQSAYLG...............NAASATVLSATTLEQLVAYANQLN
SEQ ID NO 6 Lactobacillus apinorum                  ERYGVESSTLGQTTQNATLKDGVYYNNKTHLAFLSKNQLLDVIQYGYTHG
SEQ ID NO 9 Lactobacillus paraplantarum             EHLCFQSAYLG...............NAASATVLSATTLEQLVAYANQLN 90        100        110        120
SEQ ID NO 3 Lactobacillus paraplantarum DSM 10667   IELVPDVDLPSHAGAILRQLQQTHPDIYNTVKLDDET....IDYTKPAAI
SEQ ID NO 6 Lactobacillus apinorum                  IEVIPEIDLPGHAQSIFKLLSYTSEGKKLVKELENKDGYNEMYYNKQATI
SEQ ID NO 9 Lactobacillus paraplantarum             IELVPDVDLPSHAGAILRQLQQTHPDIYNTVKLDDET....IDYTKPAAV 130        140        150        160        170
SEQ ID NO 3 Lactobacillus paraplantarum DSM 10667   SLATTLYGELDASFNNQSQHDLMLGADEVPGSASAYIE.LTTFINQVSRF
SEQ ID NO 6 Lactobacillus apinorum                  DFSKKLLSEYVGML..PSGYHIIVGADEITISDKSDQEAVVKYINAIDDY
SEQ ID NO 9 Lactobacillus paraplantarum             SLATTLYGELDASFNNQSQHDLMLGADEVSGSASAYIE.LTTFINQVSRF 180        190        200        210        220
SEQ ID NO 3 Lactobacillus paraplantarum DSM 10667   QNQHGFNTSIWNDSLLKNELTRLDSNITINYWSQSGNNTDVAIIADRYAN
SEQ ID NO 6 Lactobacillus apinorum                  VNANHLKLEMWNDSFHKAVLSKYHKDILINYWSLTGEVSSSKDRKDNIRM
SEQ ID NO 9 Lactobacillus paraplantarum             QNQNGFNTSIWNDSLLKNELNRLDSNITINYWSQSGNNTDAAIIADRYAN 230        240        250        260        270
SEQ ID NO 3 Lactobacillus paraplantarum DSM 10667   RVSVPDILASGHPIVNCNSYATYYQIKNIGNVNDDDYFINYLNHTFRPNI
SEQ ID NO 6 Lactobacillus apinorum                  RATLPELNKAGFKTINYNSYYLYMITDPTSFTNESKKIWTSEFKKWKMNM
SEQ ID NO 9 Lactobacillus paraplantarum             RASVPDILASGHPIVNCNSYATYYQFKNIGNVNDDNYFINYLNHTFRPNI 280        290        300        310        320
SEQ ID NO 3 Lactobacillus paraplantarum DSM 10667   FNEIDTNGHNQDWTIEDGVTTNGILVSLWGADSEHVTPTAIVN....FIK
SEQ ID NO 6 Lactobacillus apinorum                  WNDESTKD.....ITKSANNIGAAISIWGEYPNQVTGDQTYNKTYYYVD
SEQ ID NO 9 Lactobacillus paraplantarum             FNEIDTNGHNQDWTIEDGVTTNGILVSLWGADSEHVTPTAIVN....FIK 330
SEQ ID NO 3 Lactobacillus paraplantarum DSM 10667   RMTIPRSF...
SEQ ID NO 6 Lactobacillus apinorum                  TFLKAQDKFTK
SEQ ID NO 9 Lactobacillus paraplantarum             RMAIPRSF...
```

Figure 2

METHODS OF TREATING FABRIC USING A *LACTOBACILLUS* HEXOSAMINIDASE

CROSS-REFERENCE TO RELATED APPLICATIONS

This application is a 35 U.S.C. 371 national application of international application no. PCT/EP2018/079853 filed Oct. 31, 2018 which claims priority or the benefit under 35 U.S.C. 119 of European application no. 17199594.7 filed Nov. 1, 2017, the contents of which are fully incorporated herein by reference.

REFERENCE TO A SEQUENCE LISTING

This application contains a Sequence Listing in computer readable form. The contents of the electronic sequence listing created on Oct. 31, 2018, named 14629-WO-PCT Seq.list 31 Oct. 2018 and 53,010 bytes in size, is hereby incorporated by reference in its entirety. An amended electronic sequence listing created on Jul. 27, 2021, named 14629-US-PCT ST25 20210727 and 56,000 bytes in size, is also hereby incorporated by reference in its entirety.

BACKGROUND OF THE INVENTION

The present invention relates to compositions such as cleaning compositions comprising enzymes having hexosaminidase activity such as dispersins obtained from *Lactobacillus* or *Streptococcus*. The invention further relates to methods and use of compositions comprising such enzymes in cleaning processes e.g. for stain removal.

DESCRIPTION OF THE RELATED ART

Enzymes have been used in detergents for decades. Usually a cocktail of various enzymes is added to detergent compositions. The enzyme cocktail often comprises various enzymes, wherein each enzyme targets a specific substrate e.g. amylases are active towards starch stains, proteases on protein stains and so forth. Textiles surface and hard surfaces, such as dishes or the inner space of a laundry machine enduring a number of wash cycles, become soiled with many different types of soiling which may compose of proteins, grease, starch etc. One type of stain may compose of organic matter, such as cell debris, biofilm, EPS, etc. Polypeptides having hexosaminidase activity include Dispersins such as Dispersin B (DspB), which are described as β-N-acetylglucosaminidases belonging to the Glycoside Hydrolase 20 family. WO04061117 A2 (Kane Biotech INC) describe use of compositions comprising DspB for reducing and preventing biofilm caused by poly-N-acetylglucosamine-producing bacteria and Kane et al. describes the use of compositions comprising dispersins for reducing biofilm on medical devises and for wound care. The application WO9850512 (Procter and Gamble) disclose laundry or cleaning products comprising one or more hexosaminidase enzymes. The present invention provides suitable enzymes for use in detergents and for deep cleaning of items during laundry and cleaning process.

SUMMARY OF THE INVENTION

A first aspect of the invention relates to a composition comprising a *Lactobacillus* or *Streptococcus* hexosaminidase, wherein the composition further comprises;

(a)
i. one or more polyol(s), preferably selected from glycerol, (mono, di, or tri) propylene glycol, ethylene glycol, polyethylene glycol, sugar alcohols, sorbitol, mannitol, erythritol, dulcitol, inositol, xylitol and adonitol,
ii. optionally one or more enzyme, preferably selected from proteases, amylases or lipases,
iii. optionally one or more surfactant, preferably selected from anionic and nonionic surfactants,
iv. optionally one or more polymer;
or
(b) a granule comprising
i. a core comprising a *Lactobacillus* or *Streptococcus* hexosaminidase and optionally,
ii. a coating consisting of one or more layer(s) surrounding the core.

The hexosaminidase preferably has N-acetylglucosaminidase activity, preferably β-1,6 N-acetylglucosaminidase activity The present invention relates to a cleaning composition comprising at least 0.01 mg *Lactobacillus* hexosaminidase and a cleaning component, wherein the cleaning component is
(a) at least one surfactant;
(b) at least one builder; or
(c) at least one polymer.

The invention further relates to the use of a composition according to the invention for cleaning of an item, wherein the item is a textile or a surface.

The invention further relates to the use of a composition according to the invention, preferably a cleaning composition such as a detergent composition comprising a *Lactobacillus* hexosaminidase,
a) for preventing, reducing or removing stickiness of the item;
b) for pretreating stains on the item;
c) for preventing, reducing or removing redeposition of soil during a wash cycle;
d) for preventing, reducing or removing adherence of soil to the item;
e) for maintaining or improving whiteness of the item;
f) for preventing, reducing or removing malodor from the item, wherein the item is a textile.

The invention further relates to a method of formulating a cleaning composition comprising adding a *Lactobacillus hexosaminidase* and at least one cleaning component.

The invention relates to a kit intended for cleaning, wherein the kit comprises a solution of an enzyme mixture comprising *Lactobacillus* hexosaminidase, and an additional enzyme selected from proteases, amylases, cellulases and lipases.

The invention further relates to a method of treating a fabric comprising;
(a) contacting the fabric with an aqueous solution of *Lactobacillus* hexosaminidase;
(b) and optionally rinsing and drying the textile.

The invention relates to a method for cleaning or laundering an item comprising the steps of:
(a) exposing an item to a wash liquor comprising a *Lactobacillus hexosaminidase* of the invention or a detergent composition comprising a *Lactobacillus* hexosaminidase;
(b) completing at least one wash cycle; and
(c) optionally rinsing the item, wherein the item is a fabric.

BRIEF DESCRIPTION OF THE FIGURES

FIG. 2 An alignment of the *Lactobacillus* polypeptides of the invention.

OVERVIEW OF SEQUENCES OF THE *LACTOBACILLUS* CLADE

Figure 1:
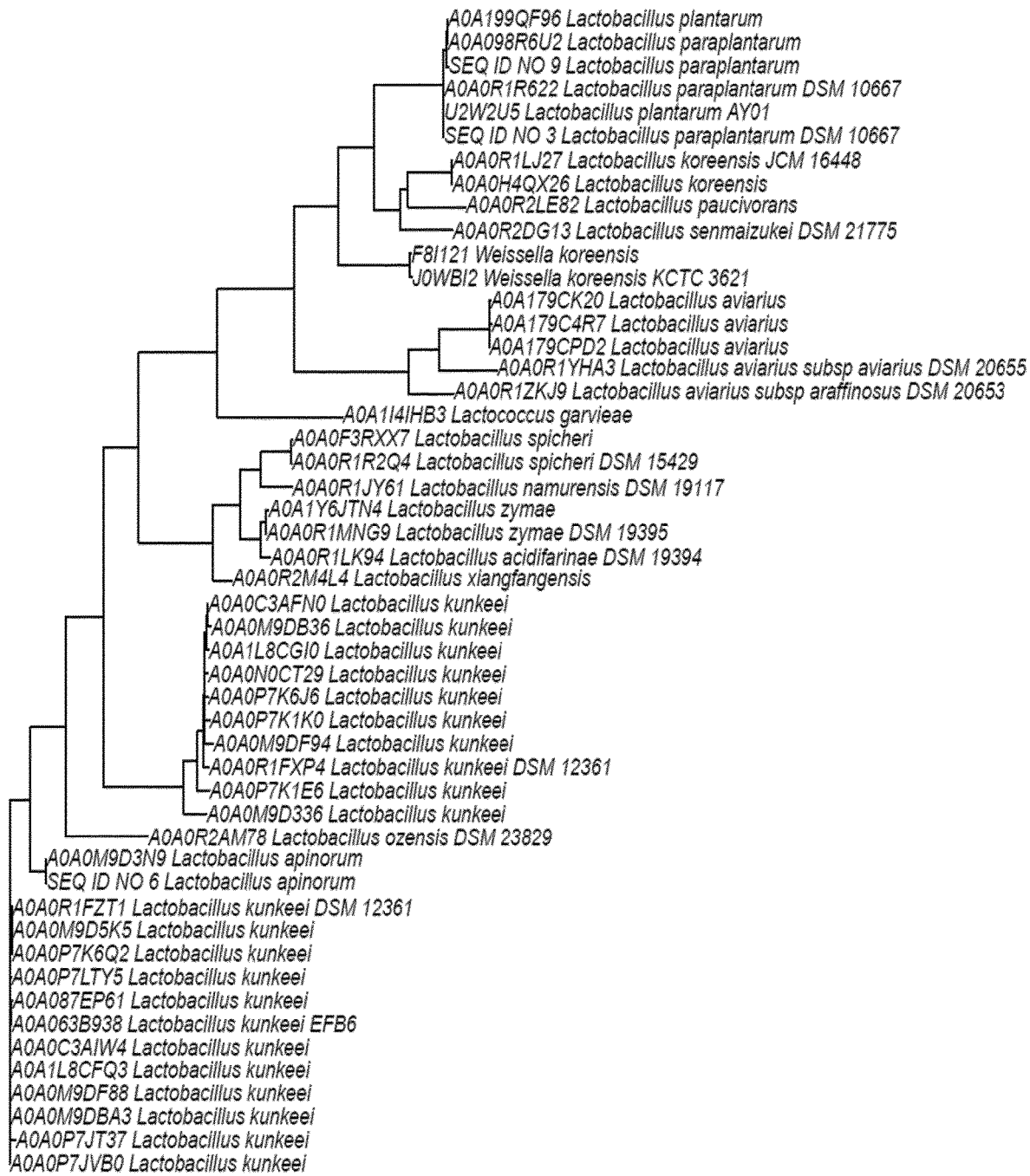
FIG. 1. In one aspect the polypeptides of the invention e.g. all belong to the *Lactobacillus* clade, which is illustrated as a phylogenetic tree in FIG. 1. The *Lactobacillus* clade or clade of *Lactobacillus* is a group of enzymes all related to the same ancestor and share common properties of taxonomic order *Lactobacillales*. Polypeptides forming a group within the clade (a subclade) of the phylogenetic tree can also share common properties and are more closely related than other polypeptides in the clade.

SEQ ID NO 1 is the DNA encoding the full-length polypeptide from *Lactobacillus paraplantarum* DSM 10667

SEQ ID NO 2 is the polypeptide derived from SEQ ID NO 1

SEQ ID NO 3 is the mature polypeptide of SEQ ID NO 2

SEQ ID NO 4 is the DNA encoding the full-length polypeptide from *Lactobacillus apinorum*

SEQ ID NO 5 is the polypeptide derived from SEQ ID NO 4

SEQ ID NO 6 is the mature polypeptide of SEQ ID NO 5

SEQ ID NO 7 is the DNA encoding the full-length polypeptide from *Lactobacillus paraplantarum*

SEQ ID NO 8 is the polypeptide derived from SEQ ID NO 7

SEQ ID NO 9 is the mature polypeptide of SEQ ID NO 8

SEQ ID NO 10 is the *Bacillus clausii* secretion signal

SEQ ID NO 11 is a His-tag sequence

SEQ ID NO 12 is the polypeptide motif GXDE

SEQ ID NO 13 is the polypeptide motif [EQ][NRSHA][YVFL][AGSTC][IVLF][EAQYN][SN]0

SEQ ID NO 14 is the polypeptide motif [VLIM][LIV]G[GAV]DE[V][PSA]

SEQ ID NO 15 is the polypeptide motif [GK]A[IL][IL][KSR][LQ]L

SEQ ID NO 16 is the DNA encoding the full-length polypeptide from *Streptococcus merionis*

SEQ ID NO 17 is the polypeptide derived from SEQ ID NO 16

SEQ ID NO 18 is the mature polypeptide of SEQ ID NO 17.

DETAILED DESCRIPTION OF THE INVENTION

Various enzymes are applied in cleaning processes each targeting specific types of soiling such as protein, starch and grease soiling. Enzymes are standard ingredients in detergents for laundry and dish wash. The effectiveness of these commercial enzymes provides detergents which removes much of the soiling. However, organic stains such as EPS (extracellular polymeric substance) comprised in much biofilm constitute a challenging type of soiling due to the complex nature of such organic matters. EPS is mostly composed of polysaccharides (exopolysaccharides) e.g. PNAG (poly-N-acetylglucosamine) and proteins, but include other macro-molecules such as eDNA, lipids and other organic substances. Organic stains, like biofilm or components hereof, such as PNAG may be sticky or glueing, which when present on textile, may give rise to redeposition or backstaining of soil resulting in a greying of the textile. Further, when dirty laundry items are washed together with less dirty laundry items the dirt present in the wash liquor tend to stick to organic stains e.g. biofilm or biofilm components as a result, hereof the laundry item is more "soiled" after wash than before wash. This effect may also be termed re-deposition. Another drawback of organic stains is the malodor as various malodor related molecules are often associated with organic stains such as biofilm.

The present invention relates to polypeptides, the use, methods and compositions comprising hexosaminidases preferably obtained from the taxonomic order of *Lactobacillales*, preferably from the genus *Lactobacillus*. The terms "*Lactobacillus* hexosaminidase" and "hexosaminidase obtained from *Lactobacillus*" may be used interchangeably throughout. The present invention further relates to polypeptides the use, methods and compositions comprising hexosaminidases obtained from the taxonomic order of *Streptococcus*. The terms "*Streptococcus* hexosaminidase" and "hexosaminidase obtained from *Streptococcus*" may be used interchangeably throughout.

The hexosaminidases are preferably dispersins and comprises N-acetylglucosaminidase and/or β-1,6-N-acetylglucosamininidase activity.

Polypeptides Having Hexosaminidase Activity

Hexosaminidase: The term "hexosaminidases" means a polypeptide having hexosaminidase activity (hexosaminidases), and includes EC 3.2.1. e.g. that catalyzes the hydrolysis of N-acetyl-D-hexosamine or N-acetyl-glucosamine polymers found e.g. in biofilm. The term includes dispersins and includes polypeptides having N-acetylglucosaminidase activity and β-1,6 N-acetylglucosaminidase activity. The term "polypeptide having hexosaminidase activity" may be used interchangeably with the term hexosaminidases and similar the term "polypeptide having beta-1,6-N-acetylglucosaminidase activity" may be used interchangeably with the term beta-1,6-N-acetylglucosamininidases. For the purposes of the present invention, hexosaminidase activity may be determined according to the procedure described in Assay I or as described in Example 11.

Dispersin: The term "dispersin" and the abbreviations "Dsp" or "Disp" means a polypeptide having hexosaminidase activity, EC 3.2.1.—that catalyzes the hydrolysis of β-1,6-glycosidic linkages of N-acetyl-glucosamine polymers (poly-N-acetylglucosamine, PNAG) found e.g. in biofilm. Thus, dispersins is an enzyme having beta-1,6 N-acetylglucosaminidase activity.

In a preferred aspect, the polypeptide of the invention is comprised in a specific clade of hexosaminidases. This clade is in the present context termed *Lactobacillus* as the hexosaminidases from the clade are obtained from bacteria within the taxonomic order of *Lactobacillales*, preferably from the *Lactobacillus* genus. The term *Lactobacillus* hexosaminidase means hexosaminidases obtained from the taxonomic order of *Lactobacillales*, preferably from the *Lactobacillus* genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly. The phylogenetic tree of the *Lactobacillus* clade is shown in FIG. 1. The polypeptides of the invention are preferably obtained from *Lactobacillus paraplantarum* or *Lactobacillus apinorum*.

In another aspect, one polypeptide of the invention is obtained from *Streptococcus,* preferably *Streptococcus*

*merionis*. The term *Streptococcus* hexosaminidase means hexosaminidases obtained from *Streptococcus* genus.

The polypeptides e.g. those comprised in the *Lactobacillus* clade, finds use in cleaning processes and compositions of the invention are listed in the table below. The hexosaminidases of Table 1 have beta-1,6-N-acetylglucosaminidase activity and are thus dispersins. The dispersins of this group have been found to be particularly useful in cleaning of organic stains e.g. PNAG from textiles. In particular, dispersins of Table 1 may be formulated in compositions e.g. cleaning compositions, comprising a dispersin obtained from *Lactobacillus* and a detergent adjunct. The polypeptides and compositions of the invention are useful in cleaning processes such as laundry and/or are useful for reduction, removal or preventing biofilm and/or for removing PNAG stains e.g. from textiles and hard surfaces.

TABLE 1

Hexosaminidase polypeptides having beta-1,6 N-acetylglucosaminidase activity comprised in the *Lactobacillus* clade

| | |
|---|---|
| SEQ ID NO 3 | *Lactobacillus paraplantarum* DSM 10667 |
| SEQ ID NO 6 | *Lactobacillus apinorum* |
| SEQ ID NO 9 | *Lactobacillus paraplantarum* |
| UniProtKB/TrEMBL | Additional dispersins |
| J0WBI2 | *Weissella koreensis* KCTC 3621 |
| A0A0P7K1K0 | *Lactobacillus kunkeei* |
| A0A0P7K6J6 | *Lactobacillus kunkeei* |
| U2W2U5 | *Lactobacillus plantarum* AY01 |
| A0A1L8CGI0 | *Lactobacillus kunkeei* |
| A0A0P7K6Q2 | *Lactobacillus kunkeei* |
| A0A098R6U2 | *Lactobacillus paraplantarum* |
| A0A0P7LTY5 | *Lactobacillus kunkeei* |
| A0A0M9D336 | *Lactobacillus kunkeei* |
| A0A0R1JY61 | *Lactobacillus namurensis* DSM 19117 |
| A0A0C3AIW4 | *Lactobacillus kunkeei* |
| A0A0M9DBA3 | *Lactobacillus kunkeei* |
| A0A0N0CT29 | *Lactobacillus kunkeei* |
| A0A0M9D5K5 | *Lactobacillus kunkeei* |
| A0A0R2DG13 | *Lactobacillus senmaizukei* DSM 21775 |
| A0A0R1R2Q4 | *Lactobacillus spicheri* DSM 15429 |
| A0A0C3AFN0 | *Lactobacillus kunkeei* |
| A0A0P7K1E6 | *Lactobacillus kunkeei* |
| A0A0M9D3N9 | *Lactobacillus apinorum* |
| A0A0R1LK94 | *Lactobacillus acidifarinae* DSM 19394 |
| A0A0H4QX26 | *Lactobacillus koreensis* |
| A0A0R1FXP4 | *Lactobacillus kunkeei* DSM 12361 |
| A0A179CPD2 | *Lactobacillus aviarius* |
| A0A063B938 | *Lactobacillus kunkeei* EFB6 |
| F8I121 | *Weissella koreensis* |
| A0A0R1LJ27 | *Lactobacillus koreensis* JCM 16448 |
| A0A1I4IHB3 | *Lactococcus garvieae* |
| A0A0P7JVB0 | *Lactobacillus kunkeei* |
| A0A1L8CFQ3 | *Lactobacillus kunkeei* |
| A0A0R1FZT1 | *Lactobacillus kunkeei* DSM 12361 |
| A0A179CK20 | *Lactobacillus aviarius* |
| A0A0F3RXX7 | *Lactobacillus spicheri* |
| A0A0R2M4L4 | *Lactobacillus xiangfangensis* |
| A0A0R1MNG9 | *Lactobacillus zymae* DSM 19395 |
| A0A0M9DB36 | *Lactobacillus kunkeei* |
| A0A0R1ZKJ9 | *Lactobacillus aviarius* subsp. *araffinosus* DSM 20653 |
| A0A0P7JT37 | *Lactobacillus kunkeei* |
| A0A0R2LE82 | *Lactobacillus paucivorans* |
| A0A087EP61 | *Lactobacillus kunkeei* |
| A0A0M9DF88 | *Lactobacillus kunkeei* |
| A0A0R2AM78 | *Lactobacillus ozensis* DSM 23829 |
| A0A199QF96 | *Lactobacillus plantarum* |
| A0A0M9DF94 | *Lactobacillus kunkeei* |
| A0A179C4R7 | *Lactobacillus aviarius* |
| A0A0R1R622 | *Lactobacillus paraplantarum* DSM 10667 |
| A0A1Y6JTN4 | *Lactobacillus zymae* |
| A0A0R1YHA3 | *Lactobacillus aviarius* subsp. *aviarius* DSM 20655 |

The hexosaminidases of the invention may be divided into clades or domain groups characterized by their motifs. One aspect of the invention relates to hexosaminidases e.g. dispersin comprised in the FQS clade. This clade has not been described previously. The clade is termed FQS and polypeptides of this domain comprises Glyco_hydro_20 domain polypeptides of bacterial origin and are in addition to having PNAG activity, characterized by comprising certain motifs. The polypeptides of the clade comprise the motif: [EQ][NRSHA][YVFL][AGSTC][IVLF][EAQYN][SN] (SEQ ID NO 13), corresponding to EHLCFQS at position 48 to 54 of SEQ ID NO 3.

One aspect of the invention relates to hexosaminidases e.g. dispersins comprised in the GADE clade. This clade has not been described previously. The polypeptides of this clade comprise Glyco_hydro_20 domain polypeptides of bacterial origin and are in addition to having PNAG activity, characterized by comprising certain motifs. The polypeptides of the clade comprise the motif example [VLIM][LIV]G[GAV]DE[VI][PSA] (SEQ ID NO 14), corresponding to pos 151 to 158 of SEQ ID NO 3, where G and DE (corresponding to positions 153 and 155-156 of SEQ ID NO 3) are fully conserved in GADE clade and part of the active site. Residues D and E are the key catalytic residues of Glyco_hydro_20 enzymes (position 155 to 156 in SEQ ID NO 3).

One aspect of the invention relates to hexosaminidases e.g. dispersins comprised in the GAIL clade This clade has not been described previously. The polypeptides of this clade comprise Glyco_hydro_20 domain polypeptides of bacterial origin and are in addition to having PNAG activity, characterized by comprising certain motifs. The polypeptides of the clade comprise the motif [GK]A[IL][IL][KSR][LQ]L (SEQ ID NO 15), corresponding to pos 96 to 102 of SEQ ID NO 3, where A and L (corresponding to positions 97 and 102 of SEQ ID NO 3) are fully conserved in GAIL clade and part of the active site.

In one aspect of the invention the hexosaminidase e.g. dispersins comprises one or more of the following motifs GXDE (SEQ ID NO 12), [EQ][NRSHA][YVFL][AGSTC][IVLF][EAQYN][SN] (SEQ ID NO 13), [VLIM][LIV]G[GAV]DE[VI][PSA] (SEQ ID NO 14), or [GK]A[IL][IL][KSR][LQ]L (SEQ ID NO 15). In one aspect, the hexosaminidases comprises the motif GXDE. In one aspect, the hexosaminidases comprises the motif [EQ][NRSHA][YVFL][AGSTC][IVLF][EAQYN][SN]. In one aspect, the hexosaminidases comprises the motif [VLIM][LIV]G[GAV]DE[VI][PSA]. In one aspect, the hexosaminidases comprises the motif [GK]A[IL][IL][KSR][LQ]L.

In one aspect, the hexosaminidase comprises all four motifs GXDE (SEQ ID NO 12), [EQ][NRSHA][YVFL][AGSTC][IVLF][EAQYN][SN] (SEQ ID NO 13), [VLIM][LIV]G[GAV]DE[VI][PSA] (SEQ ID NO 14), or [GK]A[IL][IL][KSR][LQ]L (SEQ ID NO 15).

In one aspect, the hexosaminidase comprises the two motifs GXDE (SEQ ID NO 12) and [EQ][NRSHA][YVFL][AGSTC][IVLF][EAQYN][SN] (SEQ ID NO 13).

In one aspect, the hexosaminidase comprises to three motifs GXDE (SEQ ID NO 12), [EQ][NRSHA][YVFL][AGSTC][IVLF][EAQYN][SN] (SEQ ID NO 13) and [VLIM][LIV]G[GAV]DE[VI][PSA] (SEQ ID NO 14). In one aspect, the hexosaminidase comprises the three motifs GXDE (SEQ ID NO 12), [EQ][NRSHA][YVFL][AGSTC][IVLF][EAQYN][SN] (SEQ ID NO 13) and [GK]A[IL][IL][KSR][LQ]L (SEQ ID NO 15).

An alignment of the polypeptides of the invention is shown in FIG. 2. A phylogenetic tree of the polypeptides of the invention is shown in FIG. 1.

A polypeptide of the present invention preferably has a sequence identity to the mature polypeptide sequence shown in SEQ ID NO: 3 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, wherein the polypeptide has hexosaminidase, preferably beta-1,6 N-acetylglucosaminidase activity. In one aspect, the polypeptide differs by up to 10 amino acids, e.g., 1, 2, 3, 4, 5, 6, 7, 8, 9, or 10, from the polypeptide shown in SEQ ID NO: 3.

A polypeptide of the present invention preferably has a sequence identity to the mature polypeptide sequence shown in SEQ ID NO: 6 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, wherein the polypeptide has hexosaminidase, preferably beta-1,6 N-acetylglucosaminidase activity. In one aspect, the polypeptide differs by up to 10 amino acids, e.g., 1, 2, 3, 4, 5, 6, 7, 8, 9, or 10, from the polypeptide shown in SEQ ID NO: 6.

A polypeptide of the present invention preferably has a sequence identity to the mature polypeptide sequence shown in SEQ ID NO: 9 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, wherein the polypeptide has hexosaminidase, preferably beta-1,6 N-acetylglucosaminidase activity. In one aspect, the polypeptide differs by up to 10 amino acids, e.g., 1, 2, 3, 4, 5, 6, 7, 8, 9, or 10, from the polypeptide shown in SEQ ID NO: 9.

A polypeptide of the present invention preferably has a sequence identity to the mature polypeptide sequence shown in SEQ ID NO: 18 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, wherein the polypeptide has hexosaminidase, preferably beta-1,6 N-acetylglucosaminidase activity. In one aspect, the polypeptide differs by up to 10 amino acids, e.g., 1, 2, 3, 4, 5, 6, 7, 8, 9, or 10, from the polypeptide shown in SEQ ID NO: 18.

In an embodiment, the present invention relates to a polypeptide having a sequence identity to the mature polypeptide of SEQ ID NO: 9 of at least 98%, at least 99%, or 100%, wherein the polypeptide has hexosaminidase, preferably beta-1,6 N-acetylglucosaminidase activity. In one aspect, the polypeptides differ by up to 10 amino acids, e.g., 1, 2, 3, 4, 5, 6, 7, 8, 9, or 10, from the mature polypeptide of SEQ ID NO: 9. In an embodiment, the polypeptide has been isolated. A polypeptide of the present invention preferably comprises or consists of the amino acid sequence of SEQ ID NO: 9 or an allelic variant thereof; or is a fragment thereof having hexosaminidase, preferably beta-1,6-N-acetylglucosaminidase activity. In another aspect, the polypeptide comprises or consists of the mature polypeptide of SEQ ID NO: 8. In another aspect, the polypeptide comprises or consists of amino acids 1 to 331 of SEQ ID NO: 8. In another embodiment, the present invention relates to a polypeptide having beta-1,6 N-acetylglucosaminidase activity encoded by a polynucleotide having a sequence identity to the mature polypeptide coding sequence of SEQ ID NO: 7 of at least 98%, at least 99%, or 100%. In a further embodiment, the polypeptide has been isolated.

In an embodiment, the present invention relates to a polypeptide having a sequence identity to the mature polypeptide of SEQ ID NO: 18 of at least 60%, at least 70%, at least 75%, at least 80%, at least 85%, at least 90%, at least 95%, at least 96%, at least 97% at least 98%, at least 99%, at least 98%, at least 99%, or 100%, wherein the polypeptide has hexosaminidase, preferably beta-1,6 N-acetylglucosaminidase activity. In one aspect, the polypeptides differ by up to 10 amino acids, e.g., 1, 2, 3, 4, 5, 6, 7, 8, 9, or 10, from the mature polypeptide of SEQ ID NO: 18. In an embodiment, the polypeptide has been isolated. A polypeptide of the present invention preferably comprises or consists of the amino acid sequence of SEQ ID NO: 18 or an allelic variant thereof; or is a fragment thereof having hexosaminidase, preferably beta-1,6-N-acetylglucosaminidase activity. In another aspect, the polypeptide comprises or consists of the mature polypeptide of SEQ ID NO: 17. In another aspect, the polypeptide comprises or consists of amino acids 1 to 482 of SEQ ID NO: 17. In another embodiment, the present invention relates to a polypeptide having beta-1,6 N-acetylglucosaminidase activity encoded by a polynucleotide having a sequence identity to the mature polypeptide coding sequence of SEQ ID NO: 16 of at least 60%, at least 70%, at least 75%, at least 80%, at least 85%, at least 90%, at least 95%, at least 96%, at least 97% at least 98%, at least 99%, at least 98%, at least 99%, or 100%. In a further embodiment, the polypeptide has been isolated.

The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

$$(\text{Identical Residues} \times 100)/(\text{Length of Alignment} - \text{Total Number of Gaps in Alignment}).$$

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant molecules are tested for hexosaminidase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Compositions

The invention relates to the use, methods and detergent compositions comprising *Lactobacillus* hexosaminidases, preferably dispersins.

Liquid Formulations

In one aspect the cleaning composition is a liquid composition. The hexosaminidase of the invention may be formulated as a liquid enzyme formulation, which is generally a pourable composition, though it may also have a high viscosity. The physical appearance and properties of a liquid enzyme formulation may vary a lot—for example, they may have different viscosities (gel to water-like), be colored, not colored, clear, hazy, and even with solid particles like in slurries and suspensions. The minimum ingredients are the enzyme(s) and a solvent system to make it a liquid.

The solvent system may comprise water, polyols (such as glycerol, (mono, di, or tri) propylene glycol, sugar alcohol (e.g. sorbitol), polypropylene glycol, and/or polyethylene glycol), ethanol, sugars, and salts. Usually the solvent system also includes a preservation agent and/or other stabilizers.

A liquid enzyme formulation may be prepared by mixing a solvent system and an enzyme concentrate with a desired degree of purity (or enzyme particles to obtain a slurry/suspension).

In an embodiment, the liquid enzyme composition comprises
(a) at least 0.01% w/w active enzyme protein,
(b) at least 0.5% w/w polyol,
(c) water, and
(d) optionally a preservation agent.

The hexosaminidases e.g. dispersins in the liquid composition of the invention may be stabilized using conventional stabilizing agents, e.g. a polyol such as propylene glycol or glycerol, ethylene glycol, polyethylene glycol, sugar alcohols, sorbitol, mannitol, erythritol, dulcitol, inositol, xylitol and adonitol.

One embodiment of the invention relates to a composition comprising a *Lactobacillus* hexosaminidase, wherein the composition further comprises;
(a)
 i. one or more polyol(s), preferably selected from glycerol, (mono, di, or tri) propylene glycol, ethylene glycol, polyethylene glycol, sugar alcohols, sorbitol, mannitol, erythritol, dulcitol, inositol, xylitol and adonitol,
 ii. optionally one or more enzyme, preferably selected from proteases, amylases or lipases,
 iii. optionally one or more surfactant, preferably selected from anionic and nonionic surfactants, or
 iv. optionally one or more polymer.

Another preferred embodiment relates to a composition comprising a *Lactobacillus* hexosaminidase, wherein the composition further comprises;
(a)
 i. one or more polyol(s), preferably selected from glycerol, (mono, di, or tri) propylene glycol, ethylene glycol, polyethylene glycol, sugar alcohols, sorbitol, mannitol, erythritol, dulcitol, inositol, xylitol and adonitol,
 ii. optionally one or more enzyme, preferably selected from proteases, amylases or lipases,
 iii. optionally one or more surfactant, preferably selected from anionic and nonionic surfactants, or
 iv. optionally one or more polymer; wherein the hexosaminidase has N-acetylglucosaminidase activity, preferably β-1,6 N-acetylglucosaminidase activity.

One preferred aspect relates to a composition comprising a dispersin, selected from the group consisting of polypeptides shown in SEQ ID NO 3, SEQ ID NO 6, SEQ ID NO 9, SEQ ID NO 18 or polypeptides having at least 60%, at least 70%, at least 75%, at least 80%, at least 85%, at least 90%, at least 95%, at least 98% or such as at least 99% sequence identity hereto and wherein the composition further comprises;
 i. one or more polyol(s), preferably selected from glycerol, (mono, di, or tri) propylene glycol, ethylene glycol, polyethylene glycol, sugar alcohols, sorbitol, mannitol, erythritol, dulcitol, inositol, xylitol and adonitol,
 ii. optionally one or more enzyme, preferably selected from proteases, amylases or lipases,
 iii. optionally one or more surfactant, preferably selected from anionic and nonionic surfactants, or
 iv. optionally one or more polymer.

One preferred aspect relates to a composition comprising a polypeptide shown in SEQ ID NO 3 or a polypeptide having at least 60%, at least 70%, at least 75%, at least 80%, at least 85%, at least 90%, at least 95%, at least 98% or such as at least 99% sequence identity hereto, wherein the composition further comprises;
 i. one or more polyol(s), preferably selected from glycerol, (mono, di, or tri) propylene glycol, ethylene glycol, polyethylene glycol, sugar alcohols, sorbitol, mannitol, erythritol, dulcitol, inositol, xylitol and adonitol,
 ii. optionally one or more enzyme, preferably selected from proteases, amylases or lipases,
 iii. optionally one or more surfactant, preferably selected from anionic and nonionic surfactants, or
 iv. optionally one or more polymer; and
wherein the hexosaminidase has N-acetylglucosaminidase activity, preferably β-1,6 N-acetylglucosaminidase activity.

One preferred aspect relates to a composition comprising a polypeptide shown in SEQ ID NO 6 or a polypeptide having at least 60%, at least 70%, at least 75%, at least 80%, at least 85%, at least 90%, at least 95%, at least 98% or such as at least 99% sequence identity hereto, wherein the composition further comprises;
 i. one or more polyol(s), preferably selected from glycerol, (mono, di, or tri) propylene glycol, ethylene glycol, polyethylene glycol, sugar alcohols, sorbitol, mannitol, erythritol, dulcitol, inositol, xylitol and adonitol,
 ii. optionally one or more enzyme, preferably selected from proteases, amylases or lipases,
 iii. optionally one or more surfactant, preferably selected from anionic and nonionic surfactants, or
 iv. optionally one or more polymer; and
wherein the hexosaminidase has N-acetylglucosaminidase activity, preferably β-1,6 N-acetylglucosaminidase activity.

One preferred aspect relates to a composition comprising a polypeptide shown in SEQ ID NO 9 or a polypeptide having at least 60%, at least 70%, at least 75%, at least 80%, at least 85%, at least 90%, at least 95%, at least 98% or such as at least 99% sequence identity hereto, wherein the composition further comprises;
 i. one or more polyol(s), preferably selected from glycerol, (mono, di, or tri) propylene glycol, ethylene glycol, polyethylene glycol, sugar alcohols, sorbitol, mannitol, erythritol, dulcitol, inositol, xylitol and adonitol, ii. optionally one or more enzyme, preferably selected from proteases, amylases or lipases,
iii. optionally one or more surfactant, preferably selected from anionic and nonionic surfactants, or
iv. optionally one or more polymer; and wherein the hexosaminidase has N-acetylglucosaminidase activity, preferably β-1,6 N-acetylglucosaminidase activity.

One preferred aspect relates to a composition comprising a polypeptide shown in SEQ ID NO 18 or a polypeptide having at least 60%, at least 70%, at least 75%, at least 80%, at least 85%, at least 90%, at least 95%, at least 98% or such as at least 99% sequence identity hereto, wherein the composition further comprises;
  i. one or more polyol(s), preferably selected from glycerol, (mono, di, or tri) propylene glycol, ethylene glycol, polyethylene glycol, sugar alcohols, sorbitol, mannitol, erythritol, dulcitol, inositol, xylitol and adonitol,
  ii. optionally one or more enzyme, preferably selected from proteases, amylases or lipases,
  iii. optionally one or more surfactant, preferably selected from anionic and nonionic surfactants, or
  iv. optionally one or more polymer; and wherein the hexosaminidase has N-acetylglucosaminidase activity, preferably β-1,6 N-acetylglucosaminidase activity.

One preferred aspect relates to a composition comprising a *Lactobacillus* hexosaminidase selected from the group shown in Table 1, wherein the composition further comprises;
  v. one or more polyol(s), preferably selected from glycerol, (mono, di, or tri) propylene glycol, ethylene glycol, polyethylene glycol, sugar alcohols, sorbitol, mannitol, erythritol, dulcitol, inositol, xylitol and adonitol,
  vi. optionally one or more enzyme, preferably selected from proteases, amylases or lipases,
  vii. optionally one or more surfactant, preferably selected from anionic and nonionic surfactants, or
  viii. optionally one or more polymer; and wherein the hexosaminidase has N-acetylglucosaminidase activity, preferably β-1,6 N-acetylglucosaminidase activity.

Granular Formulations

Non-dusting granulates may be produced, e.g. as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

The hexosaminidase e.g. *Lactobacillus* hexosaminidase may be formulated as a granule for example as a co-granule that combines one or more enzymes or benefit agents such as MnTACN. Each enzyme will then be present in more granules securing a more uniform distribution of enzymes in the detergent. This also reduces the physical segregation of different enzymes due to different particle sizes. Methods for producing multi-enzyme co-granulate for the detergent industry is disclosed in the IP.com disclosure IPCOM000200739D.

Another example of formulation of enzymes by the use of co-granulates are disclosed in WO 2013/188331, which relates to a detergent composition comprising (a) a multi-enzyme co-granule; (b) less than 10 wt zeolite (anhydrous basis); and (c) less than 10 wt phosphate salt (anhydrous basis), wherein said enzyme co-granule comprises from 10 to 98 wt % moisture sink components and the composition additionally comprises from 20 to 80 wt % detergent moisture sink components. WO 2013/188331 also relates to a method of treating and/or cleaning a surface, preferably a fabric surface comprising the steps of (i) contacting said surface with the detergent composition as claimed and described herein in aqueous wash liquor, (ii) rinsing and/or drying the surface.

An embodiment of the invention relates to an enzyme granule/particle comprising a hexosaminidase of the invention. The granule is composed of a core, and optionally one or more coatings (outer layers) surrounding the core. Typically, the granule/particle size, measured as equivalent spherical diameter (volume based average particle size), of the granule is 20-2000 μm, particularly 50-1500 μm, 100-1500 μm or 250-1200 μm. The core may include additional materials such as fillers, fibre materials (cellulose or synthetic fibres), stabilizing agents, solubilising agents, suspension agents, viscosity regulating agents, light spheres, plasticizers, salts, lubricants and fragrances. The core may include binders, such as synthetic polymer, wax, fat, or carbohydrate. The core may comprise a salt of a multivalent cation, a reducing agent, an antioxidant, a peroxide decomposing catalyst and/or an acidic buffer component, typically as a homogenous blend. The core may consist of an inert particle with the enzyme absorbed into it, or applied onto the surface, e.g., by fluid bed coating. The core may have a diameter of 20-2000 μm, particularly 50-1500 μm, 100-1500 μm or 250-1200 μm. The core can be prepared by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation. Methods for preparing the core can be found in Handbook of Powder Technology; Particle size enlargement by C. E. Capes; Volume 1; 1980; Elsevier. The core of the enzyme granule/particle may be surrounded by at least one coating, e.g., to improve the storage stability, to reduce dust formation during handling, or for coloring the granule. The optional coating(s) may include a salt coating, or other suitable coating materials, such as polyethylene glycol (PEG), methyl hydroxy-propyl cellulose (MHPC) and polyvinyl alcohol (PVA). Examples of enzyme granules with multiple coatings are shown in WO 93/07263 and WO 97/23606.

The coating may be applied in an amount of at least 0.1% by weight of the core, e.g., at least 0.5%, 1% or 5%. The amount may be at most 100%, 70%, 50%, 40% or 30%.

The coating is preferably at least 0.1 μm thick, particularly at least 0.5 μm, at least 1 μm or at least 5 μm. In a one embodiment, the thickness of the coating is below 100 μm. In a more particular embodiment the thickness of the coating is below 60 μm. In an even more particular embodiment the total thickness of the coating is below 40 μm. The coating should encapsulate the core unit by forming a substantially continuous layer. A substantially continuous layer is to be understood as a coating having few or no holes, so that the core unit it is encapsulating/enclosing has few or none uncoated areas. The layer or coating should in preferably be homogeneous in thickness. The coating can further contain other materials as known in the art, e.g., fillers, antisticking agents, pigments, dyes, plasticizers and/or binders, such as titanium dioxide, kaolin, calcium carbonate or talc. A salt coating may comprise at least 60% by weight w/w of a salt, e.g., at least 65%, at least 70%, at least 75%, at least 80%, at least 85%, at least 90%, at least 95% or at least 99% by weight w/w. The salt may be added from a salt solution where the salt is completely dissolved or from a salt suspension wherein the fine particles is less than 50 µm, such as less than 10 µm or less than 5 µm. The salt coating may comprise a single salt or a mixture of two or more salts. The salt may be water soluble, preferably having a solubility at least 0.1 grams in 100 g of water at 20° C., preferably at least 0.5 g per 100 g water, e.g., at least 1 g per 100 g water, e.g., at least 5 g per 100 g water.

The salt may be an inorganic salt, e.g., salts of sulfate, sulfite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminium. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, lactate, formate, acetate, butyrate, propionate, benzoate, tartrate, ascorbate or gluconate. Preferably, alkali- or earth alkali metal salts of sulfate, sulfite, phosphate, phosphonate, nitrate, chloride or carbonate or salts of simple organic acids such as citrate, malonate or acetate may be used.

The salt in the coating may have a constant humidity at 20° C. above 60%, particularly above 70%, above 80% or above 85%, or it may be another hydrate form of such a salt (e.g., anhydrate). The salt coating may be as described in WO 00/01793 or WO 2006/034710.

Specific examples of suitable salts are NaCl (CH20° C.=76%), Na2CO3 (CH20° C.=92%), NaNO3 (CH20° C.=73%), Na2HPO4 (CH20° C.=95%), Na3PO4 (CH25° C.=92%), NH4CI (CH20° C.=79.5%), (NH4)2HPO4 (CH20° C.=93,0%), NH4H2PO4 (CH20° C.=93.1%), (NH4)2SO4 (CH20° C.=81.1%), KCI (CH20° C.=85%), K2HPO4 (CH20° C.=92%), KH2PO4 (CH20° C.=96.5%), KNO3 (CH20° C.=93.5%), Na2SO4 (CH20° C.=93%), K2SO4 (CH20° C.=98%), KHSO4 (CH20° C.=86%), MgSO4 (CH20° C.=90%), ZnSO4 (CH20° C.=90%) and sodium citrate (CH25° C.=86%). Other examples include NaH2PO4, (NH4)H2PO4, CuSO4, Mg(NO3)2 and magnesium acetate.

The salt may be in anhydrous form, or it may be a hydrated salt, i.e. a crystalline salt hydrate with bound water(s) of crystallization, such as described in WO 99/32595. Specific examples include anhydrous sodium sulfate (Na2SO4), anhydrous magnesium sulfate (MgSO4), magnesium sulfate heptahydrate (MgSO4.7H2O), zinc sulfate heptahydrate (ZnSO4.7H2O), sodium phosphate dibasic heptahydrate (Na2HPO4.7H2O), magnesium nitrate hexahydrate (Mg(NO3)2(6H2O)), sodium citrate dihydrate and magnesium acetate tetrahydrate. Preferably the salt is applied as a solution of the salt, e.g., using a fluid bed.

In one aspect, the present invention provides a granule, which comprises:

(a) a core comprising a *Lactobacillus* hexosaminidase, e.g dispersin according to the invention, and
(b) optionally a coating consisting of one or more layer(s) surrounding the core.

One aspect of the invention relates to a granule, which comprises:

(a) a core comprising a *Lactobacillus* hexosaminidase e.g. dispersin, wherein the *Lactobacillus* hexosaminidase is selected from the group consisting of polypeptides shown in SEQ ID NO 3, SEQ ID NO 6, SEQ ID NO 9 or polypeptides having at least 60%, at least 70%, at least 75%, at least 80%, at least 85%, at least 90%, at least 95%, at least 98% or such as at least 99% sequence identity hereto, and
(b) optionally a coating consisting of one or more layer(s) surrounding the core.

One aspect of the invention relates to a granule, which comprises:

(a) a core comprising a polypeptide, selected from the group consisting of polypeptides shown in SEQ ID NO 3, SEQ ID NO 6, SEQ ID NO 9, SEQ ID NO 18 or polypeptides having at least 60%, at least 70%, at least 75%, at least 80%, at least 85%, at least 90%, at least 95%, at least 98% or such as at least 99% sequence identity hereto, and
(b) optionally a coating consisting of one or more layer(s) surrounding the core.

One aspect of the invention relates to a granule, which comprises:

(a) a core comprising a hexosaminidase selected from the group shown in Table 1, and
(b) optionally a coating consisting of one or more layer(s) surrounding the core.

Another aspect relates to a layered granule comprising
(a) a (non-enzymatic) core;
(b) a coating surrounding the core, wherein the coating comprises *Lactobacillus* hexosaminidase e.g. dispersin; and
(c) optionally a protective salt coating surrounding the enzyme containing coating.

Another aspect relates to a layered granule comprising
(a) a (non-enzymatic) core;
(b) a coating surrounding the core, wherein the coating comprises *Lactobacillus* hexosaminidase e.g. dispersin, wherein the *Lactobacillus* hexosaminidase is selected from the group consisting of polypeptides shown in SEQ ID NO 3, SEQ ID NO 6, SEQ ID NO 9 or polypeptides having at least 60%, at least 70%, at least 75%, at least 80%, at least 85%, at least 90%, at least 95%, at least 98% or such as at least 99% sequence identity hereto; and
(c) optionally a protective salt coating surrounding the enzyme containing coating.

Another aspect relates to a layered granule comprising
(a) a (non-enzymatic) core;
(b) a coating surrounding the core, wherein the coating comprises a hexosaminidase selected from the group shown in Table 1; and
(c) optionally a protective salt coating surrounding the enzyme containing coating.

Cleaning Compositions

A composition of the invention is preferably a cleaning composition comprising a *Lactobacillus hexosaminidase* in combination with one or more additional cleaning composition components. The choice of additional components is within the skill of the artisan and includes conventional ingredients, including the exemplary non-limiting components set forth below.

One aspect of the invention relates to a composition comprising;
  a) at least 0.01 mg/mL of at least one *Lactobacillus* hexosaminidase;
  b) at least one cleaning composition component, preferably selected from surfactants, builders, bleach components, polymers, dispersing agents and additional enzymes.

One aspect of the invention relates to a composition comprising;
  a) at least 0.01 mg/mL of at least one *Lactobacillus* hexosaminidase, wherein the *Lactobacillus hexosaminidase* is selected from the group shown in Table 1.
  b) at least one cleaning composition component, preferably selected from surfactants, builders, bleach components, polymers, dispersing agents and additional enzymes.

One aspect of the invention relates to a composition comprising;
  a) at least 0.01 mg/mL of at least one *Lactobacillus hexosaminidase*, wherein the *Lactobacillus hexosaminidase* is selected from polypeptides having at least 60%, at least 70%, at least 75%, at least 80%, at least 85%, at least 90%, at least 95%, at least 96%, at least 97% at least 98%, at least 99%, at least 98%, at least 99%, or 100%sequence identity to the polypeptides shown in SEQ ID NO 3, 6 and 9;
  b) at least one cleaning composition component, preferably selected from surfactants, builders, bleach components, polymers, dispersing agents and additional enzymes.

One aspect of the invention relates to a composition comprising;
  a) at least 0.01 mg/mL of at least one hexosaminidase, wherein the hexosaminidase has at least 60%, at least 70%, at least 75%, at least 80%, at least 85%, at least 90%, at least 95%, at least 96%, at least 97% at least 98%, at least 99%, at least 98%, at least 99%, or 100% sequence identity to the polypeptides shown in SEQ ID NO 18;
  b) at least one cleaning composition component, preferably selected from surfactants, builders, bleach components, polymers, dispersing agents and additional enzymes.

The *Lactobacillus* or *Streptococcus* hexosaminidase may be included in the cleaning e.g. detergent composition of the present invention at a level of at least 0.0001 to at least 100, at least 0.001 to at least 100, at least 0.01 to at least 100, at least 0.02 to at least 100, at least 0.01 to at least 100, at least 0.1 to at least 100, at least 0.2 to at least 100, at least 0.5 to at least 100 mg/mL, preferably, the concentration of hexosaminidase enzyme in the cleaning composition e.g. detergent is in the range 0.01 to 100 mg/mL, 0.1 to 50 mg/mL or 0.01 to 10 mg/mL. Thus, the detergent composition may comprise at least 0.00008 wt %, preferably at least 0.002 wt %, 0.003 wt %, 0.004 wt %, 0.005 wt %, 0.006 wt %, 0.008 wt %, 0.01 wt %, 0.02 wt %, 0.03 wt %, 0.05 wt %, 0.1 wt %, 0.2 wt %, 0.3 wt %, 0.4 wt %, 0.6 wt %, 0.7 wt %, 0.8 wt %, 0.9 wt % or 1.0 wt % hexosaminidase, where wt % is the weight percent, which is the mass fraction multiplied by 100. Mass fraction is the ratio of one substance with mass msub to the mass of the total mixture $m_t$, ($m_{frac}=m_{sub}/m_{tot}$).

The choice of cleaning components may include, for textile care, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

Surfactants

The cleaning composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to about 60% by weight, such as about 1% to about 40%, or about 3% to about 20%, or about 3% to about 10%. The surfactant(s) is chosen based on the desired cleaning application, and may include any conventional surfactant(s) known in the art.

When included therein the detergent will usually contain from about 1% to about 40% by weight of an anionic surfactant, such as from about 5% to about 30%, including from about 5% to about 15%, or from about 15% to about 20%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

When included therein the detergent will usually contain from about 1% to about 40% by weigh of a cationic surfactant, for example from about 0.5% to about 30%, in particular from about 1% to about 20%, from about 3% to about 10%, such as from about 3% to about 5%, from about 8% to about 12% or from about 10% to about 12%. Non-limiting examples of cationic surfactants include alkyldimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, ester quats, and combinations thereof.

When included therein the detergent will usually contain from about 0.2% to about 40% by weight of a nonionic surfactant, for example from about 0.5% to about 30%, in particular from about 1% to about 20%, from about 3% to about 10%, such as from about 3% to about 5%, from about 8% to about 12%, or from about 10% to about 12%. Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof.

When included therein the detergent will usually contain from about 0.01 to about 10% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, and combinations thereof.

When included therein the detergent will usually contain from about 0.01% to about 10% by weight of a zwitterionic surfactant. Non-limiting examples of zwitterionic surfactants include betaines such as alkyldimethylbetaines, sulfobetaines, and combinations thereof.

Builders and Co-Builders

The detergent composition may contain about 0-65% by weight, such as about 5% to about 50% of a detergent builder or co-builder, or a mixture thereof. In a dish wash detergent, the level of builder is typically in the range 40-65%, particularly in the range 50-65%. The builder and/or co-builder may particularly be a chelating agent that forms water-soluble complexes with Ca and Mg. Any builder and/or co-builder known in the art for use in cleaning detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as 2,2'-iminodiethan-1-ol), triethanolamine (TEA, also known as 2,2',2"-nitrilotriethan-1-ol), and (carboxymethyl)inulin (CMI), and combinations thereof.

The detergent composition may also contain from about 0-50% by weight, such as about 5% to about 30%, of a detergent co-builder. The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra(methylenephosphonic acid) (EDTMPA), diethylenetriaminepentakis(methylenephosphonic acid) (DTMPA or DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA), N-(2-hydroxyethyl)ethylenediamine-N,N',N"-triacetic acid (HEDTA), diethanolglycine (DEG), diethylenetriamine penta(methylenephosphonic acid) (DTPMP), aminotris(methylenephosphonic acid) (ATMP), and combinations and salts thereof. Further exemplary builders and/or co-builders are described in, e.g., WO 09/102854, U.S. Pat. No. 5,977,053

Bleaching Systems

The cleaning composition may contain 0-50% by weight, such as 1-40%, such as 1-30%, such as about 1% to about 20%, of a bleaching system. Any bleaching system comprising components known in the art for use in cleaning detergents may be utilized. Suitable bleaching system components include sources of hydrogen peroxide; sources of peracids; and bleach catalysts or boosters.

Sources of Hydrogen Peroxide:

Suitable sources of hydrogen peroxide are inorganic persalts, including alkali metal salts such as sodium percarbonate and sodium perborates (usually mono- or tetrahydrate), and hydrogen peroxide—urea (1/1).

Sources of Peracids:

Peracids may be (a) incorporated directly as preformed peracids or (b) formed in situ in the wash liquor from hydrogen peroxide and a bleach activator (perhydrolysis) or (c) formed in situ in the wash liquor from hydrogen peroxide and a perhydrolase and a suitable substrate for the latter, e.g., an ester.

a) Suitable preformed peracids include, but are not limited to, peroxycarboxylic acids such as peroxybenzoic acid and its ring-substituted derivatives, peroxy-α-naphthoic acid, peroxyphthalic acid, peroxylauric acid, peroxystearic acid, ε-phthalimidoperoxycaproic acid [phthalimidoperoxyhexanoic acid (PAP)], and o-carboxybenzamidoperoxycaproic acid; aliphatic and aromatic diperoxydicarboxylic acids such as diperoxydodecanedioic acid, diperoxyazelaic acid, diperoxysebacic acid, diperoxybrassylic acid, 2-decyldiperoxybutanedioic acid, and diperoxyphthalic, -isophthalic and -terephthalic acids; perimidic acids; peroxymonosulfuric acid; peroxydisulfuric acid; peroxyphosphoric acid; peroxysilicic acid; and mixtures of said compounds. It is understood that the peracids mentioned may in some cases be best added as suitable salts, such as alkali metal salts (e.g., Oxone®) or alkaline earth-metal salts.

b) Suitable bleach activators include those belonging to the class of esters, amides, imides, nitriles or anhydrides and, where applicable, salts thereof. Suitable examples are tetraacetylethylenediamine (TAED), sodium 4-[(3,5,5-trimethylhexanoyl)oxy]benzene-1-sulfonate (ISONOBS), sodium 4-(dodecanoyloxy)benzene-1-sulfonate (LOBS), sodium 4-(decanoyloxy)benzene-1-sulfonate, 4-(decanoyloxy)benzoic acid (DOBA), sodium 4-(nonanoyloxy)benzene-1-sulfonate (NOBS), and/or those disclosed in WO98/17767. A particular family of bleach activators of interest was disclosed in EP624154 and particularly preferred in that family is acetyl triethyl citrate (ATC). ATC or a short chain triglyceride like triacetin has the advantage that they are environmentally friendly. Furthermore, acetyl triethyl citrate and triacetin have good hydrolytical stability in the product upon storage and are efficient bleach activators. Finally, ATC is multifunctional, as the citrate released in the perhydrolysis reaction may function as a builder.

Bleach Catalysts and Boosters

The bleaching system may also include a bleach catalyst or booster.

Some non-limiting examples of bleach catalysts that may be used in the compositions of the present invention include manganese oxalate, manganese acetate, manganese-collagen, cobalt-amine catalysts and manganese triazacyclononane (MnTACN) catalysts; particularly preferred are complexes of manganese with 1,4,7-trimethyl-1,4,7-triazacyclononane (Me3-TACN) or 1,2,4,7-tetramethyl-1,4,7-triazacyclononane (Me4-TACN), in particular Me3-TACN, such as the dinuclear manganese complex [(Me3-TACN)Mn(O)3Mn(Me3-TACN)](PF6)2, and [2,2',2''-nitrilotris(ethane-1,2-diylazanylylidene-KN-methanylylidene)triphenolato-k3O]manganese(III). The bleach catalysts may also be other metal compounds; such as iron or cobalt complexes.

In some embodiments, where a source of a peracid is included, an organic bleach catalyst or bleach booster may be used having one of the following formulae:

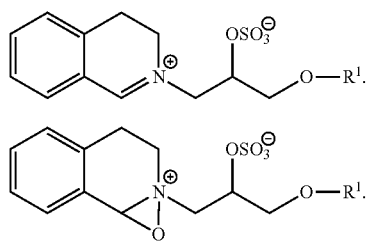

(iii) and mixtures thereof; wherein each R1 is independently a branched alkyl group containing from 9 to 24 carbons or linear alkyl group containing from 11 to 24 carbons, preferably each R1 is independently a branched alkyl group containing from 9 to 18 carbons or linear alkyl group containing from 11 to 18 carbons, more preferably each R1 is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl.

Other exemplary bleaching systems are described, e.g. in WO2007/087258, WO2007/087244, WO2007/087259, EP1867708 (Vitamin K) and WO2007/087242. Suitable photobleaches may for example be sulfonated zinc or aluminium phthalocyanines.

Metal Care Agents

Metal care agents may prevent or reduce the tarnishing, corrosion or oxidation of metals, including aluminium, stainless steel and non-ferrous metals, such as silver and copper. Suitable examples include one or more of the following:

(a) benzatriazoles, including benzotriazole or bis-benzotriazole and substituted derivatives thereof. Benzotriazole derivatives are those compounds in which the available substitution sites on the aromatic ring are partially or completely substituted. Suitable substituents include linear or branch-chain Ci-C20-alkyl groups (e.g., C1-C20-alkyl groups) and hydroxyl, thio, phenyl or halogen such as fluorine, chlorine, bromine and iodine.

(b) metal salts and complexes chosen from the group consisting of zinc, manganese, titanium, zirconium, hafnium, vanadium, cobalt, gallium and cerium salts and/or complexes, the metals being in one of the oxidation states II, III, IV, V or VI. In one aspect, suitable metal salts and/or metal complexes may be chosen from the group consisting of Mn(II) sulphate, Mn(II) citrate, Mn(II) stearate, Mn(II) acetylacetonate, K^TiF6 (e.g., K2TiF6), K^ZrF6 (e.g., K2ZrF6), CoSO4, Co(NOs)2 and Ce(NOs)3, zinc salts, for example zinc sulphate, hydrozincite or zinc acetate.;

(c) silicates, including sodium or potassium silicate, sodium disilicate, sodium metasilicate, crystalline phyllosilicate and mixtures thereof.

Further suitable organic and inorganic redox-active substances that act as silver/copper corrosion inhibitors are disclosed in WO 94/26860 and WO 94/26859. Preferably the composition of the invention comprises from 0.1 to 5% by weight of the composition of a metal care agent, preferably the metal care agent is a zinc salt.

Hydrotropes

The cleaning composition may contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Polymers

The cleaning composition may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or anti-foaming properties.

Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly(ethyleneimine), carboxymethyl inulin (CMI), and polycarboxylates such as PAA, PAA/PMA, poly-aspartic acid, and lauryl methacrylate/acrylic acid copolymers , hydrophobically modified CMC (HM-CMC) and silicones, copolymers of terephthalic acid and oligomeric glycols, copolymers of poly(ethylene terephthalate) and poly(oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Suitable examples include PVP-K15, PVP-K30, ChromaBond S-400, ChromaBond S-403E and Chromabond S-100 from Ashland Aqualon, and Sokalan® HP 165, Sokalan® HP 50 (Dispersing agent), Sokalan® HP 53 (Dispersing agent), Sokalan® HP 59 (Dispersing agent), Sokalan® HP 56 (dye transfer inhibitor), Sokalan® HP 66 K (dye transfer inhibitor) from BASF. Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated. Particularly preferred polymer is ethoxylated homopolymer Sokalan® HP 20 from BASF, which helps to prevent redeposition of soil in the wash liquor.

Fabric Hueing Agents

The cleaning composition of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO2007/087243.

Enzymes

The cleaning composition may comprise one or more additional enzymes such as one or more lipase, cutinase, an amylase, carbohydrase, cellulase, pectinase, mannanase, arabinase, galactanase, xylanase, oxidase, e.g., a laccase, and/or peroxidase.

In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Proteases

Suitable proteases for the compositions of the invention include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

Examples of subtilases are those derived from *Bacillus* such as *Bacillus lentus, Bacillus alkalophilus, Bacillus subtilis, Bacillus amyloliquefaciens, Bacillus pumilus* and *Bacillus gibsonii* described in; U.S. Pat. No. 7,262,042 and WO09/021867. *Subtilisin lentus, Subtilisin Novo, Subtilisin Carlsberg, Bacillus licheniformis, Subtilisin* BPN', *Subtilisin* 309, *Subtilisin* 147 and *Subtilisin* 168 and e.g. protease PD138 described in (WO93/18140). Other useful proteases may be those described in WO01/016285 and WO02/016547. Examples of trypsin-like proteases are trypsin (e.g. of porcine or bovine origin) and the Fusarium protease described in WO94/25583 and WO05/040372, and the chymotrypsin proteases derived from Cellumonas described in WO05/052161 and WO05/052146.

A further preferred protease is the alkaline protease from *Bacillus lentus* DSM 5483, as described for example in WO95/23221, and variants thereof which are described in WO92/21760, WO95/23221, EP1921147 and EP1921148.

Examples of metalloproteases are the neutral metalloprotease as described in WO07/044993 (Proctor & Gamble/Genencor Int.) such as those derived from *Bacillus amyloliquefaciens*.

Examples of useful proteases are the variants described in: WO89/06279, WO92/19729, WO96/034946, WO98/20115, WO98/20116, WO99/011768, WO01/44452, WO03/006602, WO04/03186, WO04/041979, WO07/006305, WO11/036263, WO11/036264, especially the variants with substitutions in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193, 198, 199, 200, 203, 206, 211, 212, 216, 218, 226, 229, 230, 239, 246, 255, 256, 268 and 269 wherein the positions correspond to the positions of the *Bacillus lentus* protease shown in SEQ ID NO 1 of WO 2016/001449. More preferred the protease variants may comprise one or more of the mutations selected from the group consisting of: S3T, V41, S9R, S9E, A15T, S24G, S24R, K27R, N42R, S55P, G59E, G59D, N60D, N60E, V66A, N74D, S85R, A96S, S97G, S97D, S97A, S97SD, S99E, S99D, S99G, S99M, S99N, S99R, S99H, S101A, V1021, V102Y, V102N, S104A, G116V, G116R, H118D, H118N, A120S, S126L, P127Q, S128A, S154D, A156E, G157D, G157P, 5158E, Y161A, R164S, Q176E, N179E, S182E, Q185N, A188P, G189E, V193M, N198D, V1991, Y203W, S206G, L211Q, L211D, N212D, N2125, M2165, A226V, K229L, Q230H, Q239R, N246K, N255W, N255D, N255E, L256E, L256D T268A and R269H. The protease variants are preferably variants of the *Bacillus lentus* protease (Savinase®) shown in SEQ ID NO 1 of WO 2016/001449, the *Bacillus amylolichenifaciens* protease (BPN') shown in SEQ ID NO 2 of WO2016/001449. The protease variants preferably have at least 80% sequence identity to SEQ ID NO 1 or SEQ ID NO 2 of WO 2016/001449.

A protease variant comprising a substitution at one or more positions corresponding to positions 171, 173, 175, 179, or 180 of SEQ ID NO: 1 of WO2004/067737, wherein said protease variant has a sequence identity of at least 75% but less than 100% to SEQ ID NO: 1 of WO2004/067737.

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Blaze®, Blaze Evity® 100T, Blaze Evity® 125T, Blaze Evity® 150T, Neutrase®, Everlase® and Esperase® (Novozymes A/S), those sold under the tradename Maxatase®, Maxacal®, Maxapem®, Purafect Ox®, Purafect OxP®, Puramax®, FN2®, FN3®, FN4®, Excellase®, Excellenz P1000™, Excellenz P1250™, Eraser®, Preferenz P100™, Purafect Prime®, Preferenz P110™, Effectenz P1000™, Purafect®™, Effectenz P1050™, Purafect Ox®™, Effectenz P2000™, Purafast®, Properase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

Enzyme Stabilizers/Inhibitors

The protease, as described above, may be stabilized using conventional stabilizing agents, e.g., a polyol such as glycerol, (mono, di, or tri) propylene glycol, sugar alcohol, polypropylene glycol, and/or polyethylene glycol, preferably polyethylene glycol or polypropylene glycol with a molecular weight in the range of 200-1000; or compounds that act by temporarily reducing the activity of proteases (reversible inhibitors).

Thus, the composition of the invention may also include a protease inhibitor/stabilizer, which is a reversible inhibitor of protease activity, e.g., serine protease activity. Preferably, the protease inhibitor is a (reversible) subtilisin protease inhibitor. In particular, the protease inhibitor may be a peptide aldehyde, boric acid, or a boronic acid; or a derivative of any of these.

The protease inhibitor may have an inhibition constant to a serine protease, Ki (mol/L) of from 1E-12 to 1E-03; more preferred from 1E-11 to 1E-04; even more preferred from 1E-10 to 1E-05; even more preferred from 1E-10 to 1E-06; and most preferred from 1E-09 to 1E-07.

Boronic Acids

The protease inhibitor may be a boronic acid or a derivative thereof; preferably, a phenylboronic acid or a derivative thereof. In an embodiment of the invention, the phenyl boronic acid derivative is of the following formula:

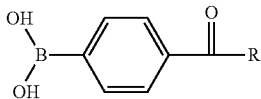

wherein R is selected from the group consisting of hydrogen, hydroxy, C1-C6 alkyl, substituted C1-C6 alkyl, C1-C6 alkenyl and substituted C1-C6 alkenyl. Preferably, R is hydrogen, CH3, CH3CH2 or CH3CH2CH2.

In a preferred embodiment, the protease inhibitor (phenyl boronic acid derivative) is 4-formyl-phenyl boronic acid (4-FPBA).

In another particular embodiment, the protease inhibitor is selected from the group consisting of thiophene-2 boronic acid, thiophene-3 boronic acid, acetamidophenyl boronic acid, benzofuran-2 boronic acid, naphtalene-1 boronic acid, naphtalene-2 boronic acid, 2-FPBA, 3-FBPA, 4-FPBA, 1-thianthrene boronic acid, 4-dibenzofuran boronic acid, 5-methylthiophene-2 boronic, acid, thionaphtrene boronic acid, furan-2 boronic acid, furan-3 boronic acid, 4,4 biphenyl-diborinic acid, 6-hydroxy-2-naphtalene, 4-(methylthio) phenyl boronic acid, 4 (trimethyl-silyl)phenyl boronic acid, 3-bromothiophene boronic acid, 4-methylthiophene boronic acid, 2-naphtyl boronic acid, 5-bromothiphene boronic acid, 5-chlorothiophene boronic acid, dimethylthiophene boronic acid, 2-bromophenyl boronic acid, 3-chlorophenyl boronic acid, 3-methoxy-2-thiophene, p-methyl-phenylethyl boronic acid, 2-thianthrene boronic acid, di-benzothiophene boronic acid, 4-carboxyphenyl boronic acid, 9-anthryl boronic acid, 3,5 dichlorophenyl boronic, acid, diphenyl boronic acidanhydride, o-chlorophenyl boronic acid, p-chlorophenyl boronic acid, m-bromophenyl boronic acid, p-bromophenyl boronic acid, p-flourophenyl boronic acid, p-tolyl boronic acid, o-tolyl boronic acid, octyl boronic acid, 1,3,5 trimethylphenyl boronic acid, 3-chloro-4-flourophenyl boronic acid, 3-aminophenyl boronic acid, 3,5-bis-(triflouromethyl) phenyl boronic acid, 2,4 dichlorophenyl boronic acid, and 4-methoxyphenyl boronic acid.

Further boronic acid derivatives suitable as protease inhibitors in the detergent composition are described in U.S. Pat. Nos. 4,963,655, 5,159,060, WO 95/12655, WO 95/29223, WO 92/19707, WO 94/04653, WO 94/04654, U.S. Pat. Nos. 5,442,100, 5,488,157 and 5,472,628.

Peptide Aldehyde or Ketone

The protease stabilizer may have the formula: P-(A)y-L-(B)x-B0-R* wherein:

R* is H (hydrogen), CH3, CX3, CHX2, or CH2X, wherein X is a halogen atom, particularly F (fluorine); preferably, R*=H (so that the stabilizer is a peptide aldehyde with the formula P-(A)y-L-(B)x-B0-H);

B0 is a single amino acid residue with L- or D-configuration of the formula —NH—CH(R)—C(=O)—;

(B)x is independently a single amino acid residue, each connected to the next B or to B0 via its C-terminal; L is absent or independently a linker group of the formula —C(=O)—, —C(=O)—C(=O)—, —C(=S)—, —C(=S)—C(=S)— or —C(=S)—C(=O)—; x is 1,2 or 3;

A is absent if L is absent or is independently a single amino acid residue connected to L via the N-terminal of the amino acid;

P is selected from the group consisting of hydrogen or if L is absent an N-terminal protection group;

y is 0, 1, or 2,

R is independently selected from the group consisting of $C_{1-6}$ alkyl, $C_{6-10}$ aryl or $C_{7-10}$ arylalkyl, optionally substituted with one or more, identical or different, substituent's R';

R' is independently selected from the group consisting of halogen, —OH, —OR", —SH, —SR", —NH2, —NHR", —NR"2, —CO2H, —CONH2, —CONHR", —CONR"2, —NHC(=N)NH2; and R" is a $C_{1-6}$ alkyl group.

x may be 1, 2 or 3 and therefore B may be 1, 2 or 3 amino acid residues respectively. Thus, B may represent B1, B2-B1 or B3-B2-B1, where B3, B2 and B1 each represent one amino acid residue. y may be 0, 1 or 2 and therefore A may be absent, or 1 or 2 amino acid residues respectively having the formula A1 or A2-A1 wherein A2 and A1 each represent one amino acid residue.

B0 may be a single amino acid residue with L- or D-configuration, which is connected to H via the C-terminal of the amino acid. B0 has the formula —NH—CH(R)—C(=O)—, wherein R is a $C_{1-6}$ alkyl, $C_{6-10}$ aryl or $C_{7-10}$ arylalkyl side chain, such as methyl, ethyl, propyl, isopropyl, butyl, isobutyl, phenyl or benzyl, and wherein R may be optionally substituted with one or more, identical or different, substituents R'. Particular examples of B0 are the D- or L-form of arginine (Arg), 3,4-dihydroxyphenylalanine, isoleucine (Ile), leucine (Leu), methionine (Met), norleucine (Nle), norvaline (Nva), phenylalanine (Phe), m-tyrosine, p-tyrosine (Tyr) and valine (Val). A particular embodiment is when B0 is leucine, methionine, phenylalanine, p-tyrosine and valine.

B1, which is connected to B0 via the C-terminal of the amino acid, may be an aliphatic, hydrophobic and/or neutral amino acid. Examples of B1 are alanine (Ala), cysteine (Cys), glycine (Gly), isoleucine (Ile), leucine (Leu), norleucine (Nle), norvaline (Nva), proline (Pro), serine (Ser), threonine (Thr) and valine (Val). Particular examples of B1 are alanine, glycine, isoleucine, leucine and valine. A particular embodiment is when B1 is alanine, glycine or valine.

If present, B2, which is connected to B1 via the C-terminal of the amino acid, may be an aliphatic, hydrophobic, neutral and/or polar amino acid. Examples of B2 are alanine (Ala), arginine (Arg), capreomycidine (Cpd), cysteine (Cys), glycine (Gly), isoleucine (Ile), leucine (Leu), norleucine (Nle), norvaline (Nva), phenylalanine (Phe), proline (Pro), serine (Ser), threonine (Thr), and valine (Val). Particular examples of B2 are alanine, arginine, capreomycidine, glycine, isoleucine, leucine, phenylalanine and valine. A particular embodiment is when B2 is arginine, glycine, leucine, phenylalanine or valine.

B3, which if present is connected to B2 via the C-terminal of the amino acid, may be a large, aliphatic, aromatic, hydrophobic and/or neutral amino acid. Examples of B3 are isoleucine (Ile), leucine (Leu), norleucine (Nle), norvaline (Nva), phenylalanine (Phe), phenylglycine, tyrosine (Tyr), tryptophan (Trp) and valine (Val). Particular examples of B3 are leucine, phenylalanine, tyrosine and tryptophan.

The linker group L may be absent or selected from the group consisting of —C(=O)—, —C(=O)—C(=O)—, —C(=S)—, —C(=S)—C(=S)— or —C(=S)—C(=O)—. Particular embodiments of the invention are when L is absent or L is a carbonyl group —C(=O)—.

A1, which if present is connected to L via the N-terminal of the amino acid, may be an aliphatic, aromatic, hydrophobic, neutral and/or polar amino acid. Examples of A1 are alanine (Ala), arginine (Arg), capreomycidine (Cpd), glycine (Gly), isoleucine (Ile), leucine (Leu), norleucine (Nle), norvaline (Nva), phenylalanine (Phe), threonine (Thr), tyrosine (Tyr), tryptophan (Trp) and valine (Val). Particular examples of A1 are alanine, arginine, glycine, leucine, phenylalanine, tyrosine, tryptophan and valine. A particular embodiment is when B2 is leucine, phenylalanine, tyrosine or tryptophan.

The A2 residue, which if present is connected to A1 via the N-terminal of the amino acid, may be a large, aliphatic, aromatic, hydrophobic and/or neutral amino acid. Examples of A2 are arginine (Arg), isoleucine (Ile), leucine (Leu), norleucine (Nle), norvaline (Nva), phenylalanine (Phe), phenylglycine, Tyrosine (Tyr), tryptophan (Trp) and valine (Val). Particular examples of A2 are phenylalanine and tyrosine.

The N-terminal protection group P (if present) may be selected from formyl, acetyl (Ac), benzoyl (Bz), trifluoroacetyl, methoxysuccinyl, aromatic and aliphatic urethane protecting groups such as fluorenylmethyloxycarbonyl (Fmoc), methoxycarbonyl (Moc), (fluoromethoxy)carbonyl, benzyloxycarbonyl (Cbz), t-butyloxycarbonyl (Boc) and adamantyloxycarbonyl; p-methoxybenzyl carbonyl, benzyl (Bn), p-methoxybenzyl (PMB), p-methoxyphenyl (PMP), methoxyacetyl, methylamino carbonyl, methylsulfonyl, ethylsulfonyl, benzylsulfonyl, methylphosphoramidyl (MeOP(OH)(=O)) and benzylphosphoramidyl (PhCH$_2$OP(OH)(=O)).

In the case of a tripeptide aldehyde with a protection group (i.e. x=2, L is absent and A is absent), P is preferably acetyl, methoxycarbonyl, benzyloxycarbonyl, methylamino carbonyl, methylsulfonyl, benzylsulfonyl and benzylphosphoramidyl. In the case of a tetrapeptide aldehyde with a protection group (i.e. x=3, L is absent and A is absent), P is preferably acetyl, methoxycarbonyl, methylsulfonyl, ethylsulfonyl and methylphosphoramidyl.

Suitable peptide aldehydes are described in WO94/04651, WO95/25791, WO98/13458, WO98/13459, WO98/13460, WO98/13461, WO98/13462, WO07/141736, WO07/145963, WO09/118375, WO10/055052 and WO11/036153. More particularly, the peptide aldehyde may be Cbz-Arg-Ala-Tyr-H, Ac-Gly-Ala-Tyr-H, Cbz-Gly-Ala-Tyr-H, Cbz-Gly-Ala-Tyr-CF$_3$, Cbz-Gly-Ala-Leu-H, Cbz-Val-Ala-Leu-H, Cbz-Val-Ala-Leu-CF$_3$, Moc-Val-Ala-Leu-CF$_3$, Cbz-Gly-Ala-Phe-H, Cbz-Gly-Ala-Phe-CF$_3$, Cbz-Gly-Ala-Val-H, Cbz-Gly-Gly-Tyr-H, Cbz-Gly-Gly-Phe-H, Cbz-Arg-Val-Tyr-H, Cbz-Leu-Val-Tyr-H, Ac-Leu-Gly-Ala-Tyr-H (SEQ ID NO: 19), Ac-Phe-Gly-Ala-Tyr-H (SEQ ID NO: 20), Ac-Tyr-Gly-Ala-Tyr-H (SEQ ID NO: 21), Ac-Phe-Gly-Ala-Leu-H (SEQ ID NO: 22), Ac-Phe-Gly-Ala-Phe-H (SEQ ID NO: 23), Ac-Phe-Gly-Val-Tyr-H (SEQ ID NO: 24), Ac-Phe-Gly-Ala-Met-H (SEQ ID NO: 25), Ac-Trp-Leu-Val-Tyr-H (SEQ ID NO: 26), MeO-CO-Val-Ala-Leu-H, MeNCO-Val-Ala-Leu-H, MeO-CO-Phe-Gly-Ala-Leu-H (SEQ ID NO: 27), MeO-CO-Phe-Gly-Ala-Phe-H (SEQ ID NO: 28), MeSO$_2$-Phe-Gly-Ala-Leu-H (SEQ ID NO: 29), MeSO$_2$-Val-Ala-Leu-H, PhCH$_2$O-P(OH)(O)-Val-Ala-Leu-H, EtSO$_2$-Phe-Gly-Ala-Leu-H (SEQ ID NO: 30), PhCH$_2$SO$_2$-Val-Ala-Leu-H, PhCH$_2$O-P(OH)(O)-Leu-Ala-Leu-H, PhCH$_2$O-P(OH)(O)-Phe-Ala-Leu-H, or MeO-P(OH)(O)-Leu-Gly-Ala-Leu-H (SEQ ID NO: 31). A preferred stabilizer for use in the liquid composition of the invention is Cbz-Gly-Ala-Tyr-H, or a hydrosulfite adduct thereof, wherein Cbz is benzyloxycarbonyl.

Further examples of such peptide aldehydes include α-MAPI, β-MAPI, Phe-C(=O)-Arg-Val-Tyr-H, Phe-C(=O)-Gly-Gly-Tyr-H, Phe-C(=O)-Gly-Ala-Phe-H, Phe-C(=O)-Gly-Ala-Tyr-H, Phe-C(=O)-Gly-Ala-L-H, Phe-C(=O)-Gly-Ala-Nva-H, Phe-C(=O)-Gly-Ala-Nle-H, Tyr-C(=O)-Arg-Val-Tyr-H, Tyr-C(=O)-Gly-Ala-Tyr-H, Phe-C(=S)-Arg-Val-Phe-H, Phe-C(=S)-Arg-Val-Tyr-H, Phe-C(=S)-Gly-Ala-Tyr-H, Antipain, GE20372A, GE20372B, Chymostatin A, Chymostatin B, and Chymostatin C.

The protease stabilizer may be a hydrosulfite adduct of the peptide aldehyde described above, e.g. as described in WO 2013/004636. The adduct may have the formula P-(A)y-L-(B)x-N(H)-CHR-CH(OH)-SO$_3$M, wherein P, A, y, L, B, x and R are defined as above, and M is H or an alkali metal, preferably Na or K.

An aqueous solution of the hydrosulfite adduct may be prepared by reacting the corresponding peptide aldehyde with an aqueous solution of sodium bisulfite (sodium hydrogen sulfite, NaHSO$_3$); potassium bisulfite (KHSO$_3$) by known methods, e.g., as described in WO 98/47523; U.S. Pat. Nos. 6,500,802; 5,436,229; J. Am. Chem. Soc. (1978) 100, 1228; Org. Synth., Coll. vol. 7: 361.

Particularly preferred peptide aldehyde protease stabilizers have the formula P—B3-B2-B1-B0-H, or a hydrosulfite adduct having the formula P—B3-B2-B1-N(H)—CHR—CHOH—SO$_3$M, wherein
i) H is hydrogen;
ii) B0 is a single amino acid residue with L- or D-configuration of the formula —NH–CH(R)—C(=O)—;
iii) B1 and B2 are independently single amino acid residues;
iv) B3 is a single amino acid residue, or is absent;
v) R is independently selected from the group consisting of C$_{1-6}$ alkyl, C$_{6-10}$ aryl or C$_{7-10}$ arylalkyl optionally substituted with one or more, identical or different, substituents R';
vi) R' is independently selected from the group consisting of halogen, —OH, —OR", —SH, —SR", —NH$_2$, —NHR", —NR"$_2$, —CO$_2$H, —CONH$_2$, —CONHR", —CONR"$_2$, —NHC(=N)NH$_2$;
vii) R" is a C$_{1-6}$ alkyl group;
viii) P is an N-terminal protection group, preferably methoxycarbonyl (Moc) or benzyloxycarbonyl (Cbz); and
ix) M is H or an alkali metal, preferably Na or K.

In an even more preferred embodiment, the peptide aldehyde protease stabilizer has the formula P—B2-B1-B0-H or an adduct having the formula P—B2-B1-N(H)—CHR—CHOH—SO$_3$M, wherein
i) H is hydrogen;
ii) B0 is a single amino acid residue with L- or D-configuration of the formula —NH—CH(R)—C(=O)—;
iii) B1 and B2 are independently single amino acid residues;

iv) R is independently selected from the group consisting of $C_{1-6}$ alkyl, $C_{6-10}$ aryl or $C_{7-10}$ arylalkyl optionally substituted with one or more, identical or different, substituents R';

v) R' is independently selected from the group consisting of halogen, —OH, —OR", —SH, —SR", —NH$_2$, —NHR", —NR"$_2$, —CO$_2$H, —CONH$_2$, —CONHR", —CONR"$_2$, —NHC(=N)NH$_2$;

vi) R" is a $C_{1-6}$ alkyl group;

vii) P is an N-terminal protection group, preferably methoxycarbonyl (Moc) or benzyloxycarbonyl (Cbz); and viii) M is H or an alkali metal, preferably Na or K.

Preferred embodiments of B0, B1, B2, B3, and P are as described above.

The molar ratio of the above-mentioned peptide aldehydes (or hydrosulfite adducts) to the protease may be at least 1:1 or 1.5:1, and it may be less than 1000:1, more preferred less than 500:1, even more preferred from 100:1 to 2:1 or from 20:1 to 2:1, or most preferred, the molar ratio is from 10:1 to 2:1.

Formate salts (e.g., sodium formate) and formic acid have also shown good effects as inhibitor of protease activity. Formate can be used synergistically with the above-mentioned protease inhibitors, as shown in WO 2013/004635. The formate salts may be present in the slurry composition in an amount of at least 0.1% w/w or 0.5% w/w, e.g., at least 1.0%, at least 1.2% or at least 1.5%. The amount is typically below 5% w/w, below 4% or below 3%.

In an embodiment, the protease is a metalloprotease and the inhibitor is a metalloprotease inhibitor, e.g., a protein hydrolysate based inhibitor (e.g., as described in WO 2008/134343).

Cellulases

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO99/001544.

Other cellulases are endo-beta-1,4-glucanase enzyme having a sequence of at least 97% identity to the amino acid sequence of position 1 to position 773 of SEQ ID NO:2 of WO 2002/099091 or a family 44 xyloglucanase, which a xyloglucanase enzyme having a sequence of at least 60% identity to positions 40-559 of SEQ ID NO: 2 of WO 2001/062903.

Commercially available cellulases include Celluzyme™, and Carezyme™ (Novozymes A/S) Carezyme Premium™ (Novozymes A/S), Celluclean™ (Novozymes A/S), Celluclean Classic™ (Novozymes A/S), Cellusoft™ (Novozymes A/S), Whitezyme™ (Novozymes A/S), Clazinase™, and Puradax HA™ (Genencor International Inc.), and KAC-500(B)™ (Kao Corporation).

Mannanases

Suitable mannanases include those of bacterial or fungal origin. Chemically or genetically modified mutants are included. The mannanase may be an alkaline mannanase of Family 5 or 26. It may be a wild-type from *Bacillus* or *Humicola*, particularly *B. agaradhaerens, B. licheniformis, B. halodurans, B. clausii*, or *H. insolens*. Suitable mannanases are described in WO1999/064619. A commercially available mannanase is Mannaway (Novozymes A/S).

Peroxidases/Oxidases

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include Guardzyme™ (Novozymes A/S).

Lipases and Cutinases:

Suitable lipases and cutinases include those of bacterial or fungal origin. Chemically modified or protein engineered mutant enzymes are included. Examples include lipase from *Thermomyces*, e.g. from *T. lanuginosus* (previously named Humicola lanuginosa) as described in EP258068 and EP305216, cutinase from Humicola, e.g. *H. insolens* (WO96/13580), lipase from strains of *Pseudomonas* (some of these now renamed to Burkholderia), e.g. *P. alcaligenes* or *P. pseudoalcaligenes* (EP218272), *P. cepacia* (EP331376), P. sp. strain SD705 (WO95/06720 & WO96/27002), *P. wisconsinensis* (WO96/12012), GDSL-type *Streptomyces* lipases (WO10/065455), cutinase from Magnaporthe grisea (WO10/107560), cutinase from *Pseudomonas mendocina* (U.S. Pat. No. 5,389,536), lipase from *Thermobifida fusca* (WO11/084412), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include Lipolase™, Lipex™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and variants of the *M. smegmatis* perhydrolase in particular the S54V variant used in the commercial product Gentle Power Bleach from Huntsman Textile Effects Pte Ltd (WO10/100028).

Amylases

Suitable amylases include alpha-amylases and/or a glucoamylases and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase derived from *B. amyloliquefaciens* shown in SEQ ID NO: 6 of WO 2006/066594 and residues 36-483 of SEQ ID NO: 4 are those having the substitutions:

M197T;
H156Y+A181T+N190F+A209V+Q264S; or
G48A+T49I+G107A+H156Y+A181T+N190F+I201F+ A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/023873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;
N128C+K178L+T182G+F202Y+Y305R+D319T+ G475K;
S125A+N128C+K178L+T182G+Y305R+G475K; or
S125A+N128C+T131I+T165I+K178L+T182G+Y305R+ G475K wherein the variants are C-terminally truncated and optionally further comprises a substitution at position 243 and/or a deletion at position 180 and/or position 181.

Further suitable amylases are amylases having SEQ ID NO: 1 of WO13184577 or variants having 90% sequence identity to SEQ ID NO: 1 thereof. Preferred variants of SEQ ID NO: 1 are those having a substitution, a deletion or an insertion in one of more of the following positions: K176, R178, G179, T180, G181, E187, N192, M199, I203, S241, R458, T459, D460, G476 and G477. More preferred variants of SEQ ID NO: 1 are those having the substitution in one of more of the following positions: K176L, E187P, N192FYH, M199L, I203YF, S241QADN, R458N, T459S, D460T, G476K and G477K and/or deletion in position R178 and/or S179 or of T180 and/or G181. Most preferred amylase variants of SEQ ID NO: 1 are those having the substitutions:

E187P+I203Y+G476K
E187P+I203Y+R458N+T459S+D460T+G476K
wherein the variants optionally further comprise a substitution at position 241 and/or a deletion at position 178 and/or position 179.

Further suitable amylases are amylases having SEQ ID NO: 1 of WO10104675 or variants having 90% sequence identity to SEQ ID NO: 1 thereof. Preferred variants of SEQ ID NO: 1 are those having a substitution, a deletion or an insertion in one of more of the following positions: N21, D97, V128 K177, R179, S180, I181, G182, M200, L204, E242, G477 and G478. More preferred variants of SEQ ID NO: 1 are those having the substitution in one of more of the following positions: N21D, D97N, V128I K177L, M200L, L204YF, E242QA, G477K and G478K and/or deletion in position R179 and/or S180 or of I181 and/or G182. Most preferred amylase variants of SEQ ID NO: 1 are those having the substitutions:

N21D+D97N+V128I
wherein the variants optionally further comprise a substitution at position 200 and/or a deletion at position 180 and/or position 181.

Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO2011/098531, WO2013/001078 and WO2013/001087.

Commercially available amylases are Duramyl™, Termamyl™, Fungamyl™, Stainzyme™, Stainzyme Plus™, Natalase™, Liquozyme X and BAN™ (from Novozymes A/S), and Rapidase™, Purastar™/Effectenz™, Powerase, Preferenz S1000, Preferenz S100 and Preferenz S110 (from Genencor International Inc./DuPont).

Peroxidases/Oxidases

Suitable peroxidases are comprised by the enzyme classification EC 1.11.1.7, as set out by the Nomenclature Committee of the International Union of Biochemistry and Molecular Biology (IUBMB), or any fragment derived therefrom, exhibiting peroxidase activity.

Suitable peroxidases include those of plant, bacterial or fungal origin. Chemically modified or protein engineered mutants are included. Examples of useful peroxidases include peroxidases from Coprinopsis, e.g., from C. cinerea (EP 179,486), and variants thereof as those described in WO 93/24618, WO 95/10602, and WO 98/15257.

A suitable peroxidase includes a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions. Preferably, the haloperoxidase is a vanadium haloperoxidase, i.e., a vanadate-containing haloperoxidase. Haloperoxidases have been isolated from many different fungi, in particular from the fungus group dematiaceous hyphomycetes, such as Caldariomyces, e.g., C. fumago, Alternaria, Curvularia, e.g., C. verruculosa and C. inaequalis, Drechslera, Ulocladium and Botrytis.

Haloperoxidases have also been isolated from bacteria such as *Pseudomonas*, e.g., *P. pyrrocinia* and *Streptomyces*, e.g., *S. aureofaciens*.

A suitable oxidase includes in particular, any laccase enzyme comprised by the enzyme classification EC 1.10.3.2, or any fragment derived therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5). Preferred laccase enzymes are enzymes of microbial origin. The enzymes may be derived from plants, bacteria or fungi (including filamentous fungi and yeasts). Suitable examples from fungi include a laccase derivable from a strain of Aspergillus, Neurospora, e.g., N. crassa, Podospora, Botrytis, Collybia, Fomes, Lentinus, Pleurotus, Trametes, e.g., T. villosa and T. versicolor, Rhizoctonia, e.g., R. solani, Coprinopsis, e.g., C. cinerea, C. comatus, C. friesii, and C. plicatilis, Psathyrella, e.g., P. condelleana, Panaeolus, e.g., P. papilionaceus, Myceliophthora, e.g., *M. thermophila*, Schytalidium, e.g., *S. thermophilum*, Polyporus, e.g., P. pinsitus, Phlebia, e.g., P. radiata (WO 92/01046), or Coriolus, e.g., C. hirsutus (JP 2238885). Suitable examples from bacteria include a laccase derivable from a strain of *Bacillus*. A laccase derived from Coprinopsis or Myceliophthora is preferred; in particular, a laccase derived from Coprinopsis cinerea, as disclosed in WO 97/08325; or from Myceliophthora thermophila, as disclosed in WO 95/33836.

Dispersants

The cleaning composition of the present invention can also contain dispersants. In particular, powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents

The cleaning composition of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent

The cleaning composition of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2.2'-disulfonate, 4,4'-bis-(2-anilino-4-(N-methyl-N-2-hydroxy-ethylamino)-s-triazin-6-ylamino) stilbene-2,2'-disulfonate, 4,4'-bis-(4-phenyl-1,2,3-triazol-2-yl)stilbene-2,2'-disulfonate and sodium 5-(2H-naphtho[1,2-d][1,2,3]triazol-2-yl)-2-[(E)-2-phenylvinyl]benzenesulfonate.

Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Other fluorescers suitable for use in the invention include the 1-3-diary) pyrazolines and the 7-alkylaminocoumarins. Suitable fluorescent brightener levels include lower levels of from about 0.01, from 0.05, from about 0.1 or even from about 0.2 wt % to upper levels of 0.5 or even 0.75 wt %.

Soil Release Polymers

The cleaning composition of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers is amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore, random graft co-polymers are suitable soil release polymers. Suitable graft co-polymers are described in more detail in WO 2007/138054, WO 2006/108856 and WO 2006/113314 (hereby incorporated by reference). Suitable polyethylene glycol polymers include random graft co-polymers comprising: (i) hydrophilic backbone comprising polyethylene glycol; and (ii) side chain(s) selected from the group consisting of: C4-C25 alkyl group, polypropylene, polybutylene, vinyl ester of a saturated C1-C6 mono-carboxylic acid, CI-C6 alkyl ester of acrylic or methacrylic acid, and mixtures thereof. Suitable polyethylene glycol polymers have a polyethylene glycol backbone with random grafted polyvinyl acetate side chains. The average molecular weight of the polyethylene glycol backbone can be in the range of from 2,000 Da to 20,000 Da, or from 4,000 Da to 8,000 Da. The molecular weight ratio of the polyethylene glycol backbone to the polyvinyl acetate side chains can be in the range of from 1:1 to 1:5, or from 1:1.2 to 1:2. The average number of graft sites per ethylene oxide units can be less than 1, or less than 0.8, the average number of graft sites per ethylene oxide units can be in the range of from 0.5 to 0.9, or the average number of graft sites per ethylene oxide units can be in the range of from 0.1 to 0.5, or from 0.2 to 0.4. A suitable polyethylene glycol polymer is Sokalan HP22. Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents

The cleaning composition of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Rheology Modifiers

The cleaning composition of the present invention may also include one or more rheology modifiers, structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040.

Other suitable cleaning composition components include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Formulation of Detergent Pproducts

The cleaning composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid.

Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blended compositions comprising hydrolytically degradable and water soluble polymer blends such as polylactide and polyvinyl alcohol (known under the Trade reference M8630 as sold by MonoSol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids: US2009/0011970 A1.

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent. A liquid or gel detergent may be non-aqueous.

Uses

The present invention is also directed to methods for using a hexosaminidase e.g. a *Lactobacillus* or *Streptococcus* hexosaminidase of the invention and compositions hereof. A hexosaminidase of the invention is useful in cleaning processes typically in laundry/textile/fabric (House hold laundry washing, Industrial laundry washing) or hard surface cleaning (ADW, car wash, Industrial surface).

One aspect of the invention relates to the use of a hexosaminidase e.g. *Lactobacillus* hexosaminidase for cleaning of an item, wherein the item is a textile or a surface.

One aspect of the invention relates to the use of a *Lactobacillus* or *Streptococcus* hexosaminidase for cleaning of an item, wherein the item is a textile or a surface, wherein the *hexosaminidase* is selected from the group consisting of polypeptides shown in SEQ ID NOs 3, SEQ ID NO 6, SEQ ID NO 9, SEQ ID NO 18 and polypeptides having at least 60%, at least 70%, at least 75%, at least 80%, at least 85%, at least 90%, at least 95%, at least 98% or such as at least 99% sequence identity hereto.

One aspect of the invention relates to the use of a *Lactobacillus* hexosaminidase of the invention,
a) for preventing, reducing or removing stickiness of the item;
b) for pretreating stains on the item;
c) for preventing, reducing or removing redeposition of soil during a wash cycle;
d) for preventing, reducing or removing adherence of soil to the item;
e) for maintaining or improving whiteness of the item;
f) for preventing, reducing or removal malodor from the item,
wherein the item is a textile.

One aspect of the invention relates to the use of a *Streptococcus* hexosaminidase of the invention,
a) for preventing, reducing or removing stickiness of the item;
b) for pretreating stains on the item;
c) for preventing, reducing or removing redeposition of soil during a wash cycle;
d) for preventing, reducing or removing adherence of soil to the item;
e) for maintaining or improving whiteness of the item;
f) for preventing, reducing or removal malodor from the item,
wherein the item is a textile.

One aspect of the invention relates to the use of a hexosaminidase e.g. dispersin, wherein the hexosaminidase is selected from the group consisting of polypeptides shown in SEQ ID NOs 3, SEQ ID NO 6, SEQ ID NO 9, SEQ ID NO 18 and polypeptides having at least 60%, at least 70%, at least 75%, at least 80%, at least 85%, at least 90%, at least 95%, at least 98% or such as at least 99% sequence identity hereto,
a) for preventing, reducing or removing stickiness of the item;
b) for pretreating stains on the item;
c) for preventing, reducing or removing redeposition of soil during a wash cycle;
d) for preventing, reducing or removing adherence of soil to the item;
e) for maintaining or improving whiteness of the item;
f) for preventing, reducing or removal malodor from the item,
wherein the item is a textile.

Use of Cleaning Composition

The detergent composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations. In a specific aspect, the present invention provides a detergent additive comprising one or more enzymes as described herein.

One aspect of the invention relates to the use of a composition, preferably a cleaning composition such as a detergent composition comprising a hexosaminidase e.g. obtained from *Lactobacillus* or *Streptococcus* for cleaning of an item, wherein the item is a textile or a surface.

One aspect of the invention relates to the use of a composition, preferably a cleaning composition such as a detergent composition comprising a hexosaminidase e.g. obtained from *Lactobacillus* or *Streptococcus* for cleaning of an item, wherein the item is a textile or a surface, wherein the hexosaminidase e.g. obtained from *Lactobacillus* or *Streptococcus* is selected from the group consisting of polypeptides shown in SEQ ID NO 3, SEQ ID NO 6, SEQ ID NO 9, SEQ ID NO 18 and polypeptides having at least 60%, at least 70%, at least 75%, at least 80%, at least 85%, at least 90%, at least 95%, at least 98% or such as at least 99% sequence identity hereto.

One aspect of the invention relates to the use of a composition, preferably a cleaning composition such as a detergent composition comprising a hexosaminidase e.g. obtained from *Lactobacillus* or *Streptococcus* of the invention,
a) for preventing, reducing or removing stickiness of the item;
b) for pretreating stains on the item;
c) for preventing, reducing or removing redeposition of soil during a wash cycle;
d) for preventing, reducing or removing adherence of soil to the item;
e) for maintaining or improving whiteness of the item;
f) for preventing, reducing or removal malodor from the item,
wherein the item is a textile.

One aspect of the invention relates to the use of a composition, preferably a cleaning composition such as a detergent composition comprising a hexosaminidase e.g. obtained from *Lactobacillus* or *Streptococcus*, wherein the hexosaminidase is selected from the group consisting of polypeptides shown in SEQ ID NO 3, SEQ ID NO 6, SEQ ID NO 9, SEQ ID NO 18 and polypeptides having at least 60%, at least 70%, at least 75%, at least 80%, at least 85%, at least 90%, at least 95%, at least 98% or such as at least 99% sequence identity hereto,
a) for preventing, reducing or removing stickiness of the item;
b) for pretreating stains on the item;
c) for preventing, reducing or removing redeposition of soil during a wash cycle;
d) for preventing, reducing or removing adherence of soil to the item;
e) for maintaining or improving whiteness of the item;
f) for preventing, reducing or removal malodor from the item,
wherein the item is a textile.

Methods

The invention further relates to a method of treating a method of treating a fabric comprising;
(a) contacting the fabric with an aqueous solution of hexosaminidase e.g. obtained from *Lactobacillus* or *Streptococcus*;
(b) and optionally rinsing and drying the textile.

One aspect relates to a method of treating a fabric comprising;
(a) contacting the fabric with an aqueous solution of hexosaminidase e.g. obtained from *Lactobacillus* or

*Streptococcus* is selected from the group consisting of polypeptides shown in SEQ ID NO 3, SEQ ID NO 6, SEQ ID NO 9, SEQ ID NO 18 and polypeptides having at least 60%, at least 70%, at least 75%, at least 80%, at least 85%, at least 90%, at least 95%, at least 98% or such as at least 99% sequence identity hereto;

(b) and optionally rinsing and drying the textile.

The invention further relates to a method for cleaning or laundering an item comprising the steps of:
 a. exposing an item to a wash liquor comprising a hexosaminidase e.g. obtained from *Lactobacillus* or *Streptococcus* of the invention or a detergent composition comprising a hexosaminidase;
 b. completing at least one wash cycle; and
 c. optionally rinsing the item,
wherein the item is a fabric.

The invention further relates to a method for cleaning or laundering an item comprising the steps of:
 a. exposing an item to a wash liquor comprising a hexosaminidase e.g. obtained from *Lactobacillus* or *Streptococcus* of the invention or a detergent composition comprising a hexosaminidase, wherein the hexosaminidase is selected from the group consisting of polypeptides shown in SEQ ID NO 3, SEQ ID NO 6, SEQ ID NO 9, SEQ ID NO 18 and polypeptides having at least 60%, at least 70%, at least 75%, at least 80%, at least 85%, at least 90%, at least 95%, at least 98% or such as at least 99% sequence identity hereto;
 b. completing at least one wash cycle; and
 c. optionally rinsing the item, wherein the item is a fabric.

One embodiment relates to a method, wherein the *Lactobacillus* hexosaminidase comprises one or more of the following motifs GXDE (SEQ ID NO 12), [EQ][NRSHA][YVFL][AGSTC][IVLF][EAQYN][SN] (SEQ ID NO 13), [VLIM][LIV]G[GAV]DE[VI][PSA] (SEQ ID NO 14), or [GK]A[IL][IL][KSR][LQ]L (SEQ ID NO 15).

One embodiment relates to a method, wherein the *Lactobacillus* hexosaminidase comprises the motifs GXDE (SEQ ID NO 12) and [EQ][NRSHA][YVFL][AGSTC][IVLF][EAQYN][SN] (SEQ ID NO 13).

One embodiment relates to a method, wherein the *Lactobacillus* hexosaminidase comprises the motifs [VLIM][LIV]G[GAV]DE[VI][PSA] (SEQ ID NO 14) and/or [GK]A[IL][IL][KSR][LQ]L (SEQ ID NO 15).

The pH of the liquid solution is in the range of 1 to 11, such as in the range of 5.5 to 11, such as in the range of 7 to 9, in the range of 7 to 8 or in the range of 7 to 8.5.

The wash liquor may have a temperature in the range of 5° C. to 95° C., or in the range of 10° C. to 80° C., in the range of 10° C. to 70° C., in the range of 10° C. to 60° C., in the range of 10° C. to 50° C., in the range of 15° C. to 40° C. or in the range of 20° C. to 30° C. In one aspect, the temperature of the wash liquor is 30° C.

The concentration of the hexosaminidase in the wash liquor is typically in the range of at least 0.00001 ppm to at least 10 ppm, at least 0.00002 ppm to at least 10 ppm, at least 0.0001 ppm to at least 10 ppm, at least 0.0002 ppm to at least 10 ppm, at least 0.001 ppm to at least 10 ppm, at least 0.002 ppm to at least 10 ppm, at least 0.01 ppm to at least 10 ppm, at least 0.02 ppm to at least 10 ppm, at least 0.1 ppm to at least 10 ppm, at least 0.2 ppm to at least 10 ppm, at least 0.5 ppm to at least 5 ppm.

DEFINITIONS

Biofilm is produced by any group of microorganisms in which cells stick to each other or stick to a surface, such as a textile, dishware or hard surface or another kind of surface. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces. The microbial cells growing in a biofilm are physiologically distinct from planktonic cells of the same organism, which, by contrast, are single-cells that may float or swim in a liquid medium. Bacteria living in a biofilm usually have significantly different properties from planktonic bacteria of the same species, as the dense and protected environment of the film allows them to cooperate and interact in various ways. One benefit of this environment for the microorganisms is increased resistance to detergents and antibiotics, as the dense extracellular matrix and the outer layer of cells protect the interior of the community. On laundry biofilm producing bacteria can be found among the following species: *Acinetobacter* sp., *Aeromicrobium* sp., *Brevundimonas* sp., *Microbacterium* sp., *Micrococcus luteus*, *Pseudomonas* sp., *Staphylococcus epidermidis*, and *Stenotrophomonas* sp. On hard surfaces biofilm producing bacteria can be found among the following species: *Acinetobacter* sp., *Aeromicrobium* sp., *Brevundimonas* sp., *Microbacterium* sp., *Micrococcus luteus*, *Pseudomonas* sp., *Staphylococcus epidermidis*, *Staphylococcus aureus* and *Stenotrophomonas* sp. In one aspect, the biofilm producing strain is *Brevundimonas* sp. In one aspect, the biofilm producing strain is *Pseudomonas* e.g. *Pseudomonas alcaliphila* or *Pseudomonas fluorescens*. In one aspect, the biofilm producing strain is Staphylococcus aureus.

By the term "deep cleaning" is meant disruption or removal of components of organic matter, e.g. biofilm, such as polysaccharides e.g. PNAG, proteins, DNA, soil or other components present in the organic matter.

Cleaning component: The cleaning component is different to the hexosaminidase. The precise nature of these additional components (e.g. adjuncts), and levels of incorporation thereof, will depend on the physical form of the composition and the nature of the operation for which it is to be used. Suitable cleaning component materials include, but are not limited to the components described below such as surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric agents, clay soil removal/anti-redeposition agents, brighteners, suds suppressors, dyes, perfumes, structure elasticizing agents, fabric softeners, carriers, hydrotropes, builders and co-builders, fabric huing agents, antifoaming agents, dispersants, processing aids, and/or pigments.

Cleaning Composition: The term "cleaning or detergent composition" refers to compositions that find use in the removal of undesired compounds from items to be cleaned, such as textiles. The cleaning composition may be used to e.g. clean textiles for both household cleaning and industrial cleaning. The terms encompass any materials/compounds selected for the particular type of cleaning composition desired and the form of the product (e.g., liquid, gel, powder, granulate, paste, or spray compositions) and includes, but is not limited to, detergent compositions (e.g., liquid and/or solid laundry detergents and fine fabric detergents; fabric fresheners; fabric softeners; and textile and laundry pre-spotters/pretreatment). In addition to containing the enzyme of the invention, the detergent formulation may contain one or more additional enzymes (such as proteases, amylases, lipases, cutinases, cellulases, endoglucanases, xyloglucanases, pectinases, pectin lyases, xanthanases, peroxidases, haloperoxygenases, catalases and mannanases, or any mixture thereof), and/or detergent adjunct ingredients such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

The term "hard surface cleaning" is defined herein as cleaning of hard surfaces wherein hard surfaces may include floors, tables, walls, roofs etc. as well as surfaces of hard objects such as cars (car wash) and dishes (dish wash). Dish washing includes but are not limited to cleaning of plates, cups, glasses, bowls, cutlery such as spoons, knives, forks, serving utensils, ceramics, plastics, metals, china, glass and acrylics.

The term "wash performance" is used as an enzyme's ability to remove stains or soil present on the object to be cleaned during e.g. wash or hard surface cleaning.

The term "whiteness" is defined herein as the quality or state of a textile of being white. Loss of whiteness may be due to removal of optical brighteners/hueing agents and result in a greying or yellowing of the textiles. Greying and yellowing can be due to soil redeposition, body soils, colouring from e.g. iron and copper ions or dye transfer. Whiteness might include one or several issues from the list below: colourant or dye effects; incomplete stain removal (e.g. body soils, sebum etc.); redeposition (greying, yellowing or other discolourations of the object) (removed soils reassociate with other parts of textile, soiled or unsoiled); chemical changes in textile during application; and clarification or brightening of colours.

The term "laundering" relates to both household laundering and industrial laundering and means the process of treating textiles with a solution containing a cleaning or detergent composition of the present invention. The laundering process can for example be carried out using e.g. a household or an industrial washing machine or can be carried out by hand.

By the term "malodor" is meant an odor which is not desired on clean items. The cleaned item should smell fresh and clean without malodors adhered to the item. One example of malodor is compounds with an unpleasant smell, which may be produced by microorganisms. Another example of unpleasant smell can be sweat or body odor adhered to an item which has been in contact with human or animal. Another example of malodor can be the odor from spices, which sticks to items for example curry or other exotic spices which smell strongly, tobacco, cooking smell (fried oil, fish etc.), scents of perfume such as deodorant and eau de cologne.

The term "mature polypeptide" means a polypeptide in its final form following translation and any post-translational modifications, such as N-terminus processing, C-terminus truncation, glycosylation, phosphorylation, etc.

The term "textile" means any textile material including yarns, yarn intermediates, fibers, non-woven materials, natural materials, synthetic materials, and any other textile material, fabrics made of these materials and products made from fabrics (e.g., garments and other articles). The textile or fabric may be in the form of knits, wovens, denims, non-wovens, felts, yarns, and towelling. The textile may be cellulose based such as natural cellulosics, including cotton, flax/linen, jute, ramie, sisal or coir or manmade cellulosics (e.g. originating from wood pulp) including viscose/rayon, cellulose acetate fibers (tricell), lyocell or blends thereof. The textile or fabric may also be non-cellulose based such as natural polyamides including wool, camel, cashmere, mohair, rabbit and silk or synthetic polymers such as nylon, aramid, polyester, acrylic, polypropylene and spandex/elastane, or blends thereof as well as blends of cellulose based and non-cellulose based fibers. Examples of blends are blends of cotton and/or rayon/viscose with one or more companion material such as wool, synthetic fiber (e.g. polyamide fiber, acrylic fiber, polyester fiber, polyvinyl chloride fiber, polyurethane fiber, polyurea fiber, aramid fiber), and/or cellulose-containing fiber (e.g. rayon/viscose, ramie, flax/linen, jute, cellulose acetate fiber, lyocell). Fabric may be conventional washable laundry, for example stained household laundry. When the term fabric or garment is used it is intended to include the broader term textiles as well.

The term "variant" means a polypeptide having the activity of the parent or precursor polypeptide and comprising an alteration, i.e., a substitution, insertion, and/or deletion, at one or more (e.g., several) positions compared to the precursor or parent polypeptide. A substitution means replacement of the amino acid occupying a position with a different amino acid; a deletion means removal of the amino acid occupying a position; and an insertion means adding an amino acid adjacent to and immediately following the amino acid occupying a position.

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 6.6.0 or later. The parameters used are a gap open penalty of 10, a gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment).

Clade: a group of polypeptides clustered together based on homologous features traced to a common ancestor. Polypeptide clades can be visualized as phylogenetic trees and a clade is a group of polypeptides that consists of a common ancestor and all its lineal descendants Nomenclature For purposes of the present invention, the nomenclature [IV] or [IN] means that the amino acid at this position may be isoleucine (Ile, I) or valine (Val, V). Likewise, the nomenclature [LVI] and [L/V/I] means that the amino acid at this position may be a leucine (Leu, L), valine (Val, V) or isoleucine (Ile, I), and so forth for other combinations as described herein. Unless otherwise limited further, the amino acid X is defined such that it may be any of the 20 natural amino acids.

Unless otherwise indicated, or if it is apparent from the context that something else is intended, all percentages are percentage by weight (% w/w) or (wt %).

The invention is further described in the following non-limiting paragraphs

1. A cleaning composition comprising at least 0.01 mg *Lactobacillus hexosaminidase* and a cleaning component, wherein the cleaning component is
   (a) at least one surfactant;
   (b) at least one builder; or
   (c) at least one polymer.

2. The composition according to paragraph 1, wherein the composition comprises from about 1% to about 40% by weight of an anionic surfactant, such as from about 5% to about 30%, including from about 5% to about 15%, or from about 15% to about 20%, or from about 20% to about 25% anionic surfactant, preferably selected from linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

3. The composition according to paragraph 1 or 2 comprising from about 0.2% to about 40% by weight of a nonionic surfactant, for example from about 0.5% to about 30%, in particular from about 1% to about 20%, from about 3% to about 10%, such as from about 3% to about 5%, from about 8% to about 12%, or from about 10% to about 12% of at least one nonionic surfactant, preferably selected from alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA) and combinations thereof.

4. The composition according to any of paragraphs 1 to 3, wherein the composition comprises from about 1 wt % to about 60 wt %, from about 5 wt % to about 50 wt %, from about 10 wt % to about 40 wt % of at least one builder, preferably selected from citric acid, methylglycine-N,N-diacetic acid (MGDA) and/or glutamic acid-N,N-diacetic acid (GLDA) and mixtures thereof.

5. The composition according to any of paragraphs 1 to 4, wherein the composition 0-50% by weight, such as 1-40%, such as 1-30%, such as about 1% to about 20% of at least one bleach component preferably selected from a peroxide, preferably percabonate and a catalyst preferably a metal-containing bleach catalyst such as 1,4,7-trimethyl-1,4,7-triazacyclononane or manganese (II) acetate tetrahydrate (MnTACN).

6. The composition according to any of the preceding paragraphs, wherein the *Lactobacillus hexosaminidase* comprises the one or more of the motifs GXDE (SEQ ID NO 12), [EQ][NRSHA][YVFL][AGSTC][IVLF][EAQYN][SN] (SEQ ID NO 13), [VLIM][LIV]G[GAV]DE[VI][PSA] (SEQ ID NO 14), or [GK]A[IL][IL][KSR][LQ]L (SEQ ID NO 15).

7. The composition according to any of the preceding paragraphs, wherein the *Lactobacillus hexosaminidase* comprises the motifs GXDE (SEQ ID NO 12) and [EQ][NRSHA][YVFL][AGSTC[]IVLF][EAQYN][SN] (SEQ ID NO 13).

8. The composition according to paragraph 7, wherein the *Lactobacillus hexosaminidase* comprises the motifs [VLIM][LIV]G[GAV]DE[VI][PSA] (SEQ ID NO 14) and/or [GK]A[IL][IL][KSR][LQ]L (SEQ ID NO 15).

9. The composition according to any of the preceding paragraphs, wherein the *Lactobacillus hexosaminidase* is selected from the group consisting of polypeptides having the amino acid sequence of SEQ ID NO 3, SEQ ID NO 6, SEQ ID NO 9, and polypeptides having at least 60%, at least 70%, at least 75%, at least 80%, at least 85%, at least 90%, at least 95%, at least 98% or such as at least 99% sequence identity hereto.

10. The composition according to any of the preceding paragraphs, wherein the polypeptide having hexosaminidase activity comprises the amino acid sequence of SEQ ID NO 3 or polypeptides having at least 60% e.g. 80%, 85%, 90%, 95%, 98% or 99% sequence identity hereto.

11. The composition according to any of the preceding paragraphs, wherein the polypeptide having hexosaminidase activity comprises the amino acid sequence of SEQ ID NO 6 or polypeptides having at least 60% e.g. 80%, 85%, 90%, 95%, 98% or 99% sequence identity hereto.

12. The composition according to any of the preceding paragraphs, wherein the polypeptide having hexosaminidase activity comprises the amino acid sequence of SEQ ID NO 9 or polypeptides having at least 60% e.g. 80%, 85%, 90%, 95%, 98% or 99% sequence identity hereto.

13. The composition according to any of the preceding paragraphs, wherein the composition further comprises one or more enzymes selected from the group consisting of proteases, lipases, cutinases, amylases, carbohydrases, cellulases, pectinases, mannanases, arabinases, galactanases, xylanases and oxidases.

14. Use of a composition according to any of the previous paragraphs for cleaning of an item, wherein the item is a textile or a surface.

15. Use of a composition according to paragraph 14, preferably a cleaning composition such as a detergent composition comprising a *Lactobacillus* hexosaminidase,
   a) for preventing, reducing or removing stickiness of the item;
   b) for pretreating stains on the item;
   c) for preventing, reducing or removing redeposition of soil during a wash cycle;
   d) for preventing, reducing or removing adherence of soil to the item;
   e) for maintaining or improving whiteness of the item;
   f) for preventing, reducing or removing malodor from the item,
      wherein the item is a textile.

16. Use according to paragraph 14 or 15, wherein the *Lactobacillus hexosaminidase* comprises one or more of the following motifs GXDE (SEQ ID NO 12), [EQ][NRSHA][YVFL][AGSTC][IVLF][EAQYN][SN] (SEQ ID NO 13), [VLIM][LIV]G[GAV]DE[VI][PSA] (SEQ ID NO 14), or [GK]A[IL][IL][KSR][LQ]L (SEQ ID NO 15).

17. Use according to any of paragraphs 14 to 16, wherein the *Lactobacillus hexosaminidase* comprises the motifs GXDE (SEQ ID NO 12) and [EQ][NRSHA][YVFL][AG-STC][IVLF][EAQYN][SN] (SEQ ID NO 13).

18. Use according to paragraphs 14 to 16, wherein the *Lactobacillus hexosaminidase* comprises the motifs [VLIM][LIV]G[GAV]DE[VI][PSA] (SEQ ID NO 14) and/or [GK]A[IL][IL][KSR][LQ]L (SEQ ID NO 15).

19. Use of a composition according to any of paragraphs 14 to 18, wherein the *Lactobacillus hexosaminidase* is selected from the group consisting of polypeptides shown in SEQ ID NO 3, SEQ ID NO 6, SEQ ID NO 9, or polypeptides having at least 60%, at least 70%, at least 75%, at least 80%, at least 85%, at least 90%, at least 95%, at least 98% or such as at least 99% sequence identity hereto.

20. A method of formulating a cleaning composition comprising adding a *Lactobacillus hexosaminidase* and at least one cleaning component.

21. A kit intended for cleaning, wherein the kit comprises a solution of an enzyme mixture comprising *Lactobacillus hexosaminidase*, and an additional enzyme selected from proteases, amylases, cellulases and lipases.

22. A method of treating a fabric comprising;
  (a) contacting the fabric with an aqueous solution of *Lactobacillus* hexosaminidase;
  (b) and optionally rinsing and drying the textile.

23. A method for cleaning or laundering an item comprising the steps of:
  (a) exposing an item to a wash liquor comprising a *Lactobacillus* hexosaminidase of the invention or a detergent composition comprising a *Lactobacillus* hexosaminidase;
  (b) completing at least one wash cycle; and
  (c) optionally rinsing the item, wherein the item is a fabric.

24. The method according to paragraph 22 or 23, wherein the *Lactobacillus hexosaminidase* comprises one or more of the following motifs GXDE (SEQ ID NO 12), [EQ][NRSHA][YVFL][AGSTC][IVLF][EAQYN][SN] (SEQ ID NO 13), [VLIM][LIV]G[GAV]DE[VI][PSA] (SEQ ID NO 14), or [GK]A[IL][IL][KSR][LQ]L (SEQ ID NO 15).

25. The method according to any of paragraphs 22 to 24, wherein the *Lactobacillus hexosaminidase* comprises the motifs GXDE (SEQ ID NO 12) and [EQ][NRSHA][YVFL][AGSTC][IVLF][EAQYN][SN] (SEQ ID NO 13).

26. The method according to paragraph 25, wherein the *Lactobacillus hexosaminidase* comprises the motifs [VLIM][LIV]G[GAV]DE[VI][PSA] (SEQ ID NO 14) and/or [GK]A[IL][IL][KSR][LQ]L (SEQ ID NO 15).

27. The method according to paragraph 22 to 26, wherein the *Lactobacillus hexosaminidase* is selected from the group consisting of polypeptides shown in SEQ ID NO 3, SEQ ID NO 6, SEQ ID NO 9, or polypeptides having at least 60%, at least 70%, at least 75%, at least 80%, at least 85%, at least 90%, at least 95%, at least 98% or such as at least 99% sequence identity hereto.

EXAMPLES

Assays

Wash Assay

Mini Launder-O-Meter (MiniLOM) Model Wash System

MiniLOM is a mini wash system in which washes are performed in 50 ml test tubes placed in a Stuart rotator. Each tube simulates one small washing machine and during an experiment, each will contain a solution of a specific detergent/enzyme system to be tested along with the soiled and unsoiled fabrics it is tested on. Mechanical stress is achieved via rotation (typically 20 rpm), and the temperature is controlled by placement of the rotator in a heating cabinet/room.

Assay I: Testing of Hexosaminidase Activity

The hexosaminidase activity of the polypeptides listed in the table below was determined using 4-Methylumbelliferyl N-acetyl-β-D-glucosaminide (Sigma-Aldrich) as substrate. The enzymatic reaction was performed in triplicates in a 96 well flat bottom polystyrene microtiter plate (Thermo Scientific) with the following conditions: 20 mM 3-(N-morpholino) propanesulfonic acid pH 7 buffer, 5 mM 4-Methylumbelliferyl N-acetyl-β-D-glucosaminide, 0.01 vol% (% w/w) Brij 35 (Polyoxyethylene lauryl ether, CAS 9002-92-0) and 50 nM purified enzyme sample in a total reaction volume of 200 µl. Blank samples without polypeptide were run in parallel. The reactions were carried out at room temperature using a SpectraMax M2e Microplate Reader from Molecular Devices. Excitation wavelength was set to 368 nm and emission wavelength to 448 nm. Fluorescent signal was followed for 15 min in Kinetic Mode. Initial rate of reaction was evaluated in units of RFU/min by calculating the maximum initial increase in fluorescent signal over time as 4-Methylumbelliferyl was released from 4-Methylumbelliferyl N-acetyl-β-D-glucosaminide substrate due to enzymatic reaction.

Composition of Model Detergent A (Liquid)

Ingredients: 12% LAS, 11% AEO Biosoft N25-7 (NI), 5% AEOS (SLES), 6% MPG (monopropylene glycol), 3% ethanol, 3% TEA, 2.75% coco soap, 2.75% soya soap, 2% glycerol, 2% sodium hydroxide, 2% sodium citrate, 1% sodium formate, 0.2% DTMPA and 0.2% PCA (all percentages are w/w).

Composition of Model Detergent T (Powder)

Ingredients: 11% LAS, 2% AS/AEOS, 2% soap, 3% AEO, 15.15% sodium carbonate, 3% sodium silicate, 18.75% zeolite, 0.15% chelant, 2% sodium citrate, 1.65% AA/MA copolymer, 2.5% CMC and 0.5% SRP (all percentages are w/w).

Triple-20 Nonionic Model Detergent was prepared by dissolving 3.33 g/l non-ionic detergent containing NaOH 0.87%, MPG (Monopropylenglycol) 6%, Glycerol 2%, Soap-soy 2.75%, Soap-coco 2.75%, PCA (Sokalon CP-5) 0.2%, AEO Biosoft N25-7(NI) 16%, Sodium formiate 1%, Sodium Citrate 2%, DTMPA 0.2%, Ethanol (96%) 3%, adjustment of pH with NaOH or Citric acid as water to 100% (all percentages are w/w (weight volume) in water with hardness 15 dH.

Composition of Persil Universal Gel

Ingredients: 15-30% anionic surfactants, 5-15% nonionic surfactant, <5% Phosphonate, soap, perfume, optical brightener and enzymes.

Example 1: Strain and DNA

The gene sequence encoding the hexosaminidase polypeptides from the strains *Lactobacillus paraplantarum* DSM 10667 and *Lactobacillus apinorum* respectively were found in the public database (Accession number SWISSPROT:

A0A0R1R622 and EMBLWGS:AZEO01000001 for SEQ ID 1 and SWISSPROT:A0A0M9D3N9 and EMBLWGS: JXCT01000010 for SEQ ID 4). The DNA encoding the hexosaminidase having the polypeptide comprised in SEQ ID 8 was isolated from a *Lactobacillus paraplantarum* bacterial strain, isolated from an environmental sample collected in Germany. Chromosomal DNA from the *Lactobacillus paraplantarum* strain was isolated by QIAamp DNA Blood Mini Kit (Qiagen, Hilden, Germany) and subjected to full genome sequencing using Illumina technology. The genome sequence was analyzed for protein sequences that have glycosyl hydrolase domains (GH20, www.cazy.org). One gene with corresponding sequence SEQ ID 7 was subsequently identified.

The codon optimized synthetic DNA encoding the mature peptide sequences of two hexosaminidases with SEQ ID 3 and 6 were ordered from the company Geneart.

TABLE 2

| SEQ ID | donor | country of origin |
| --- | --- | --- |
| SEQ ID 3 | *Lactobacillus paraplantarum* DSM 10667 | France |
| SEQ ID 6 | *Lactobacillus apinorum* | Sweden |
| SEQ ID 9 | *Lactobacillus paraplantarum* | Germany |
| SEQ ID NO 18* | *Streptococcus merionis* | Germany |

*The dispersin comprising the amino acids sequence shown in SEQ ID NO 18 was expressed and purified as described in example 1 or 2 for the Lactobacillus.

Example 2: Cloning and Expression of glycol_hydro_20 Hexosaminidases

The codon optimized synthetic genes encoding the mature peptide sequences of the hexosaminidase with SEQ ID 3 and 6 were inserted into a *Bacillus* expression vector as described in WO12/025577. Briefly, the DNA encoding the mature peptide of the glycol_hydro_20 hexosaminidase gene was cloned in frame to a *Bacillus clausii* secretion signal (BcSP; with the following amino acid sequence: MKKPLGKIVASTALLISVAFSSSIASA (SEQ ID NO: 10). BcSP replaced the native secretion signal in the gene. Downstream of the BcSP sequence, an affinity tag sequence was introduced to ease the purification process (His-tag; with the following amino acid sequence: HHHHHHPR (SEQ ID NO: 11). The gene that was expressed therefore comprised the BcSP sequence followed by the His-tag sequence followed by the mature wild type glycol_hydro_20 sequence. The DNA encoding the mature peptide of the glycol_hydro_20 beta-hexosaminidase gene SEQ ID 9 was amplified from the *Lactobacillus paraplantarum* genomic DNA by standard PCR techniques using specific primers containing an overhang to the cloning vector. The gene was consecutively cloned in frame to a *Bacillus clausii* secretion signal as described above. The final expression plasmid (BcSP-His-tag- glycol_hydro_20) was transformed into a *Bacillus subtilis* expression host. The glycol_hydro_20 BcSP-fusion gene was integrated by homologous recombination into the *Bacillus subtilis* host cell genome upon transformation. The gene construct was expressed under the control of a triple promoter system (as described in WO99/43835). The gene coding for chloramphenicol acetyltransferase was used as maker (as described in (Diderichsen et al., 1993, *Plasmid* 30: 312-315)). Transformants were selected on LB media agar supplemented with 6 micrograms of chloramphenicol per ml. One recombinant *Bacillus subtilis* clone containing the glycol_hydro_20 expression construct was selected and was cultivated on a rotary shaking table in 500 ml baffled Erlenmeyer flasks each containing 100 ml yeast extract-based media. After 3-5 days' cultivation time at 30° C. to 37° C., the enzyme containing supernatant was harvested by centrifugation and the enzymes was purified by His-tag purification.

Example 3: His Tag Purification Method

The His-tagged glycol_hydro_20 hexosaminidase enzymes were purified by immobilized metal chromatography (IMAC) using $Ni^{2+}$ as the metal ion on 5 mL HisTrap Excel columns (GE Healthcare Life Sciences). The purification took place at pH 7 and the bound protein was eluted with imidazole. The purity of the purified enzymes was checked by SDS-PAGE and the concentration of the enzyme determined by Absorbance 280 nm after a buffer exchange in 50 mM HEPES, 100 mM NaCl pH 7.0

SEQ ID NO 10: MKKPLGKIVASTALLISVAFSSSIASA

SEQ ID NO 11: HHHHHHPR

Example 4: Biofilm Growth and Detachment Assay

*Staphylococcus aureus* 15981 was kindly provided by Iñigo Lasa (Valle et al., Mol Microbiol. 2003 May; 48 (4):1075-87). The strain was grown on trypticase soy agar (TSA) at 37° C. overnight. Next day, a single colony was transferred to 15 ml tripticase soy broth (TSB) and incubated 5 hours at 37° C. under shaking. The culture was diluted 1:100 in TSB+1% glucose and 100 µL of the bacterial suspension was transferred to each well of a 96-well microtiter plates (Thermo Scientific, Nunclon Delta Surface, cat #167008) and incubated 24 hours at 37° C. without shaking. and 100 µL of the bacterial suspension was transferred to each well of a 96-well microtiter plates (Thermo Scientific, Nunclon Delta Surface, cat #167008) and incubated 24 hours at 37° C. without shaking. Supernatant was aspirated and wells were washed with 100 µL of 0.9% sodium chloride and filled with 100 µL of either hard water or 3.3 gr/L non-ionic detergent or 3.3 gr/L model A detergent (composition hard water and non-ionic and model A) containing 0 (control) or 20, 10, 5, 2.5, 1.25, 0.62, 0.31, 0.16, 0.08, 0.04, 0.02 and 0.01 µg/mL of enzyme SEQ ID 3, 6 and 9. After incubation at 37° C. for 1 hour, wells were washed with water and stained for 15 min with 100 µL of 0.095% crystal violet solution (SIGMA V5265). Wells were then rinsed twice with 100 µL water, dried and the plates were scanned.

The lowest concentration of each enzyme that could remove the visible formation of biofilm of *S. aureus* 15981 after 1 hour incubation, in the presence and absence of detergent was determined (see Table 3). All enzymes were assayed per duplicate in three independent assays. The average of the minimal concentration of enzyme that removed the visible formation of *S. aureus* 15981 from the three assays is listed in Table 3.

Table 3. Minimal concentration of enzyme that can remove the visible formation of S. aureus 15981 after 1 hour incubation in either hard water or model A detergent

TABLE 3

| SEQ ID | Minimal concentration for biofilm removal in hard water µg/mL | Minimal concentration for biofilm removal in non-ionic detergent µg/mL | Minimal concentration for biofilm removal in model A detergent µg/mL |
|---|---|---|---|
| 3 | 0.04 | 0.16 | 0.16 |
| 6 | 0.62 | 2.08 | 3.75 |
| 9 | 13.33 | 13.33 | >20 |

Example 5: Cleaning Properties of Powder Model Detergents

A crude EPS (extracellular polymeric substances) extract was prepared from Pseudomonas fluorescens (Isolate from Iceland) as follows: P. fluorescens was restreaked on TSA and incubated for 1 day at 20° C. The strain was inoculated in TSB and incubated O/N at 20° C. After propagation, the culture was diluted (1:100) in M63 supplemented medium (15 mM $(NH_4)_2SO_4$, 100 mM $KH_2PO_4$, 1.8 µM $FeSO_4$, 1 mM $MgSO_4.7H2O$, 0.4% (w/v) glycerol, 0.2% (w/v) Casamino acids and 0.0001% (w/v) Thiamine), added to a Corning® CellBIND® 225 cm² Angled Neck Cell Culture Flasks with Vent Cap (400 ml per flask) and incubated statically for 3 days at 20° C. The biofilm culture was subsequently pelleted by centrifugation (10 min, 8000 g, 25° C.), and the cells were resuspended in 3M NaCl (4 ml per flask) and incubated for 30 min at 30° C. to extract the surface-associated EPS. The EPS-containing supernatant obtained after centrifugation (10 min, 5000 g, 25° C.) was stored at −20° C. until further use.

For wash performance testing, 50 ul aliquots of the crude EPS extract was spotted on sterile textile swatches (WFK20A) and incubated for 15 min at ambient temperature. The swatches (sterile or with EPS) were placed in 50 mL test tubes and 10 mL of wash liquor (15° dH water with 0.2 g/L iron(III) oxide nano-powder (544884; Sigma-Aldrich) with 5.3 g/L model T powder detergent) and enzyme was added to each tube. Washes without enzyme were included as controls. The test tubes were placed in a Stuart rotator and incubated for 1 hour at 37° C. at 20 rpm. The wash liquor was then removed, and the swatches were rinsed twice with 15° dH water and left to dry on filter paper overnight. The remission ($REM^{460nm}$) values were measured using a Macbeth Color-Eye 7000 (CE7000), and are displayed in table 4. Delta values ($REM^{460nm}_{(washed\ with\ enzyme)} - REM^{460nm}_{(washed\ without\ enzyme)}$) are also indicated.

TABLE 4

Cleaning effects of hexosaminidase (SEQ ID NO 3) in powder model detergent T

| Swatch | Enzyme | Enzyme concentration (µg/ml) | Average REM (460nm) | ΔREM (460nm) |
|---|---|---|---|---|
| wfk20A | No enzyme | 0 | 61.4 | |
| wfk20, EPS | No enzyme | 0 | 52.8 | |
| wfk20, EPS | SEQ ID NO 3 | 0.2 | 60.5 | 7.6 |
| wfk20, EPS | SEQ ID NO 3 | 2 | 67.5 | 14.6 |

Example 6. Cleaning Properties of Hexosaminidases in Liquid Model Detergents

A crude extract of biofilm extracellular polymeric substances (EPS) was prepared from Staphylococcus aureus 15981 (kind gift from Iñigo Lasa (Valle, J., A. Toledo-Arana, C. Berasain, J. M. Ghigo, B. Amorena, J. R. Penades, and I. Lasa. 2003, Mol. Microbiol. 48:1075-1087) as follows: 500 mL of TSB+1% glucose (24563; Roquette Freres) was inoculated, aliquoted into 50 ml conical centrifuge tubes (339652; Thermo Scientific Nunc) and incubated for 24 hours at 37° C. under shaking conditions (200 rpm). Following incubation, the cells were pelleted by centrifugation (10 min, 6000 g, 25° C.), pooled and resuspended in 4 ml 3M NaCl. The suspension was vortexed vigorously and incubated for 15 min at ambient temperature to extract the surface-associated EPS. The cells were then re-pelleted (10 min, 5000 g, 25° C.) and the EPS-containing supernatant was retrieved. Milli-Q water was added (6 ml) and the solution was sterile-filtered twice (0.45 µm followed by 0.2 µm). The crude extract was stored at −20° C. until further use. For wash performance testing, 50 ul aliquots of the crude EPS extract was spotted on sterile textile swatches (WFK20A) and incubated for 15 min at ambient temperature. The swatches (sterile or with EPS) were placed in 50 mL test tubes and 10 mL of wash liquor (15° dH water with 0.2 g/L iron(III) oxide nano-powder (544884; Sigma-Aldrich) with 3.33 g/L liquid model A detergent or 3.33 g/L nonionic model detergent) and enzyme was added to each tube. Washes without enzyme were included as controls. The test tubes were placed in a Stuart rotator and incubated for 1 hour at 37° C. at 20 rpm. The wash liquor was then removed, and the swatches were rinsed twice with 15° dH water and left to dry on filter paper overnight. The remission ($REM^{460nm}$) values were measured using a Macbeth Color-Eye 7000 (CE7000), and are displayed in table 5 and 6. Delta values ($REM^{460nm}_{(washed\ with\ enzyme)} - REM^{460nm}_{(washed\ without\ enzyme)}$) are also indicated.

TABLE 5

Cleaning effects in liquid model detergent A

| Swatch | Enzyme | Enzyme concentration (µg/ml) | REM (460nm) | ΔREM |
|---|---|---|---|---|
| wfk20A | No enzyme | 0.0 | 58.5 | |
| EPS | No enzyme | 0.0 | 30.1 | |
| EPS | SEQ ID NO 3 | 2.0 | 65.5 | 35.4 |
| EPS | SEQ ID NO 3 | 0.2 | 58.2 | 28.1 |
| EPS | SEQ ID NO 9 | 2.0 | 38.6 | 8.5 |
| EPS | SEQ ID NO 9 | 0.2 | 32.1 | 2.0 |

TABLE 6 cleaning effects in liquid nonionic model detergent

| Swatch | Enzyme | Enzyme concentration (µg/ml) | REM (460nm) | ΔREM |
|---|---|---|---|---|
| wfk20A | No enzyme | 0.0 | 59.7 | |
| EPS | No enzyme | 0.0 | 30.4 | |
| EPS | SEQ ID NO 3 | 20.0 | 63.2 | 32.8 |
| EPS | SEQ ID NO 3 | 2.0 | 61.3 | 30.8 |
| EPS | SEQ ID NO 3 | 0.2 | 60.9 | 30.4 |
| EPS | SEQ ID NO 6 | 20.0 | 46.1 | 15.6 |
| EPS | SEQ ID NO 6 | 2.0 | 33.6 | 3.1 |

TABLE 6-continued cleaning effects in liquid nonionic model detergent

| Swatch | Enzyme | Enzyme concentration (µg/ml) | REM (460nm) | ΔREM |
|---|---|---|---|---|
| EPS | SEQ ID NO 6 | 0.2 | 31.3 | 0.9 |
| EPS | SEQ ID NO 9 | 20.0 | 63.9 | 33.4 |
| EPS | SEQ ID NO 9 | 2.0 | 45.4 | 15.0 |
| EPS | SEQ ID NO 9 | 0.2 | 34.4 | 4.0 |

Example 7: Construction of Clades and Phylogenetic Trees

The Glyco_hydro_20 domain includes the polypeptides of the invention having hexosaminidase e.g. PNAG activity and comprises the FQS, GADE and/or GAIL clades.

A phylogenetic tree was constructed, of polypeptide sequences containing a Glyco_hydro_20 domain, as defined in PFAM (PF00728, Pfam version 31.0 Finn (2016). Nucleic Acids Research, Database Issue 44:D279-D285). The phylogenetic tree was constructed from a multiple alignment of mature polypeptide sequences containing at least one Glyco_hydro_20 domain. The sequences were aligned using the MUSCLE algorithm version 3.8.31 (Edgar, 2004. Nucleic Acids Research 32(5): 1792-1797), and the trees were constructed using FastTree version 2.1.8 (Price et al., 2010, PloS one 5(3)) and visualized using iTOL (Letunic & Bork, 2007. Bioinformatics 23(1): 127-128). The polypeptide sequences containing a Glyco_hydro_20 domain comprises several motifs; one example is GXDE (SEQ ID NO 12), situated in positions 153 to 156 in *Lactobacillus paraplantarum* (SEQ ID NO 3). Residues D and E are the key catalytic residues of Glyco_hydro_20 enzymes (position 155 to 156 in SEQ ID NO 3).

The polypeptides in Glyco_hydro_20 can be separated into multiple distinct sub-clusters, or clades as listed below. The distinct motifs for each clade are described in details below.

Generation of FQS Clade

A clade, preferably shared by the polypeptides of the invention, was identified. This clade has not been described previously. The clade is termed FQS and polypeptides of this clade comprises Glyco_hydro_20 domain polypeptides of bacterial origin and are in addition to having PNAG activity, characterized by comprising a certain motif. The polypeptides of the clade comprise the motif example [EQ][NRSHA][YVFL][AGSTC][IVLF][EAQYN][SN] (SEQ ID NO 13), corresponding to EHLCFQS at position 48 to 54 of SEQ ID NO 3.

Generation of GADE Clade

A clade, preferably shared by the polypeptides of the invention, was identified. This clade has not been described previously. The clade is termed GADE and polypeptides of this clade comprise Glyco_hydro_20 domain polypeptides of bacterial origin and are in addition to having PNAG activity, characterized by comprising certain motifs. The polypeptides of the clade comprise the motif example [VLIM][LIV]G[GAV]DE[VI][PSA] (SEQ ID NO 14), corresponding to position 151 to 158 of SEQ ID NO 3, where G and DE (corresponding to positions 153 and 155-156 of SEQ ID NO 3) are fully conserved in GADE clade and part of the active site. Residues D and E are the key catalytic residues of Glyco_hydro_20 enzymes (position 155 to 156 in SEQ ID NO 3).

Generation of GAIL Clade

The GAIL clade comprises GADE domain polypeptides of bacterial origin, having hexosaminidase e.g. PNAG activity. This clade has not been described previously, and defines a cluster within the polypeptides of the invention. The clade is termed GAIL and polypeptides of this clade comprise Glyco_hydro_20 domain polypeptides of bacterial origin, and are in addition to having PNAG activity, characterized by comprising certain polypeptide motifs. The polypeptides of the domain comprise the motif example [GK]A[IL][IL][KSR][LQ]L (SEQ ID NO 15), corresponding to position 96 to 102 of SEQ ID NO 3, where A and L (corresponding to positions 97 and 102 of SEQ ID NO 3) are fully conserved in GAIL clade. Examples of polypeptides of the invention included in the clade are SEQ ID NO 3 and SEQ ID NO 9.

An alignment of the polypeptides of the invention is shown in FIG. 2. A phylogenetic tree of the polypeptides of the invention is shown in FIG. 1.

Example 8 Cleaning in Full-Scale Washing Machine

For wash performance testing in full scale washing machines, the *P. fluorescens* and *S. aureus* EPS extracts previously mentioned were spotted on 5×5 cm sterile textile swatches (WFK20A, 250 µl aliquots) and left to soak for 15 min at ambient temperature. The swatches were then attached to ballast tea towels and washed in Miele Laundry Washing Machines (Miele Softtronic, W2245) with and without enzyme, in liquid or powder detergent. The washes were run in tap water with 0.08 g/L iron(III) oxide nanopowder (544884; Sigma-Aldrich) in 4.6 g/L liquid detergent (Persil Universal gel) or with 0.7 g/L WFK 09V pigment soil (Wfk-Testgewebe GmbH, #00500) in 5.3 g/L powder model detergent T, respectively. The 30° C. Color program was used for these tests (run time 1 h, 26 min). After washing, the items were line-dried at room temperature overnight. The remission ($REM^{460nm}$) values were measured using a Macbeth Color-Eye 7000 (CE7000), and are displayed in table 7 and 8. Wash performances ($\Delta REM(460$ nm$) = REM^{460nm}_{(washed\ with\ enzyme)} - REM^{460nm}_{(washed\ without\ enzyme)}$) are also indicated.

TABLE 7

Cleaning of SEQ ID NO 3 in full-scale washing machine in liquid detergent

| EPS spotted on T-shirt | Enzyme | Average Rem460nm values | Wash performance (ΔRem460nm) |
|---|---|---|---|
| P.fluorescens EPS, wfk20A | No enzyme | 47.4 | |
| P.fluorescens EPS, wfk20A | 0.2 µg/ml SEQ ID NO 3 | 72.2 | 24.8 |
| S.aureus EPS, wfk20A | No enzyme | 41.2 | |
| S.aureus EPS, wfk20A | 0.2 µg/ml SEQ ID NO 3 | 66.5 | 25.3 |

TABLE 8

Cleaning of SEQ ID NO 3 in full-scale washing machine in powder model detergent T

| EPS spotted on T-shirt | Enzyme | Average Rem460nm values | Wash performance (ΔRem460nm) |
|---|---|---|---|
| P.fluorescens EPS, wfk20A | No enzyme | 58.6 | |
| P.fluorescens EPS, wfk20A | 0.2 ug/ml SEQ ID NO 3 | 64.0 | 5.4 |
| S.aureus EPS, wfk20A | No enzyme | 60.2 | |
| S.aureus EPS, wfk20A | 0.2 ug/ml SEQ ID NO 3 | 63.3 | 3.1 |

Example 9 Cleaning Properties of Hexosaminidase in Liquid Model Detergent on EPS from Different Microorganisms Crude extracts of biofilm extracellular polymeric substances (EPS) were prepared from S. aureus and P. fluorescens as described above. For wash performance testing, 50 ul aliquots of the crude EPS extracts were spotted on sterile textile swatches (WFK20A) and incubated for 15 min at ambient temperature. The swatches (sterile or with EPS) were placed in 50 mL test tubes and 10 mL of wash liquor (15° dH water with 0.2 g/L iron(III) oxide nano-powder (544884; Sigma-Aldrich) with 3.33 g/L liquid model A detergent) and enzyme was added to each tube. Washes without enzyme were included as controls. The test tubes were placed in a Stuart rotator and incubated for 1 hour at 37° C. at 20 rpm. The wash liquor was then removed, and the swatches were rinsed twice with 15° dH water and left to dry on filter paper overnight. The remission ($REM^{460nm}$) values were measured using a Macbeth Color-Eye 7000 (CE7000), and are displayed in table 9. Wash performances ($\Delta REM(460\ nm) = REM^{460nm}_{(washed\ with\ enzyme)} - REM^{460nm}_{(washed\ without\ ensyme)}$) are also indicated.

TABLE 9

Cleaning effects of Hexosaminidase with SEQ ID NO 18 in liquid model detergent on EPS from different microorganisms

| Enzyme | Enzyme concentration (µg/ml) | Average REM (460nm) values | Wash performance (ΔREM (460nm) |
|---|---|---|---|
| Clean textile (wfk20A), no EPS | 0 | 59.3 | |
| P. fluorescens EPS (wfk20A) | 0 | 35.0 | |
| P. fluorescens EPS (wfk20A) | SEQ ID NO 18 | 0.002 | 39.3 | 4.3 |
| P. fluorescens EPS (wfk20A) | SEQ ID NO 18 | 0.02 | 51.4 | 16.4 |
| P. fluorescens EPS (wfk20A) | SEQ ID NO 18 | 0.2 | 56.4 | 21.4 |
| S.aureus EPS (wfk20A) | 0 | 34.7 | |
| S.aureus EPS (wfk20A) | SEQ ID NO 18 | 0.002 | 45.5 | 10.5 |
| S.aureus EPS (wfk20A) | SEQ ID NO 18 | 0.02 | 54.0 | 19.0 |
| S.aureus EPS (wfk20A) | SEQ ID NO 18 | 0.2 | 56.7 | 21.7 |

Example 10 Biofilm Growth and Detachment Assay

Staphylococcus aureus 15981 was kindly provided by Iñigo Lasa (Valle et al., Mol Microbiol. 2003 May; 48 (4):1075-87). The strain was grown on trypticase soy agar (TSA) at 37° C. overnight. Next day, a single colony was transferred to 15 ml trypticase soy broth (TSB) and incubated 5 hours at 37° C. under shaking. The culture was diluted 1:100 in TSB+1% glucose and 100 µL of the bacterial suspension was transferred to each well of a 96-well microtiter plates (Thermo Scientific, Nunclon Delta Surface, cat #167008) and incubated 24 hours at 37° C. without shaking. and 100 µL of the bacterial suspension was transferred to each well of a 96-well microtiter plates (Thermo Scientific, Nunclon Delta Surface, cat #167008) and incubated 24 hours at 37° C. without shaking. Supernatant was aspirated and wells were washed with 100 µL of 0.9% sodium chloride and filled with 100 µL of either hard water or 3.3 gr/L non-ionic detergent or 3.3 gr/L model A detergent (composition hard water and non-ionic and model A) containing 0 (control) or 20, 10, 5, 2.5, 1.25, 0.62, 0.31, 0.16, 0.08, 0.04, 0.02 and 0.01 µg/mL of dispersin SEQ ID 18. After incubation at 37° C. for 1 hour, wells were washed with water and stained for 15 min with 100 µL of 0.095% crystal violet solution (SIGMA V5265). Wells were then rinsed twice with 100 µL water, dried and the plates were scanned.

The lowest concentration of each enzyme that could remove the visible formation of biofilm of the S. aureus 15981 organism after 1 hour incubation, in the presence and absence of detergent was determined (see Table 10). All enzymes were assayed per duplicate. The average of the minimal concentration of enzyme that removed the visible formation of S. aureus 15981 from the three assays is listed in Table 10.

TABLE 10

Minimal concentration of enzyme that can remove the visible formation of S. aureus 15981 after 1 hour incubation in either hard water or model A detergent

| Enzyme | Minimal concentration for biofilm removal in hard water µg/mL | Minimal concentration for biofilm removal in non-ionic detergent µg/mL | Minimal concentration for biofilm removal in model A detergent µg/mL |
|---|---|---|---|
| SEQ ID NO 18 | 0.04 | 0.04 | 0.08 |

Example 11 Characterization of Dispersins

Dispersin Activity as a Function of pH

Activity assay: The activity of the dispersin having SEQ ID NO: 3 was measured with 4-Nitrophenyl N-acetyl-β-D-glucosaminide (4-NAG, CAS Number 3459-18-5, CHE00244) as substrate as a function of pH (4-10 in 1-unit increments). The concentrations of substrate and the dispersin having SEQ ID NO: 3 were 5 mM and 10.0 µM, respectively, in all measurements. The dilution buffers comprise: 50 mM MES (CAS Number: 4432-31-9), 50 mM glycine (CAS Number: 56-40-6), 50 mM acetic acid (CAS Number: 64-19-7) adjusted to pH 4-10. The substrate solution (10 mM) was prepared by dissolving 34.23 mg 4-NAG in 10.0 mL water. Dissolution required rigorous vortex mixing and gentle heating. The enzyme concentration was determined by UV-Vis ($\varepsilon_{280} = 57890\ M^{-1}\ cm^{-1}$). The enzyme samples were incubated at the different pH-values in volumes of 200 µL in a thermomixer (in MTP) for 10 min and 500 rpm at 30° C. After 10 min, the MTP was incubated at 95° C. and 500 rpm for 10 min in thermomixer to end the reaction. Then the samples were transferred to ice bath and cooled for 2 min. The samples were added 20 μL 4 M NaOH to deprotonate pNP (induce yellow color). Absorbance at 405 nm was measured for 2 min in 10 sec. intervals. All measurements were produced in triplicates and reference samples were produced for all conditions (buffer instead of enzyme).

Results: The following table display the average absorbance (activity) subtracted the average absorbance of the reference samples measured after 10 min incubation at different pH values. In this case, the greatest activity is obtained at pH 4.

Dispersin Activity as a Function of pH

|  | pH | | | | | | |
| --- | --- | --- | --- | --- | --- | --- | --- |
|  | 4 | 5 | 6 | 7 | 8 | 9 | 10 |
| $A_{405}$ | 0.50 | 0.43 | 0.31 | 0.29 | 0.30 | 0.32 | 0.37 |

Dispersin Stability as a Function of pH and NaCl

Stability assay—differential scanning fluorimetry: The thermal stability of the dispersin having SEQ ID NO: 3 was measured as a function of pH (4, 6, 7, 8, 10) and NaCl concentration (100, 200, and 300 mM). The thermal unfolding was monitored using intrinsic fluorescence utilizing a Prometheus NT.48. The concentrations the dispersin having SEQ ID NO: 3 was 0.2 mg/mL in all measurements. The enzyme concentration was determined by UV-Vis ($\varepsilon_{280}$=57890 M$^{-1}$cm$^{-1}$). The dilution buffers comprise: 50 mM MES (CAS Number: 4432-31-9), 50 mM glycine (CAS Number: 56-40-6), 50 mM acetic acid (CAS Number: 64-19-7) adjusted to pH 4, 6, 7, 8, or 10.

The enzyme samples were prepared by mixing a 5 M NaCl stock, buffer, water (MQ), and enzyme to obtain the desired concentrations. The total volume of each mixture was 100 μL. The samples were loaded in the instrument in duplicates and measured from 20 to 95° C. with temperature ramping of 2.0° C./min.

Results: Melting temperatures ($T_m$-values) were derived from the thermograms using the PR.ThermControl v.2.0.4 software. The following table display the average $T_m$-values obtained at the different conditions:

|  |  | pH | | | | |
| --- | --- | --- | --- | --- | --- | --- |
|  |  | 4 | 6 | 7 | 8 | 10 |
| [NaCl] | 0 | 52.1 | 52.9 | 51.1 | 50.0 | 29.2 |
| mM | 100 | 50.0 | 52.3 | 50.1 | 48.5 | N/A |
|  | 200 | 49.1 | 51.9 | 49.6 | 47.8 | N/A |
|  | 300 | 48.3 | 51.4 | 48.8 | 46.9 | N/A |

Dispersin Activity as a Function of Temperature

Activity assay: The activity of the dispersin having SEQ ID NO: 3 was measured with 4-Nitrophenyl N-acetyl-β-D-glucosaminide (4-NAG, CAS Number 3459-18-5, CHE00244) as substrate at pH 7. The concentrations of substrate and the dispersin having SEQ ID NO: 3 were 1 mM and 5 μM, respectively, in all measurements. The dilution buffer comprises: 50 mM MES (CAS Number: 4432-31-9), 50 mM glycine (CAS Number: 56-40-6), 50 mM acetic acid (CAS Number: 64-19-7), pH 7.

The substrate solution (10 mM) was prepared by dissolving 35.9 mg 4-NAG in 10.482 mL water. Dissolution required rigorous vortex mixing and gentle heating. The enzyme concentration was determined by UV-Vis ($\varepsilon_{280}$=57890 M$^{-1}$cm$^{-1}$). The reaction mixture comprised 23.7 μL enzyme (42.3 μM), 20 μL substrate, and 156.3 μL buffer.

The enzyme samples were incubated in volumes of 200 μL in a thermomixer for 10 min and 500 rpm at 20, 30, 40, 45, 50, 55, 60, or 70° C. After 10 min, the samples were transferred to ice bath and cooled for 2 min. The samples were added 10 μL 4 M NaOH to deprotonate pNP (induce yellow color). 180 μL reaction mixture was transferred to a MT plate and absorbance at 405 nm was measured for 1 min in 10 sec. intervals. All measurements were produced in duplicates and reference samples were produced for all conditions (buffer instead of enzyme).

Results: The following table display the average absorbance (activity) subtracted the average absorbance of the reference samples measured after 10 min incubation at different temperatures. The results demonstrate that the activity increases with increasing temperature until 50° C. Hereafter, the activity rapidly decreases with temperature.

Dispersin Activity as a Function of Temperature

|  | 20° C. | 30° C. | 40° C. | 45° C. | 50° C. | 55° C. | 60° C. | 70° C. |
| --- | --- | --- | --- | --- | --- | --- | --- | --- |
| $A_{405}$ | 0.00 | 0.02 | 0.02 | 0.03 | 0.03 | 0.01 | 0.01 | 0.00 |

What is claimed is:

1. A method of treating a fabric, comprising contacting the fabric with an aqueous solution of a hexosaminidase having β1,6 N-acetylglucosaminidase activity, wherein the fabric comprises a biofilm comprising polymers of N-acetyl-glucosamine (PNAG), wherein
   (a) the amino acid sequence of the hexosaminidase has at least 90% sequence identity to the amino acid sequence of SEQ ID NO: 3, and
   (b) the biofilm is reduced or removed from the fabric.

2. The method of claim 1, wherein the hexosaminidase comprises one or more of the following motifs: GXDE (SEQ ID NO: 12), wherein X is any naturally-occurring amino acid, [EQ][NRSHA][YVFL][AGSTC][IVLF][EAQYN][SN] (SEQ ID NO: 13), [VLIM][LIV]G[GAV]DE[VI][P-SA](SEQ ID NO: 14), or [GK]A[IL][IL][KSR][LQ]L (SEQ ID NO: 15).

3. The method of claim 1, wherein the amino acid sequence of the hexosaminidase has at least 95% sequence identity to the amino acid sequence of SEQ ID NO: 3.

4. The method of claim 1, wherein the amino acid sequence of the hexosaminidase has at least 96% sequence identity to the amino acid sequence of SEQ ID NO: 3.

5. The method of claim 1, wherein the amino acid sequence of the hexosaminidase has at least 97% sequence identity to the amino acid sequence of SEQ ID NO: 3.

6. The method of claim 1, wherein the amino acid sequence of the hexosaminidase has at least 98% sequence identity to the amino acid sequence of SEQ ID NO: 3.

7. The method of claim 1, wherein the amino acid sequence of the hexosaminidase has at least 99% sequence identity to the amino acid sequence of SEQ ID NO: 3.

8. The method of claim 1, wherein the hexosaminidase comprises the amino acid sequence of SEQ ID NO: 3.

9. The method of claim 1, further comprising rinsing and drying the fabric.

10. A method for cleaning or laundering a fabric, comprising
    (a) exposing the fabric to a wash liquor comprising a detergent composition comprising a hexosaminidase having β1,6 N-acetylglucosaminidase activity, wherein the amino acid sequence of the hexosaminidase has at least 90% sequence identity to the amino acid sequence of SEQ ID NO: 3, and wherein the fabric comprises a biofilm comprising polymers of N-acetyl-glucosamine (PNAG); and (b) completing at least one wash cycle;

wherein the biofilm is reduced or removed from the fabric.

11. The method of claim 10, wherein the hexosaminidase comprises one or more of the following motifs: GXDE (SEQ ID NO: 12), wherein X is any naturally-occurring amino acid, [EQ][NRSHA][YVFL][AGSTC][IVLF][EAQYN][SN] (SEQ ID NO: 13), [VLIM][LIV]G[GAV]DE[VI][PSA] (SEQ ID NO: 14), or [GK]A[IL][IL][KSR][LQ]L (SEQ ID NO: 15).

12. The method of claim 10, wherein the amino acid sequence of the hexosaminidase has at least 95% sequence identity to the amino acid sequence of SEQ ID NO: 3.

13. The method of claim 10, wherein the amino acid sequence of the hexosaminidase has at least 96% sequence identity to the amino acid sequence of SEQ ID NO: 3.

14. The method of claim 10, wherein the amino acid sequence of the hexosaminidase has at least 97% sequence identity to the amino acid sequence of SEQ ID NO: 3.

15. The method of claim 10, wherein the amino acid sequence of the hexosaminidase has at least 98% sequence identity to the amino acid sequence of SEQ ID NO: 3.

16. The method of claim 10, wherein the amino acid sequence of the hexosaminidase has at least 99% sequence identity to the amino acid sequence of SEQ ID NO: 3.

17. The method of claim 10, wherein the hexosaminidase comprises the amino acid sequence of SEQ ID NO: 3.

18. The method of claim 10, further comprising rinsing and drying the fabric.

19. The method of claim 10, wherein the hexosaminidase is present in the detergent composition in an amount of 0.01 to 100 mg/mL.

20. The method of claim 10, wherein the hexosaminidase is present in the detergent composition in an amount of 0.01 to 10 mg/mL.

\* \* \* \* \*

SEQUENCE LISTING

<160> NUMBER OF SEQ ID NOS: 32

<210> SEQ ID NO 1
<211> LENGTH: 1086
<212> TYPE: DNA
<213> ORGANISM: Lactobacillus paraplantarum
<220> FEATURE:
<221> NAME/KEY: CDS
<222> LOCATION: (1)..(1083)
<220> FEATURE:
<221> NAME/KEY: sig_peptide
<222> LOCATION: (1)..(90)
<220> FEATURE:
<221> NAME/KEY: mat_peptide
<222> LOCATION: (91)..(1083)

<400> SEQUENCE: 1

```
atg aag tac cga cat tac ttt aca caa cta tta ata ttt att agc ccg      48
Met Lys Tyr Arg His Tyr Phe Thr Gln Leu Leu Ile Phe Ile Ser Pro
-30             -25                 -20                 -15 ctg att ctt ctt tgc ttc agc cag ccc cgt acg gca act gcc aat tca      96
Leu Ile Leu Leu Cys Phe Ser Gln Pro Arg Thr Ala Thr Ala Asn Ser
            -10                 -5                  -1   1 tca aca ttg aat act agt caa ggg gtc atg tta gat tta ggc cgc cat     144
Ser Thr Leu Asn Thr Ser Gln Gly Val Met Leu Asp Leu Gly Arg His
        5                   10                  15 ccg tta gat gaa act gca att aaa gcc gtc att agt gct gct gcc gaa     192
Pro Leu Asp Glu Thr Ala Ile Lys Ala Val Ile Ser Ala Ala Ala Glu
        20                  25                  30 caa cac atg caa tac gtc gaa cta cac tta tca gat aac gaa cat cta     240
Gln His Met Gln Tyr Val Glu Leu His Leu Ser Asp Asn Glu His Leu
35              40                  45                  50 tgc ttt caa tcg gct tat tta ggt aat gcc gca tcg gca acc gta tta     288
Cys Phe Gln Ser Ala Tyr Leu Gly Asn Ala Ala Ser Ala Thr Val Leu
                55                  60                  65 tcg gcg acg act tta gaa cag cta gtt gct tat gcc aat cag ttg aac     336
Ser Ala Thr Thr Leu Glu Gln Leu Val Ala Tyr Ala Asn Gln Leu Asn
            70                  75                  80 att gaa cta gtt cct gat gtt gac ctt ccc tcg cac gcg gga gcc att     384
Ile Glu Leu Val Pro Asp Val Asp Leu Pro Ser His Ala Gly Ala Ile
        85                  90                  95 tta cgc caa ttg caa caa act cat ccc gat att tac aat acc gtt aag     432
Leu Arg Gln Leu Gln Gln Thr His Pro Asp Ile Tyr Asn Thr Val Lys
        100                 105                 110 ttg gat gac gaa acc atc gac tat act aaa ccg gca gca atc agt ctc     480
Leu Asp Asp Glu Thr Ile Asp Tyr Thr Lys Pro Ala Ala Ile Ser Leu
115             120                 125                 130 gct acc aca ctt tat ggc gag ctc gat gct agt ttt aac aat caa agc     528
Ala Thr Thr Leu Tyr Gly Glu Leu Asp Ala Ser Phe Asn Asn Gln Ser
                135                 140                 145 cag cac gat ttg atg ctc ggc gct gat gag gtt cct ggc agc gct agc     576
Gln His Asp Leu Met Leu Gly Ala Asp Glu Val Pro Gly Ser Ala Ser
            150                 155                 160 gcc tat atc gaa ctg acc acc ttt atc aat cag gtc agt cga ttt caa     624
Ala Tyr Ile Glu Leu Thr Thr Phe Ile Asn Gln Val Ser Arg Phe Gln
        165                 170                 175 aat caa cac ggc ttc aac act agt att tgg aat gat tcg cta tta aaa     672
Asn Gln His Gly Phe Asn Thr Ser Ile Trp Asn Asp Ser Leu Leu Lys
        180                 185                 190 aat gaa ctc act cgt ctg gat tca aac att aca atc aat tac tgg tca     720
Asn Glu Leu Thr Arg Leu Asp Ser Asn Ile Thr Ile Asn Tyr Trp Ser
195             200                 205                 210 caa tct ggt aac aat acc gat gtg gct atc att gcc gac cgc tat gcc     768
Gln Ser Gly Asn Asn Thr Asp Val Ala Ile Ile Ala Asp Arg Tyr Ala
                215                 220                 225 aac cgt gta tcc gtt ccc gac att tta gcc tct ggg cat ccg atc gtg     816
Asn Arg Val Ser Val Pro Asp Ile Leu Ala Ser Gly His Pro Ile Val
            230                 235                 240 aac tgt aat agt tat gcg acc tat tat caa atc aaa aat att ggc aat     864
Asn Cys Asn Ser Tyr Ala Thr Tyr Tyr Gln Ile Lys Asn Ile Gly Asn
        245                 250                 255 gtc aat gat gac gat tac ttt att aat tat ctt aat cac acc ttt cgc     912
Val Asn Asp Asp Asp Tyr Phe Ile Asn Tyr Leu Asn His Thr Phe Arg
        260                 265                 270 ccg aat atc ttt aac gaa att gac acc aat ggg cat aat cag gat tgg     960
Pro Asn Ile Phe Asn Glu Ile Asp Thr Asn Gly His Asn Gln Asp Trp
```

```
                275                 280                 285                 290
acc att gaa gat ggc gtc aca act aac ggt atc tta gtt agc ttg tgg              1008
Thr Ile Glu Asp Gly Val Thr Thr Asn Gly Ile Leu Val Ser Leu Trp
                    295                 300                 305 ggg gcc gat tca gag cat gtt aca cca act gcc atc gtc aat ttc att              1056
Gly Ala Asp Ser Glu His Val Thr Pro Thr Ala Ile Val Asn Phe Ile
                310                 315                 320 aaa cgt atg acg att cca cgg tca ttt taa                                      1086
Lys Arg Met Thr Ile Pro Arg Ser Phe
            325                 330

<210> SEQ ID NO 2
<211> LENGTH: 361
<212> TYPE: PRT
<213> ORGANISM: Lactobacillus paraplantarum

<400> SEQUENCE: 2

Met Lys Tyr Arg His Tyr Phe Thr Gln Leu Leu Ile Phe Ile Ser Pro
-30                 -25                 -20                 -15

Leu Ile Leu Leu Cys Phe Ser Gln Pro Arg Thr Ala Thr Ala Asn Ser
                -10                 -5                  -1  1

Ser Thr Leu Asn Thr Ser Gln Gly Val Met Leu Asp Leu Gly Arg His
            5                   10                  15

Pro Leu Asp Glu Thr Ala Ile Lys Ala Val Ile Ser Ala Ala Ala Glu
        20                  25                  30

Gln His Met Gln Tyr Val Glu Leu His Leu Ser Asp Asn Glu His Leu
35                  40                  45                  50

Cys Phe Gln Ser Ala Tyr Leu Gly Asn Ala Ala Ser Ala Thr Val Leu
                55                  60                  65

Ser Ala Thr Thr Leu Glu Gln Leu Val Ala Tyr Ala Asn Gln Leu Asn
            70                  75                  80

Ile Glu Leu Val Pro Asp Val Asp Leu Pro Ser His Ala Gly Ala Ile
        85                  90                  95

Leu Arg Gln Leu Gln Gln Thr His Pro Asp Ile Tyr Asn Thr Val Lys
        100                 105                 110

Leu Asp Asp Glu Thr Ile Asp Tyr Thr Lys Pro Ala Ala Ile Ser Leu
115                 120                 125                 130

Ala Thr Thr Leu Tyr Gly Glu Leu Asp Ala Ser Phe Asn Asn Gln Ser
            135                 140                 145

Gln His Asp Leu Met Leu Gly Ala Asp Glu Val Pro Gly Ser Ala Ser
        150                 155                 160

Ala Tyr Ile Glu Leu Thr Thr Phe Ile Asn Gln Val Ser Arg Phe Gln
        165                 170                 175

Asn Gln His Gly Phe Asn Thr Ser Ile Trp Asn Asp Ser Leu Leu Lys
        180                 185                 190

Asn Glu Leu Thr Arg Leu Asp Ser Asn Ile Thr Ile Asn Tyr Trp Ser
195                 200                 205                 210

Gln Ser Gly Asn Asn Thr Asp Val Ala Ile Ala Asp Arg Tyr Ala
            215                 220                 225

Asn Arg Val Ser Val Pro Asp Ile Leu Ala Ser Gly His Pro Ile Val
        230                 235                 240

Asn Cys Asn Ser Tyr Ala Thr Tyr Tyr Gln Ile Lys Asn Ile Gly Asn
        245                 250                 255

Val Asn Asp Asp Asp Tyr Phe Ile Asn Tyr Leu Asn His Thr Phe Arg
        260                 265                 270
```

```
Pro Asn Ile Phe Asn Glu Ile Asp Thr Asn Gly His Asn Gln Asp Trp
275                 280                 285                 290

Thr Ile Glu Asp Gly Val Thr Thr Asn Gly Ile Leu Val Ser Leu Trp
                295                 300                 305

Gly Ala Asp Ser Glu His Val Thr Pro Thr Ala Ile Val Asn Phe Ile
                310                 315                 320

Lys Arg Met Thr Ile Pro Arg Ser Phe
                325                 330

<210> SEQ ID NO 3
<211> LENGTH: 331
<212> TYPE: PRT
<213> ORGANISM: Lactobacillus paraplantarum

<400> SEQUENCE: 3

Asn Ser Ser Thr Leu Asn Thr Ser Gln Gly Val Met Leu Asp Leu Gly
1               5                   10                  15

Arg His Pro Leu Asp Glu Thr Ala Ile Lys Ala Val Ile Ser Ala Ala
                20                  25                  30

Ala Glu Gln His Met Gln Tyr Val Glu Leu His Leu Ser Asp Asn Glu
            35                  40                  45

His Leu Cys Phe Gln Ser Ala Tyr Leu Gly Asn Ala Ala Ser Ala Thr
    50                  55                  60

Val Leu Ser Ala Thr Thr Leu Glu Gln Leu Val Ala Tyr Ala Asn Gln
65                  70                  75                  80

Leu Asn Ile Glu Leu Val Pro Asp Val Asp Leu Pro Ser His Ala Gly
                85                  90                  95

Ala Ile Leu Arg Gln Leu Gln Gln Thr His Pro Asp Ile Tyr Asn Thr
            100                 105                 110

Val Lys Leu Asp Asp Glu Thr Ile Asp Tyr Thr Lys Pro Ala Ala Ile
        115                 120                 125

Ser Leu Ala Thr Thr Leu Tyr Gly Glu Leu Asp Ala Ser Phe Asn Asn
130                 135                 140

Gln Ser Gln His Asp Leu Met Leu Gly Ala Asp Glu Val Pro Gly Ser
145                 150                 155                 160

Ala Ser Ala Tyr Ile Glu Leu Thr Thr Phe Ile Asn Gln Val Ser Arg
                165                 170                 175

Phe Gln Asn Gln His Gly Phe Asn Thr Ser Ile Trp Asn Asp Ser Leu
            180                 185                 190

Leu Lys Asn Glu Leu Thr Arg Leu Asp Ser Asn Ile Thr Ile Asn Tyr
        195                 200                 205

Trp Ser Gln Ser Gly Asn Asn Thr Asp Val Ala Ile Ile Ala Asp Arg
210                 215                 220

Tyr Ala Asn Arg Val Ser Val Pro Asp Ile Leu Ala Ser Gly His Pro
225                 230                 235                 240

Ile Val Asn Cys Asn Ser Tyr Ala Thr Tyr Tyr Gln Ile Lys Asn Ile
                245                 250                 255

Gly Asn Val Asn Asp Asp Tyr Phe Ile Asn Tyr Leu Asn His Thr
            260                 265                 270

Phe Arg Pro Asn Ile Phe Asn Glu Ile Asp Thr Asn Gly His Asn Gln
        275                 280                 285

Asp Trp Thr Ile Glu Asp Gly Val Thr Thr Asn Gly Ile Leu Val Ser
290                 295                 300

Leu Trp Gly Ala Asp Ser Glu His Val Thr Pro Thr Ala Ile Val Asn
305                 310                 315                 320
```

```
               Phe Ile Lys Arg Met Thr Ile Pro Arg Ser Phe
                               325                 330
```

```
<210> SEQ ID NO 4
<211> LENGTH: 1146
<212> TYPE: DNA
<213> ORGANISM: Lactobacillus apinorum
<220> FEATURE:
<221> NAME/KEY: CDS
<222> LOCATION: (1)..(1143)
<220> FEATURE:
<221> NAME/KEY: sig_peptide
<222> LOCATION: (1)..(84)
<220> FEATURE:
<221> NAME/KEY: mat_peptide
<222> LOCATION: (85)..(1143)

<400> SEQUENCE: 4
```

| | | |
|---|---|---|
| atg aga aat aaa cga ttt ata atc gtt gga atg ata ttg ttt tta gtc<br>Met Arg Asn Lys Arg Phe Ile Ile Val Gly Met Ile Leu Phe Leu Val<br>           -25                 -20                       -15 | | 48 |
| tta atg ttt ata caa tta ggc agt tta gcg aaa aag aca ctt gcc gat<br>Leu Met Phe Ile Gln Leu Gly Ser Leu Ala Lys Lys Thr Leu Ala Asp<br>        -10                 -5                   -1 1 | | 96 |
| aca agt aac gat acc aaa aga att ggt cta tca tta gat tgt tcc aga<br>Thr Ser Asn Asp Thr Lys Arg Ile Gly Leu Ser Leu Asp Cys Ser Arg<br>5                  10                 15                 20 | | 144 |
| aca tat tat tct cct tct aca atc aaa aag tat ata gat tta tta aag<br>Thr Tyr Tyr Ser Pro Ser Thr Ile Lys Lys Tyr Ile Asp Leu Leu Lys<br>               25                     30                   35 | | 192 |
| aaa gat cat ggt aca tat ctt caa tta cac tta aat gac aat gaa aga<br>Lys Asp His Gly Thr Tyr Leu Gln Leu His Leu Asn Asp Asn Glu Arg<br>               40                     45                   50 | | 240 |
| tat ggt gtt gaa agt tca acg tta gga caa aca acg caa aac gct aca<br>Tyr Gly Val Glu Ser Ser Thr Leu Gly Gln Thr Thr Gln Asn Ala Thr<br>        55                 60                 65 | | 288 |
| ctt aaa gat ggt gtt tat tac aat aat aaa aca cac tta gca ttt tta<br>Leu Lys Asp Gly Val Tyr Tyr Asn Asn Lys Thr His Leu Ala Phe Leu<br>70                 75                 80 | | 336 |
| agt aaa aat caa tta tta gat gta att caa tac ggt tac act cat gga<br>Ser Lys Asn Gln Leu Leu Asp Val Ile Gln Tyr Gly Tyr Thr His Gly<br>85                  90                 95                  100 | | 384 |
| att gaa gta att cca gaa ata gac tta cct gga cat gct caa tct ata<br>Ile Glu Val Ile Pro Glu Ile Asp Leu Pro Gly His Ala Gln Ser Ile<br>               105                    110                 115 | | 432 |
| ttt aag ctt ctt tca tat act tca gaa gga aag aaa cta gtt aaa gag<br>Phe Lys Leu Leu Ser Tyr Thr Ser Glu Gly Lys Lys Leu Val Lys Glu<br>               120                    125                 130 | | 480 |
| tta gaa aat aaa gat ggt tac aat gaa atg tac tac aac aaa caa gct<br>Leu Glu Asn Lys Asp Gly Tyr Asn Glu Met Tyr Tyr Asn Lys Gln Ala<br>           135                    140                 145 | | 528 |
| acg att gat ttt tca aaa aag ctt tta agt gaa tat gtt ggc atg ctt<br>Thr Ile Asp Phe Ser Lys Lys Leu Leu Ser Glu Tyr Val Gly Met Leu<br>        150                    155                    160 | | 576 |
| ccc agt gga tac cac att att gta ggt gcc gat gaa ata act att agt<br>Pro Ser Gly Tyr His Ile Ile Val Gly Ala Asp Glu Ile Thr Ile Ser<br>165                  170                 175                  180 | | 624 |
| gat aaa agt gat caa gaa gcc gtt gtt aag tat att aat gcc att gat<br>Asp Lys Ser Asp Gln Glu Ala Val Val Lys Tyr Ile Asn Ala Ile Asp<br>               185                    190                 195 | | 672 |
| gat tat gtt aat gct aat cat tta aaa ctt gaa atg tgg aat gat agt<br>Asp Tyr Val Asn Ala Asn His Leu Lys Leu Glu Met Trp Asn Asp Ser | | 720 |

```
                        200                     205                     210
ttt cat aag gcg gtt tta agt aaa tat cat aaa gat att tta att aat        768
Phe His Lys Ala Val Leu Ser Lys Tyr His Lys Asp Ile Leu Ile Asn
        215                     220                     225 tac tgg agt tta aca ggt gaa gtt agc tca agt aag gat aga aaa gac        816
Tyr Trp Ser Leu Thr Gly Glu Val Ser Ser Ser Lys Asp Arg Lys Asp
    230                     235                     240 aac atc agg atg aga gca aca ctt cct gaa tta aat aag gct ggt ttt        864
Asn Ile Arg Met Arg Ala Thr Leu Pro Glu Leu Asn Lys Ala Gly Phe
245                     250                     255                 260 aag aca att aac tac aat agt tat tat cta tat atg att aca gat cca        912
Lys Thr Ile Asn Tyr Asn Ser Tyr Tyr Leu Tyr Met Ile Thr Asp Pro
                265                     270                     275 aca tca ttt acc aat gaa tct aag aaa att tgg act tcc gag ttt aaa        960
Thr Ser Phe Thr Asn Glu Ser Lys Lys Ile Trp Thr Ser Glu Phe Lys
            280                     285                     290 aaa tgg aaa atg aat atg tgg aat gat gaa tct aca aaa gat atc aca       1008
Lys Trp Lys Met Asn Met Trp Asn Asp Glu Ser Thr Lys Asp Ile Thr
        295                     300                     305 aag agc gcc aat aat att ggt gct gcc ata tca ata tgg ggt gaa tat       1056
Lys Ser Ala Asn Asn Ile Gly Ala Ala Ile Ser Ile Trp Gly Glu Tyr
    310                     315                     320 cca aat caa tat act ggt gat caa aca tat aat aag aca tat tat tac       1104
Pro Asn Gln Tyr Thr Gly Asp Gln Thr Tyr Asn Lys Thr Tyr Tyr Tyr
325                     330                     335                 340 gtt gat acg ttt tta aag gcc cag gat aaa ttt act aag taa               1146
Val Asp Thr Phe Leu Lys Ala Gln Asp Lys Phe Thr Lys
                345                     350
```

<210> SEQ ID NO 5
<211> LENGTH: 381
<212> TYPE: PRT
<213> ORGANISM: Lactobacillus apinorum

<400> SEQUENCE: 5

```
Met Arg Asn Lys Arg Phe Ile Ile Val Gly Met Ile Leu Phe Leu Val
            -25                     -20                     -15

Leu Met Phe Ile Gln Leu Gly Ser Leu Ala Lys Lys Thr Leu Ala Asp
        -10                      -5                  -1   1

Thr Ser Asn Asp Thr Lys Arg Ile Gly Leu Ser Leu Asp Cys Ser Arg
  5                      10                      15                  20

Thr Tyr Tyr Ser Pro Ser Thr Ile Lys Lys Tyr Ile Asp Leu Leu Lys
                    25                      30                      35

Lys Asp His Gly Thr Tyr Leu Gln Leu His Leu Asn Asp Asn Glu Arg
                40                      45                      50

Tyr Gly Val Glu Ser Ser Thr Leu Gly Gln Thr Thr Gln Asn Ala Thr
            55                      60                      65

Leu Lys Asp Gly Val Tyr Tyr Asn Asn Lys Thr His Leu Ala Phe Leu
        70                      75                      80

Ser Lys Asn Gln Leu Leu Asp Val Ile Gln Tyr Gly Tyr Thr His Gly
 85                      90                      95                     100

Ile Glu Val Ile Pro Glu Ile Asp Leu Pro Gly His Ala Gln Ser Ile
                    105                     110                     115

Phe Lys Leu Leu Ser Tyr Thr Ser Glu Gly Lys Lys Leu Val Lys Glu
                120                     125                     130

Leu Glu Asn Lys Asp Gly Tyr Asn Glu Met Tyr Tyr Asn Lys Gln Ala
            135                     140                     145
```

Thr Ile Asp Phe Ser Lys Lys Leu Leu Ser Glu Tyr Val Gly Met Leu
            150                 155                 160

Pro Ser Gly Tyr His Ile Ile Val Gly Ala Asp Glu Ile Thr Ile Ser
165                 170                 175                 180

Asp Lys Ser Asp Gln Glu Ala Val Val Lys Tyr Ile Asn Ala Ile Asp
                185                 190                 195

Asp Tyr Val Asn Ala Asn His Leu Lys Leu Glu Met Trp Asn Asp Ser
                200                 205                 210

Phe His Lys Ala Val Leu Ser Lys Tyr His Lys Asp Ile Leu Ile Asn
            215                 220                 225

Tyr Trp Ser Leu Thr Gly Glu Val Ser Ser Lys Asp Arg Lys Asp
230                 235                 240

Asn Ile Arg Met Arg Ala Thr Leu Pro Glu Leu Asn Lys Ala Gly Phe
245                 250                 255                 260

Lys Thr Ile Asn Tyr Asn Ser Tyr Tyr Leu Tyr Met Ile Thr Asp Pro
                265                 270                 275

Thr Ser Phe Thr Asn Glu Ser Lys Lys Ile Trp Thr Ser Glu Phe Lys
            280                 285                 290

Lys Trp Lys Met Asn Met Trp Asn Asp Glu Ser Thr Lys Asp Ile Thr
            295                 300                 305

Lys Ser Ala Asn Asn Ile Gly Ala Ala Ile Ser Ile Trp Gly Glu Tyr
310                 315                 320

Pro Asn Gln Tyr Thr Gly Asp Gln Thr Tyr Asn Lys Thr Tyr Tyr
325                 330                 335                 340

Val Asp Thr Phe Leu Lys Ala Gln Asp Lys Phe Thr Lys
                345                 350

<210> SEQ ID NO 6
<211> LENGTH: 353
<212> TYPE: PRT
<213> ORGANISM: Lactobacillus apinorum

<400> SEQUENCE: 6

Thr Leu Ala Asp Thr Ser Asn Asp Thr Lys Arg Ile Gly Leu Ser Leu
1               5                   10                  15

Asp Cys Ser Arg Thr Tyr Tyr Ser Pro Ser Thr Ile Lys Lys Tyr Ile
                20                  25                  30

Asp Leu Leu Lys Lys Asp His Gly Thr Tyr Leu Gln Leu His Leu Asn
            35                  40                  45

Asp Asn Glu Arg Tyr Gly Val Glu Ser Ser Thr Leu Gly Gln Thr Thr
        50                  55                  60

Gln Asn Ala Thr Leu Lys Asp Gly Val Tyr Tyr Asn Asn Lys Thr His
65                  70                  75                  80

Leu Ala Phe Leu Ser Lys Asn Gln Leu Leu Asp Val Ile Gln Tyr Gly
                85                  90                  95

Tyr Thr His Gly Ile Glu Val Ile Pro Glu Ile Asp Leu Pro Gly His
                100                 105                 110

Ala Gln Ser Ile Phe Lys Leu Leu Ser Tyr Thr Ser Glu Gly Lys Lys
            115                 120                 125

Leu Val Lys Glu Leu Glu Asn Lys Asp Gly Tyr Asn Glu Met Tyr Tyr
        130                 135                 140

Asn Lys Gln Ala Thr Ile Asp Phe Ser Lys Lys Leu Leu Ser Glu Tyr
145                 150                 155                 160

Val Gly Met Leu Pro Ser Gly Tyr His Ile Ile Val Gly Ala Asp Glu
                165                 170                 175

```
Ile Thr Ile Ser Asp Lys Ser Asp Gln Glu Ala Val Val Lys Tyr Ile
            180                 185                 190
Asn Ala Ile Asp Asp Tyr Val Asn Ala Asn His Leu Lys Leu Glu Met
        195                 200                 205
Trp Asn Asp Ser Phe His Lys Ala Val Leu Ser Lys Tyr His Lys Asp
210                 215                 220
Ile Leu Ile Asn Tyr Trp Ser Leu Thr Gly Glu Val Ser Ser Ser Lys
225                 230                 235                 240
Asp Arg Lys Asp Asn Ile Arg Met Arg Ala Thr Leu Pro Glu Leu Asn
                245                 250                 255
Lys Ala Gly Phe Lys Thr Ile Asn Tyr Asn Ser Tyr Tyr Leu Tyr Met
            260                 265                 270
Ile Thr Asp Pro Thr Ser Phe Thr Asn Glu Ser Lys Lys Ile Trp Thr
        275                 280                 285
Ser Glu Phe Lys Lys Trp Lys Met Asn Met Trp Asn Asp Glu Ser Thr
290                 295                 300
Lys Asp Ile Thr Lys Ser Ala Asn Asn Ile Gly Ala Ala Ile Ser Ile
305                 310                 315                 320
Trp Gly Glu Tyr Pro Asn Gln Tyr Thr Gly Asp Gln Thr Tyr Asn Lys
                325                 330                 335
Thr Tyr Tyr Tyr Val Asp Thr Phe Leu Lys Ala Gln Asp Lys Phe Thr
            340                 345                 350
Lys

<210> SEQ ID NO 7
<211> LENGTH: 1086
<212> TYPE: DNA
<213> ORGANISM: Lactobacillus paraplantarum
<220> FEATURE:
<221> NAME/KEY: CDS
<222> LOCATION: (1)..(1083)
<220> FEATURE:
<221> NAME/KEY: sig_peptide
<222> LOCATION: (1)..(90)
<220> FEATURE:
<221> NAME/KEY: mat_peptide
<222> LOCATION: (91)..(1083)

<400> SEQUENCE: 7 atg aag tgc cga cat tac ttt aca caa cta tta ata ttt att agc ccg      48
Met Lys Cys Arg His Tyr Phe Thr Gln Leu Leu Ile Phe Ile Ser Pro
-30                 -25                 -20                 -15 ctg att ctt ctt tgc ttc agc cag ccc cgt acg gca act gcc aat tca      96
Leu Ile Leu Leu Cys Phe Ser Gln Pro Arg Thr Ala Thr Ala Asn Ser
                -10                 -5                  -1  1 tca aca ttg aat act agt caa ggg gtc atg tta gat tta ggt cgc cat     144
Ser Thr Leu Asn Thr Ser Gln Gly Val Met Leu Asp Leu Gly Arg His
            5                   10                  15 ccg tta gat gaa act gca att aaa gcc gtc att agt gct gct gcc gaa     192
Pro Leu Asp Glu Thr Ala Ile Lys Ala Val Ile Ser Ala Ala Ala Glu
        20                  25                  30 caa cac atg caa tac gtc gaa cta cac tta tca gat aac gaa cat cta     240
Gln His Met Gln Tyr Val Glu Leu His Leu Ser Asp Asn Glu His Leu
35                  40                  45                  50 tgc ttt caa tcg gct tat tta ggt aat gcc gca tcg gca acc gta tta     288
Cys Phe Gln Ser Ala Tyr Leu Gly Asn Ala Ala Ser Ala Thr Val Leu
                55                  60                  65 tcg gca acg act tta gaa cag cta gtt gct tat gcc aat cag ttg aac     336
Ser Ala Thr Thr Leu Glu Gln Leu Val Ala Tyr Ala Asn Gln Leu Asn
```

```
                      70                  75                  80
att gaa cta gtt cct gat gtt gac ctt ccc tcg cac gcg gga gcc att      384
Ile Glu Leu Val Pro Asp Val Asp Leu Pro Ser His Ala Gly Ala Ile
         85                  90                  95 tta cgc caa ttg caa caa act cat ccc gat att tac aat acc gtt aag      432
Leu Arg Gln Leu Gln Gln Thr His Pro Asp Ile Tyr Asn Thr Val Lys
100                 105                 110 ttg gat gac gaa acc atc gac tat act aaa ccg gca gca gtc agt ctc      480
Leu Asp Asp Glu Thr Ile Asp Tyr Thr Lys Pro Ala Ala Val Ser Leu
115                 120                 125                 130 gct acc aca ctt tat ggc gag ctc gat gct agt ttt aac aat caa agc      528
Ala Thr Thr Leu Tyr Gly Glu Leu Asp Ala Ser Phe Asn Asn Gln Ser
            135                 140                 145 cag cac gat ttg atg ctc ggc gct gat gag gtt tct ggc agc gct agc      576
Gln His Asp Leu Met Leu Gly Ala Asp Glu Val Ser Gly Ser Ala Ser
            150                 155                 160 gcc tat atc gaa ctg acc acc ttt atc aat cag gtc agt cga ttt caa      624
Ala Tyr Ile Glu Leu Thr Thr Phe Ile Asn Gln Val Ser Arg Phe Gln
            165                 170                 175 aat caa aac ggc ttc aac act agt att tgg aat gat tcg cta tta aaa      672
Asn Gln Asn Gly Phe Asn Thr Ser Ile Trp Asn Asp Ser Leu Leu Lys
180                 185                 190 aat gaa ctc aat cgt ctg gat tca aac att aca atc aat tac tgg tca      720
Asn Glu Leu Asn Arg Leu Asp Ser Asn Ile Thr Ile Asn Tyr Trp Ser
195                 200                 205                 210 caa tct ggt aac aat acc gat gcg gct atc att gcc gac cgc tat gcc      768
Gln Ser Gly Asn Asn Thr Asp Ala Ala Ile Ile Ala Asp Arg Tyr Ala
            215                 220                 225 aac cgt gca tcc gtt ccc gac att tta gcc tct ggg cat ccg atc gtg      816
Asn Arg Ala Ser Val Pro Asp Ile Leu Ala Ser Gly His Pro Ile Val
            230                 235                 240 aac tgt aat agt tat gcg acc tat tat caa ttc aaa aat att ggc aat      864
Asn Cys Asn Ser Tyr Ala Thr Tyr Tyr Gln Phe Lys Asn Ile Gly Asn
            245                 250                 255 gtc aat gat gac aat tac ttt att aat tat ctt aat cac acc ttt cgc      912
Val Asn Asp Asp Asn Tyr Phe Ile Asn Tyr Leu Asn His Thr Phe Arg
260                 265                 270 ccg aat atc ttt aac gaa att gac acc aac ggg cat aat cag gat tgg      960
Pro Asn Ile Phe Asn Glu Ile Asp Thr Asn Gly His Asn Gln Asp Trp
275                 280                 285                 290 acc att gaa gat ggc gtc aca act aac ggt atc tta gtt agc ttg tgg     1008
Thr Ile Glu Asp Gly Val Thr Thr Asn Gly Ile Leu Val Ser Leu Trp
            295                 300                 305 ggg gcc gat tca gag cat gtt aca cca act gct att gtc aat ttc att     1056
Gly Ala Asp Ser Glu His Val Thr Pro Thr Ala Ile Val Asn Phe Ile
            310                 315                 320 aaa cgt atg gcg att ccc cgg tca ttt taa                             1086
Lys Arg Met Ala Ile Pro Arg Ser Phe
            325                 330

<210> SEQ ID NO 8
<211> LENGTH: 361
<212> TYPE: PRT
<213> ORGANISM: Lactobacillus paraplantarum

<400> SEQUENCE: 8

Met Lys Cys Arg His Tyr Phe Thr Gln Leu Leu Ile Phe Ile Ser Pro
-30                 -25                 -20                 -15

Leu Ile Leu Leu Cys Phe Ser Gln Pro Arg Thr Ala Thr Ala Asn Ser
            -10                 -5                  -1  1
```

```
Ser Thr Leu Asn Thr Ser Gln Gly Val Met Leu Asp Leu Gly Arg His
        5                   10                  15

Pro Leu Asp Glu Thr Ala Ile Lys Ala Val Ile Ser Ala Ala Ala Glu
    20                  25                  30

Gln His Met Gln Tyr Val Glu Leu His Leu Ser Asp Asn Glu His Leu
35                  40                  45                  50

Cys Phe Gln Ser Ala Tyr Leu Gly Asn Ala Ala Ser Ala Thr Val Leu
                55                  60                  65

Ser Ala Thr Thr Leu Glu Gln Leu Val Ala Tyr Ala Asn Gln Leu Asn
            70                  75                  80

Ile Glu Leu Val Pro Asp Val Asp Leu Pro Ser His Ala Gly Ala Ile
        85                  90                  95

Leu Arg Gln Leu Gln Gln Thr His Pro Asp Ile Tyr Asn Thr Val Lys
    100                 105                 110

Leu Asp Asp Glu Thr Ile Asp Tyr Thr Lys Pro Ala Ala Val Ser Leu
115                 120                 125                 130

Ala Thr Thr Leu Tyr Gly Glu Leu Asp Ala Ser Phe Asn Asn Gln Ser
                135                 140                 145

Gln His Asp Leu Met Leu Gly Ala Asp Glu Val Ser Gly Ser Ala Ser
            150                 155                 160

Ala Tyr Ile Glu Leu Thr Thr Phe Ile Asn Gln Val Ser Arg Phe Gln
        165                 170                 175

Asn Gln Asn Gly Phe Asn Thr Ser Ile Trp Asn Asp Ser Leu Leu Lys
    180                 185                 190

Asn Glu Leu Asn Arg Leu Asp Ser Asn Ile Thr Ile Asn Tyr Trp Ser
195                 200                 205                 210

Gln Ser Gly Asn Asn Thr Asp Ala Ala Ile Ala Asp Arg Tyr Ala
                215                 220                 225

Asn Arg Ala Ser Val Pro Asp Ile Leu Ala Ser Gly His Pro Ile Val
    230                 235                 240

Asn Cys Asn Ser Tyr Ala Thr Tyr Tyr Gln Phe Lys Asn Ile Gly Asn
        245                 250                 255

Val Asn Asp Asn Tyr Phe Ile Asn Tyr Leu Asn His Thr Phe Arg
    260                 265                 270

Pro Asn Ile Phe Asn Glu Ile Asp Thr Asn Gly His Asn Gln Asp Trp
275                 280                 285                 290

Thr Ile Glu Asp Gly Val Thr Thr Asn Gly Ile Leu Val Ser Leu Trp
                295                 300                 305

Gly Ala Asp Ser Glu His Val Thr Pro Thr Ala Ile Val Asn Phe Ile
            310                 315                 320

Lys Arg Met Ala Ile Pro Arg Ser Phe
        325                 330

<210> SEQ ID NO 9
<211> LENGTH: 331
<212> TYPE: PRT
<213> ORGANISM: Lactobacillus paraplantarum

<400> SEQUENCE: 9

Asn Ser Ser Thr Leu Asn Thr Ser Gln Gly Val Met Leu Asp Leu Gly
1               5                   10                  15

Arg His Pro Leu Asp Glu Thr Ala Ile Lys Ala Val Ile Ser Ala Ala
                20                  25                  30

Ala Glu Gln His Met Gln Tyr Val Glu Leu His Leu Ser Asp Asn Glu
```

-continued

```
                 35                  40                  45
His Leu Cys Phe Gln Ser Ala Tyr Leu Gly Asn Ala Ala Ser Ala Thr
 50                  55                  60

Val Leu Ser Ala Thr Thr Leu Glu Gln Leu Val Ala Tyr Ala Asn Gln
 65                  70                  75                  80

Leu Asn Ile Glu Leu Val Pro Asp Val Asp Leu Pro Ser His Ala Gly
                 85                  90                  95

Ala Ile Leu Arg Gln Leu Gln Gln Thr His Pro Asp Ile Tyr Asn Thr
                100                 105                 110

Val Lys Leu Asp Asp Glu Thr Ile Asp Tyr Thr Lys Pro Ala Ala Val
                115                 120                 125

Ser Leu Ala Thr Thr Leu Tyr Gly Glu Leu Asp Ala Ser Phe Asn Asn
130                 135                 140

Gln Ser Gln His Asp Leu Met Leu Gly Ala Asp Glu Val Ser Gly Ser
145                 150                 155                 160

Ala Ser Ala Tyr Ile Glu Leu Thr Thr Phe Ile Asn Gln Val Ser Arg
                165                 170                 175

Phe Gln Asn Gln Asn Gly Phe Asn Thr Ser Ile Trp Asn Asp Ser Leu
                180                 185                 190

Leu Lys Asn Glu Leu Asn Arg Leu Asp Ser Asn Ile Thr Ile Asn Tyr
                195                 200                 205

Trp Ser Gln Ser Gly Asn Asn Thr Asp Ala Ala Ile Ile Ala Asp Arg
210                 215                 220

Tyr Ala Asn Arg Ala Ser Val Pro Asp Ile Leu Ala Ser Gly His Pro
225                 230                 235                 240

Ile Val Asn Cys Asn Ser Tyr Ala Thr Tyr Tyr Gln Phe Lys Asn Ile
                245                 250                 255

Gly Asn Val Asn Asp Asp Asn Tyr Phe Ile Asn Tyr Leu Asn His Thr
                260                 265                 270

Phe Arg Pro Asn Ile Phe Asn Glu Ile Asp Thr Asn Gly His Asn Gln
                275                 280                 285

Asp Trp Thr Ile Glu Asp Gly Val Thr Thr Asn Gly Ile Leu Val Ser
290                 295                 300

Leu Trp Gly Ala Asp Ser Glu His Val Thr Pro Thr Ala Ile Val Asn
305                 310                 315                 320

Phe Ile Lys Arg Met Ala Ile Pro Arg Ser Phe
                325                 330

<210> SEQ ID NO 10
<211> LENGTH: 27
<212> TYPE: PRT
<213> ORGANISM: artificial
<220> FEATURE:
<223> OTHER INFORMATION: Signal peptide

<400> SEQUENCE: 10

Met Lys Lys Pro Leu Gly Lys Ile Val Ala Ser Thr Ala Leu Leu Ile
 1               5                  10                  15

Ser Val Ala Phe Ser Ser Ser Ile Ala Ser Ala
                20                  25

<210> SEQ ID NO 11
<211> LENGTH: 8
<212> TYPE: PRT
<213> ORGANISM: artificial
<220> FEATURE:
<223> OTHER INFORMATION: His-tag
```

```
<400> SEQUENCE: 11

His His His His His His Pro Arg
1               5

<210> SEQ ID NO 12
<211> LENGTH: 4
<212> TYPE: PRT
<213> ORGANISM: artificial
<220> FEATURE:
<223> OTHER INFORMATION: motif
<220> FEATURE:
<221> NAME/KEY: misc
<222> LOCATION: (2)..(2)
<223> OTHER INFORMATION: Xaa= any natural occuring amino acids

<400> SEQUENCE: 12

Gly Xaa Asp Glu
1

<210> SEQ ID NO 13
<211> LENGTH: 7
<212> TYPE: PRT
<213> ORGANISM: artificial
<220> FEATURE:
<223> OTHER INFORMATION: motif
<220> FEATURE:
<221> NAME/KEY: misc
<222> LOCATION: (1)..(1)
<223> OTHER INFORMATION: Xaa = E (Glu) or Q (Gln)
<220> FEATURE:
<221> NAME/KEY: misc
<222> LOCATION: (2)..(2)
<223> OTHER INFORMATION: Xaa = N (Asn) or R (Arg) or S (Ser) or H (His)
      or A (Ala)
<220> FEATURE:
<221> NAME/KEY: misc
<222> LOCATION: (3)..(3)
<223> OTHER INFORMATION: Xaa = Y (Tyr) or V (Val) or F (Phe) or L (Leu)
<220> FEATURE:
<221> NAME/KEY: misc
<222> LOCATION: (4)..(4)
<223> OTHER INFORMATION: Xaa = A (Ala) or G (Gly) or S (Ser) or T (Thr)
      or C (Cys)
<220> FEATURE:
<221> NAME/KEY: misc
<222> LOCATION: (5)..(5)
<223> OTHER INFORMATION: Xaa =I (Ile) or V (Val) or L (Leu) or F (Phe)
<220> FEATURE:
<221> NAME/KEY: misc
<222> LOCATION: (6)..(6)
<223> OTHER INFORMATION: Xaa =E (Glu) or A (Ala) or Q (Gln) or Y (Tyr)
      or N (Asn)
<220> FEATURE:
<221> NAME/KEY: misc
<222> LOCATION: (7)..(7)
<223> OTHER INFORMATION: Xaa =S(Ser) or N (Asn)

<400> SEQUENCE: 13

Xaa Xaa Xaa Xaa Xaa Xaa Xaa
1               5

<210> SEQ ID NO 14
<211> LENGTH: 8
<212> TYPE: PRT
<213> ORGANISM: artificial
<220> FEATURE:
<223> OTHER INFORMATION: motif
<220> FEATURE:
<221> NAME/KEY: misc
<222> LOCATION: (1)..(1)
<223> OTHER INFORMATION: Xaa = V(Val) or L (Leu) or I (Ile) or M (Met)
<220> FEATURE:
```

```
<221> NAME/KEY: misc
<222> LOCATION: (2)..(2)
<223> OTHER INFORMATION: Xaa = L (Leu) or I (Ile) or V(Val)
<220> FEATURE:
<221> NAME/KEY: misc
<222> LOCATION: (4)..(4)
<223> OTHER INFORMATION: Xaa = G (Gly) or A (Ala) or V (Val)
<220> FEATURE:
<221> NAME/KEY: misc
<222> LOCATION: (7)..(7)
<223> OTHER INFORMATION: Xaa = V (Val) or I (Ile)
<220> FEATURE:
<221> NAME/KEY: misc
<222> LOCATION: (8)..(8)
<223> OTHER INFORMATION: Xaa = P (Pro) or S (Ser) or A (Ala)

<400> SEQUENCE: 14

Xaa Xaa Gly Xaa Asp Glu Xaa Xaa
1               5

<210> SEQ ID NO 15
<211> LENGTH: 7
<212> TYPE: PRT
<213> ORGANISM: artificial
<220> FEATURE:
<223> OTHER INFORMATION: SEQ ID NO 15
<220> FEATURE:
<221> NAME/KEY: misc
<222> LOCATION: (1)..(1)
<223> OTHER INFORMATION: Xaa = G(Gly) or K (Lys)
<220> FEATURE:
<221> NAME/KEY: misc
<222> LOCATION: (3)..(3)
<223> OTHER INFORMATION: Xaa = I (Ile) or L (Leu)
<220> FEATURE:
<221> NAME/KEY: misc
<222> LOCATION: (4)..(4)
<223> OTHER INFORMATION: Xaa = I (Ile) or L (Leu)
<220> FEATURE:
<221> NAME/KEY: misc
<222> LOCATION: (5)..(5)
<223> OTHER INFORMATION: Xaa = K (Lys) or S (Ser) or R (Arg)
<220> FEATURE:
<221> NAME/KEY: misc
<222> LOCATION: (6)..(6)
<223> OTHER INFORMATION: Xaa = L(Leu) or Q(Gln)

<400> SEQUENCE: 15

Xaa Ala Xaa Xaa Xaa Xaa Leu
1               5

<210> SEQ ID NO 16
<211> LENGTH: 1557
<212> TYPE: DNA
<213> ORGANISM: Strepotcocus merionis
<220> FEATURE:
<221> NAME/KEY: CDS
<222> LOCATION: (1)..(1521)
<220> FEATURE:
<221> NAME/KEY: sig_peptide
<222> LOCATION: (76)..(1521)
<220> FEATURE:
<221> NAME/KEY: mat_peptide
<222> LOCATION: (76)..(1521)
<220> FEATURE:
<221> NAME/KEY: misc_feature
<222> LOCATION: (347)..(347)
<223> OTHER INFORMATION: n is a, c, g, or t
<220> FEATURE:
<221> NAME/KEY: misc_feature
<222> LOCATION: (351)..(351)
<223> OTHER INFORMATION: n is a, c, g, or t
<220> FEATURE:
<221> NAME/KEY: misc_feature
<222> LOCATION: (357)..(357)
```

```
<223> OTHER INFORMATION: n is a, c, g, or t
<220> FEATURE:
<221> NAME/KEY: misc_feature
<222> LOCATION: (372)..(372)
<223> OTHER INFORMATION: n is a, c, g, or t

<400> SEQUENCE: 16 atg cat aag gtt aag gta ctt tta ggg acg gtt ctg ctc ttt tta aca        48
Met His Lys Val Lys Val Leu Leu Gly Thr Val Leu Leu Phe Leu Thr
-25             -20             -15             -10 cta ttg ttg aca gga cag cca gag gca caa gaa cct atc gtt aaa ctc        96
Leu Leu Leu Thr Gly Gln Pro Glu Ala Gln Glu Pro Ile Val Lys Leu
            -5              -1  1               5 tca ggc gga gtg atg gtg gat gtg gct agg aga tat tac tct cta aac       144
Ser Gly Gly Val Met Val Asp Val Ala Arg Arg Tyr Tyr Ser Leu Asn
        10              15              20 tct ctg aaa tct atc att gat act gtt tcg gag aat aaa gga gac ttt       192
Ser Leu Lys Ser Ile Ile Asp Thr Val Ser Glu Asn Lys Gly Asp Phe
    25              30              35 gtt cat ctc cac ttg aca gat gat caa aat tat ggg ttg gag agt cag       240
Val His Leu His Leu Thr Asp Asp Gln Asn Tyr Gly Leu Glu Ser Gln
40              45              50              55 ttt ctc aat caa aca gct tca aat gca atc tat aat caa gat gat caa       288
Phe Leu Asn Gln Thr Ala Ser Asn Ala Ile Tyr Asn Gln Asp Asp Gln
                60              65              70 agc tat act aat cct aat acg aat cga aaa ttt ctc agt tat gga cag       336
Ser Tyr Thr Asn Pro Asn Thr Asn Arg Lys Phe Leu Ser Tyr Gly Gln
            75              80              85 srt yrt hra snr asn thr asn arg ysh srt yrg ygn ttg gct gag ctt       384
Xaa Xaa Xaa Xaa Xaa Xaa Xaa Xaa Xaa Xaa Xaa Leu Ala Glu Leu
        90              95              100 aaa agt tat gcg ggt tca aaa ggc atc cga ttg

```
ctt aat tat aat ggg tat tat cta gct ttt gtt cct aag ccc tca gaa      912
Leu Asn Tyr Asn Gly Tyr Tyr Leu Ala Phe Val Pro Lys Pro Ser Glu
    265                 270                 275 aaa ctt caa tcg gat gcc cta ttt gca gca aat gat att cta aag act      960
Lys Leu Gln Ser Asp Ala Leu Phe Ala Ala Asn Asp Ile Leu Lys Thr
280                 285                 290                 295 tgg aat ctt tcc cag ttt cat atg gat acg ggt gat tcc att aat agt     1008
Trp Asn Leu Ser Gln Phe His Met Asp Thr Gly Asp Ser Ile Asn Ser
                300                 305                 310 tta aag aat gtc att gga gcg gct ttt tcc ata tgg agt gaa gag tca     1056
Leu Lys Asn Val Ile Gly Ala Ala Phe Ser Ile Trp Ser Glu Glu Ser
            315                 320                 325 gct ggt ctg act gac gag gag ata ttt tct gcc atg ggt agt ccg att     1104
Ala Gly Leu Thr Asp Glu Glu Ile Phe Ser Ala Met Gly Ser Pro Ile
        330                 335                 340 cga gct ctt ttg aca gtt atc aat caa gaa aat ata aag aga aac gag     1152
Arg Ala Leu Leu Thr Val Ile Asn Gln Glu Asn Ile Lys Arg Asn Glu
    345                 350                 355 aat acg aca act acc acc acc gag tca atg act gag gct acg aca act     1200
Asn Thr Thr Thr Thr Thr Thr Glu Ser Met Thr Glu Ala Thr Thr Thr
360                 365                 370                 375 att aca act gag ccg aca acc caa tca acc aca gaa agt acg aca act     1248
Ile Thr Thr Glu Pro Thr Thr Gln Ser Thr Thr Glu Ser Thr Thr Thr
                380                 385                 390 act aca acc gag tca acg aca gag act acg aca act gtc aca act gag     1296
Thr Thr Thr Glu Ser Thr Thr Glu Thr Thr Thr Thr Val Thr Thr Glu
            395                 400                 405 tca aca act aag tcg acc aca gaa ggc acg aca gaa aca aca acc cct     1344
Ser Thr Thr Lys Ser Thr Thr Glu Gly Thr Thr Glu Thr Thr Thr Pro
        410                 415                 420 atc cca cca atg cct cag cct aca acg tct cct gag aca agt aca gct     1392
Ile Pro Pro Met Pro Gln Pro Thr Thr Ser Pro Glu Thr Ser Thr Ala
    425                 430                 435 aca cat gca aca acg act aac cca agt aca tca aaa gat ggc aat aaa     1440
Thr His Ala Thr Thr Thr Asn Pro Ser Thr Ser Lys Asp Gly Asn Lys
440                 445                 450                 455 ctg tct aaa tca aaa cgg ata ttg cca agt aca ggt gaa acg att ggt     1488
Leu Ser Lys Ser Lys Arg Ile Leu Pro Ser Thr Gly Glu Thr Ile Gly
                460                 465                 470 gtc ctt tca gta gca gga ttg gcg ctc ttc ttg tttgttgggc ttacatatta   1541
Val Leu Ser Val Ala Gly Leu Ala Leu Phe Leu
            475                 480 ccgtcacaag aagaat                                                   1557

<210> SEQ ID NO 17
<211> LENGTH: 507
<212> TYPE: PRT
<213> ORGANISM: Strepotcocus merionis
<220> FEATURE:
<221> NAME/KEY: misc_feature
<222> LOCATION: (88)..(88)
<223> OTHER INFORMATION: The 'Xaa' at location 88 stands for Gly, Asp,
      Arg, or His.
<220> FEATURE:
<221> NAME/KEY: misc_feature
<222> LOCATION: (89)..(89)
<223> OTHER INFORMATION: The 'Xaa' at location 89 stands for Arg, His,
      Cys, or Tyr.
<220> FEATURE:
<221> NAME/KEY: misc_feature
<222> LOCATION: (90)..(90)
<223> OTHER INFORMATION: The 'Xaa' at location 90 stands for Arg, Lys,
      or Gln.
```

```
<220> FEATURE:
<221> NAME/KEY: misc_feature
<222> LOCATION: (91)..(91)
<223> OTHER INFORMATION: The 'Xaa' at location 91 stands for Glu, Gly,
      Ala, Val, Gln, Arg, Pro, or Leu.
<220> FEATURE:
<221> NAME/KEY: misc_feature
<222> LOCATION: (92)..(92)
<223> OTHER INFORMATION: The 'Xaa' at location 92 stands for Arg, Ser,
      or Thr.
<220> FEATURE:
<221> NAME/KEY: misc_feature
<222> LOCATION: (93)..(93)
<223> OTHER INFORMATION: The 'Xaa' at location 93 stands for Ser, or
      Leu.
<220> FEATURE:
<221> NAME/KEY: misc_feature
<222> LOCATION: (94)..(94)
<223> OTHER INFORMATION: The 'Xaa' at location 94 stands for Arg, Ser,
      or Thr.
<220> FEATURE:
<221> NAME/KEY: misc_feature
<222> LOCATION: (95)..(95)
<223> OTHER INFORMATION: The 'Xaa' at location 95 stands for Arg, or
      Lys.
<220> FEATURE:
<221> NAME/KEY: misc_feature
<222> LOCATION: (96)..(96)
<223> OTHER INFORMATION: The 'Xaa' at location 96 stands for Arg, Pro,
      Cys, or Ser.
<220> FEATURE:
<221> NAME/KEY: misc_feature
<222> LOCATION: (97)..(97)
<223> OTHER INFORMATION: The 'Xaa' at location 97 stands for Gly, Asp,
      Arg, or His.
<220> FEATURE:
<221> NAME/KEY: misc_feature
<222> LOCATION: (98)..(98)
<223> OTHER INFORMATION: The 'Xaa' at location 98 stands for Arg, Gln,
      or Trp.
<220> FEATURE:
<221> NAME/KEY: misc_feature
<222> LOCATION: (99)..(99)
<223> OTHER INFORMATION: The 'Xaa' at location 99 stands for Arg, Trp,
      or Cys.

<400> SEQUENCE: 17

Met His Lys Val Lys Val Leu Gly Thr Val Leu Leu Phe Leu Thr
-25                 -20                 -15                 -10

Leu Leu Leu Thr Gly Gln Pro Glu Ala Gln Glu Pro Ile Val Lys Leu
            -5                  -1  1                   5

Ser Gly Gly Val Met Val Asp Val Ala Arg Arg Tyr Tyr Ser Leu Asn
            10                  15                  20

Ser Leu Lys Ser Ile Ile Asp Thr Val Ser Glu Asn Lys Gly Asp Phe
    25                  30                  35

Val His Leu His Leu Thr Asp Asp Gln Asn Tyr Gly Leu Glu Ser Gln
40                  45                  50                  55

Phe Leu Asn Gln Thr Ala Ser Asn Ala Ile Tyr Asn Gln Asp Asp Gln
                60                  65                  70

Ser Tyr Thr Asn Pro Asn Thr Asn Arg Lys Phe Leu Ser Tyr Gly Gln
            75                  80                  85

Xaa Xaa Xaa Xaa Xaa Xaa Xaa Xaa Xaa Leu Ala Glu Leu
        90                  95                  100

Lys Ser Tyr Ala Gly Ser Lys Gly Ile Arg Leu Ile Pro Glu Ile Asp
        105                 110                 115

Thr Pro Ala His Thr Gly Gly Leu Lys Ala Leu Leu Pro Tyr Ala Glu
120                 125                 130                 135

Pro Ala Val Thr Ser Gln Phe Lys Trp Val Ser Trp Asp Glu Asp Arg
```

```
            140                 145                 150
Gln Leu Asp Leu Asp Ala Ala Thr Thr Gln Glu Ala Val Arg Gln Leu
                155                 160                 165

Tyr Met Glu Leu Val Arg Glu Leu Pro Gly Leu Glu Tyr Ile His Ile
        170                 175                 180

Gly Gly Asp Glu Ile Ser Gly Leu Ile Gln Gly Gln Ser Phe Ile
    185                 190                 195

Ser His Val Asn Gln Leu Cys Asp Tyr Leu Ala Gly Gln Gly Ile Lys
200                 205                 210                 215

Thr Gln Ile Trp Asn Asp Ser Leu Ser Arg Gln Leu Leu Pro Ser Leu
                220                 225                 230

Asn Arg Asn Val Glu Ile Ala Tyr Trp Gly Tyr Leu Pro His Arg Asn
            235                 240                 245

Pro Asp Leu Ala Thr Ala Ser Asp Leu Ser Asp Gln Asp Phe Lys Leu
        250                 255                 260

Leu Asn Tyr Asn Gly Tyr Tyr Leu Ala Phe Val Pro Lys Pro Ser Glu
    265                 270                 275

Lys Leu Gln Ser Asp Ala Leu Phe Ala Ala Asn Asp Ile Leu Lys Thr
280                 285                 290                 295

Trp Asn Leu Ser Gln Phe His Met Asp Thr Gly Asp Ser Ile Asn Ser
                300                 305                 310

Leu Lys Asn Val Ile Gly Ala Ala Phe Ser Ile Trp Ser Glu Glu Ser
            315                 320                 325

Ala Gly Leu Thr Asp Glu Glu Ile Phe Ser Ala Met Gly Ser Pro Ile
        330                 335                 340

Arg Ala Leu Leu Thr Val Ile Asn Gln Glu Asn Ile Lys Arg Asn Glu
    345                 350                 355

Asn Thr Thr Thr Thr Thr Thr Glu Ser Met Thr Glu Ala Thr Thr Thr
360                 365                 370                 375

Ile Thr Thr Glu Pro Thr Thr Gln Ser Thr Thr Glu Ser Thr Thr Thr
                380                 385                 390

Thr Thr Thr Glu Ser Thr Thr Glu Thr Thr Thr Val Thr Thr Glu
            395                 400                 405

Ser Thr Thr Lys Ser Thr Thr Glu Gly Thr Thr Glu Thr Thr Thr Pro
        410                 415                 420

Ile Pro Pro Met Pro Gln Pro Thr Thr Ser Pro Glu Thr Ser Thr Ala
    425                 430                 435

Thr His Ala Thr Thr Thr Asn Pro Ser Thr Ser Lys Asp Gly Asn Lys
440                 445                 450                 455

Leu Ser Lys Ser Lys Arg Ile Leu Pro Ser Thr Gly Glu Thr Ile Gly
                460                 465                 470

Val Leu Ser Val Ala Gly Leu Ala Leu Phe Leu
            475                 480

<210> SEQ ID NO 18
<211> LENGTH: 491
<212> TYPE: PRT
<213> ORGANISM: Steptococcus merionis

<400> SEQUENCE: 18

Met His Lys Val Lys Val Leu Leu Gly Thr Val Leu Leu Phe Leu Thr
1               5                   10                  15

Leu Leu Leu Thr Gly Gln Pro Glu Ala Gln Glu Pro Ile Val Lys Leu
            20                  25                  30
```

```
Ser Gly Gly Val Met Val Asp Val Ala Arg Arg Tyr Tyr Ser Leu Asn
         35                  40                  45

Ser Leu Lys Ser Ile Ile Asp Thr Val Ser Glu Asn Lys Gly Asp Phe
 50                  55                  60

Val His Leu His Leu Thr Asp Asp Gln Asn Tyr Gly Leu Glu Ser Gln
 65                  70                  75                  80

Phe Leu Asn Gln Thr Ala Ser Asn Ala Ile Tyr Asn Gln Asp Asp Gln
                 85                  90                  95

Ser Tyr Thr Asn Pro Asn Thr Asn Arg Lys Phe Leu Ser Tyr Gly Gln
            100                 105                 110

Leu Ala Glu Leu Lys Ser Tyr Ala Gly Ser Lys Gly Ile Arg Leu Ile
        115                 120                 125

Pro Glu Ile Asp Thr Pro Ala His Thr Gly Gly Leu Lys Ala Leu Leu
    130                 135                 140

Pro Tyr Ala Glu Pro Ala Val Thr Ser Gln Phe Lys Trp Val Ser Trp
145                 150                 155                 160

Asp Glu Asp Arg Gln Leu Asp Leu Asp Ala Ala Thr Thr Gln Glu Ala
                165                 170                 175

Val Arg Gln Leu Tyr Met Glu Leu Val Arg Glu Leu Pro Gly Leu Glu
            180                 185                 190

Tyr Ile His Ile Gly Gly Asp Glu Ile Ser Gly Gly Leu Ile Gln Gly
        195                 200                 205

Gln Ser Phe Ile Ser His Val Asn Gln Leu Cys Asp Tyr Leu Ala Gly
    210                 215                 220

Gly Ile Lys Thr Gln Ile Trp Asn Asp Ser Leu Ser Arg Gln Leu
225                 230                 235                 240

Leu Pro Ser Leu Asn Arg Asn Val Glu Ile Ala Tyr Trp Gly Tyr Leu
                245                 250                 255

Pro His Arg Asn Pro Asp Leu Ala Thr Ala Ser Asp Leu Ser Asp Gln
            260                 265                 270

Asp Phe Lys Leu Leu Asn Tyr Asn Gly Tyr Tyr Leu Ala Phe Val Pro
        275                 280                 285

Lys Pro Ser Glu Lys Leu Gln Ser Asp Ala Leu Phe Ala Ala Asn Asp
    290                 295                 300

Ile Leu Lys Thr Trp Asn Leu Ser Gln Phe His Met Asp Thr Gly Asp
305                 310                 315                 320

Ser Ile Asn Ser Leu Lys Asn Val Ile Gly Ala Ala Phe Ser Ile Trp
                325                 330                 335

Ser Glu Glu Ser Ala Gly Leu Thr Asp Glu Glu Ile Phe Ser Ala Met
            340                 345                 350

Gly Ser Pro Ile Arg Ala Leu Leu Thr Val Ile Asn Gln Glu Asn Ile
        355                 360                 365

Ala Thr Thr Thr Ile Thr Thr Glu Pro Thr Thr Gln Ser Thr Thr Glu
    370                 375                 380

Ser Thr Thr Thr Thr Thr Thr Glu Ser Thr Thr Glu Thr Thr Thr Thr
385                 390                 395                 400

Val Thr Thr Glu Ser Thr Thr Lys Ser Thr Thr Glu Gly Thr Thr Glu
                405                 410                 415

Thr Thr Thr Pro Ile Pro Pro Met Pro Gln Pro Thr Thr Ser Pro Glu
            420                 425                 430

Thr Ser Thr Ala Thr His Ala Thr Thr Thr Asn Pro Ser Thr Ser Lys
        435                 440                 445

Asp Gly Asn Lys Leu Ser Lys Ser Lys Arg Ile Leu Pro Ser Thr Gly
```

```
                450                 455                 460
Glu Thr Ile Gly Val Leu Ser Val Ala Gly Leu Ala Leu Phe Leu Phe
465                 470                 475                 480

Val Gly Leu Thr Tyr Tyr Arg His Lys Lys Asn
                485                 490

<210> SEQ ID NO 19
<211> LENGTH: 482
<212> TYPE: PRT
<213> ORGANISM: Streptococcus merionis

<400> SEQUENCE: 19

Gln Glu Pro Ile Val Lys Leu Ser Gly Gly Val Met Val Asp Val Ala
1               5                   10                  15

Arg Arg Tyr Tyr Ser Leu Asn Ser Leu Lys Ser Ile Ile Asp Thr Val
                20                  25                  30

Ser Glu Asn Lys Gly Asp Phe Val His Leu His Leu Thr Asp Asp Gln
            35                  40                  45

Asn Tyr Gly Leu Glu Ser Gln Phe Leu Asn Gln Thr Ala Ser Asn Ala
        50                  55                  60

Ile Tyr Asn Gln Asp Gln Ser Tyr Thr Asn Pro Asn Thr Asn Arg
65                  70                  75                  80

Lys Phe Leu Ser Tyr Gly Gln Leu Ala Glu Leu Lys Ser Tyr Ala Gly
                85                  90                  95

Ser Lys Gly Ile Arg Leu Ile Pro Glu Ile Asp Thr Pro Ala His Thr
            100                 105                 110

Gly Gly Leu Lys Ala Leu Leu Pro Tyr Ala Glu Pro Ala Val Thr Ser
        115                 120                 125

Gln Phe Lys Trp Val Ser Trp Asp Glu Asp Arg Gln Leu Asp Leu Asp
130                 135                 140

Ala Ala Thr Thr Gln Glu Ala Val Arg Gln Leu Tyr Met Glu Leu Val
145                 150                 155                 160

Arg Glu Leu Pro Gly Leu Glu Tyr Ile His Ile Gly Gly Asp Glu Ile
                165                 170                 175

Ser Gly Gly Leu Ile Gln Gly Gln Ser Phe Ile Ser His Val Asn Gln
            180                 185                 190

Leu Cys Asp Tyr Leu Ala Gly Gln Gly Ile Lys Thr Gln Ile Trp Asn
        195                 200                 205

Asp Ser Leu Ser Arg Gln Leu Leu Pro Ser Leu Asn Arg Asn Val Glu
210                 215                 220

Ile Ala Tyr Trp Gly Tyr Leu Pro His Arg Asn Pro Asp Leu Ala Thr
225                 230                 235                 240

Ala Ser Asp Leu Ser Asp Gln Asp Phe Lys Leu Leu Asn Tyr Asn Gly
                245                 250                 255

Tyr Tyr Leu Ala Phe Val Pro Lys Pro Ser Glu Lys Leu Gln Ser Asp
            260                 265                 270

Ala Leu Phe Ala Ala Asn Asp Ile Leu Lys Thr Trp Asn Leu Ser Gln
        275                 280                 285

Phe His Met Asp Thr Gly Asp Ser Ile Asn Ser Leu Lys Asn Val Ile
290                 295                 300

Gly Ala Ala Phe Ser Ile Trp Ser Glu Glu Ser Ala Gly Leu Thr Asp
305                 310                 315                 320

Glu Glu Ile Phe Ser Ala Met Gly Ser Pro Ile Arg Ala Leu Leu Thr
                325                 330                 335
```

-continued

```
Val Ile Asn Gln Glu Asn Ile Lys Arg Asn Glu Asn Thr Thr Thr Thr
            340                 345                 350

Thr Thr Glu Ser Met Thr Glu Ala Thr Thr Thr Ile Thr Thr Glu Pro
    355                 360                 365

Thr Thr Gln Ser Thr Thr Glu Ser Thr Thr Thr Thr Thr Thr Glu Ser
    370                 375                 380

Thr Thr Glu Thr Thr Thr Val Thr Thr Glu Ser Thr Thr Lys Ser
385                 390                 395                 400

Thr Thr Glu Gly Thr Glu Thr Thr Thr Pro Ile Pro Pro Met Pro
            405                 410                 415

Gln Pro Thr Thr Ser Pro Glu Thr Ser Thr Ala Thr His Ala Thr Thr
            420                 425                 430

Thr Asn Pro Ser Thr Ser Lys Asp Gly Asn Lys Leu Ser Lys Ser Lys
            435                 440                 445

Arg Ile Leu Pro Ser Thr Gly Glu Thr Ile Gly Val Leu Ser Val Ala
    450                 455                 460

Gly Leu Ala Leu Phe Leu Phe Val Gly Leu Thr Tyr Tyr Arg His Lys
465                 470                 475                 480

Lys Asn
```

<210> SEQ ID NO 20
<211> LENGTH: 11
<212> TYPE: PRT
<213> ORGANISM: Artificial sequence
<220> FEATURE:
<223> OTHER INFORMATION: Synthetic construct peptide Aldehyde Ac-LGAY-H

<400> SEQUENCE: 20

```
Leu Glu Gly Leu Tyr Ala Leu Ala Thr Tyr Arg
1               5                   10
```

<210> SEQ ID NO 21
<211> LENGTH: 12
<212> TYPE: PRT
<213> ORGANISM: Artificial sequence
<220> FEATURE:
<223> OTHER INFORMATION: Synthetic Construct - peptide aldehyde
      Ac-FGAY-H

<400> SEQUENCE: 21

```
Pro His Glu Gly Leu Tyr Ala Leu Ala Thr Tyr Arg
1               5                   10
```

<210> SEQ ID NO 22
<211> LENGTH: 12
<212> TYPE: PRT
<213> ORGANISM: Artificial sequence
<220> FEATURE:
<223> OTHER INFORMATION: Synthetic Construct - peptide aldehyde
      Ac-YGAY-H

<400> SEQUENCE: 22

```
Thr Tyr Arg Gly Leu Tyr Ala Leu Ala Thr Tyr Arg
1               5                   10
```

<210> SEQ ID NO 23
<211> LENGTH: 11
<212> TYPE: PRT
<213> ORGANISM: Artificial sequence
<220> FEATURE:
<223> OTHER INFORMATION: Synthetic Construct - peptide aldehyde
      Ac-FGAL-H

```
<400> SEQUENCE: 23

Pro His Glu Gly Leu Tyr Ala Leu Ala Leu Glu
1               5                   10

<210> SEQ ID NO 24
<211> LENGTH: 12
<212> TYPE: PRT
<213> ORGANISM: Artificial sequence
<220> FEATURE:
<223> OTHER INFORMATION: Synthetic Construct - peptide aldehyde
      Ac-FGAF-H

<400> SEQUENCE: 24

Pro His Glu Gly Leu Tyr Ala Leu Ala Pro His Glu
1               5                   10

<210> SEQ ID NO 25
<211> LENGTH: 12
<212> TYPE: PRT
<213> ORGANISM: Artificial sequence
<220> FEATURE:
<223> OTHER INFORMATION: Synthetic Construct - peptide aldehyde
      Ac-FGVY-H

<400> SEQUENCE: 25

Pro His Glu Gly Leu Tyr Val Ala Leu Thr Tyr Arg
1               5                   10

<210> SEQ ID NO 26
<211> LENGTH: 12
<212> TYPE: PRT
<213> ORGANISM: Artificial sequence
<220> FEATURE:
<223> OTHER INFORMATION: Synthetic Construct - peptide aldehyde
      Ac-FGAM-H

<400> SEQUENCE: 26

Pro His Glu Gly Leu Tyr Ala Leu Ala Met Glu Thr
1               5                   10

<210> SEQ ID NO 27
<211> LENGTH: 11
<212> TYPE: PRT
<213> ORGANISM: Artificial sequence
<220> FEATURE:
<223> OTHER INFORMATION: Synthetic Construct - peptide aldehyde
      Ac-WLVY-H

<400> SEQUENCE: 27

Thr Arg Pro Leu Glu Val Ala Leu Thr Tyr Arg
1               5                   10

<210> SEQ ID NO 28
<211> LENGTH: 11
<212> TYPE: PRT
<213> ORGANISM: Artificial sequence
<220> FEATURE:
<223> OTHER INFORMATION: Synthetic Construct - peptide aldehyde
      MeO-CO-FGAL-H

<400> SEQUENCE: 28

Pro His Glu Gly Leu Tyr Ala Leu Ala Leu Glu
1               5                   10

<210> SEQ ID NO 29
<211> LENGTH: 12
<212> TYPE: PRT
```

```
<213> ORGANISM: Artificial sequence
<220> FEATURE:
<223> OTHER INFORMATION: Synthetic Construct - peptide aldehyde
      MeO-CO-FGAF-H

<400> SEQUENCE: 29

Pro His Glu Gly Leu Tyr Ala Leu Ala Pro His Glu
1               5                   10

<210> SEQ ID NO 30
<211> LENGTH: 11
<212> TYPE: PRT
<213> ORGANISM: Artificial sequence
<220> FEATURE:
<223> OTHER INFORMATION: Synthetic Construct - peptide aldehyde
      MeSO2-FGAL-H

<400> SEQUENCE: 30

Pro His Glu Gly Leu Tyr Ala Leu Ala Leu Glu
1               5                   10

<210> SEQ ID NO 31
<211> LENGTH: 11
<212> TYPE: PRT
<213> ORGANISM: Artificial sequence
<220> FEATURE:
<223> OTHER INFORMATION: Synthetic Construct - peptide aldehyde
      EtSO2-FGAL-H

<400> SEQUENCE: 31

Pro His Glu Gly Leu Tyr Ala Leu Ala Leu Glu
1               5                   10

<210> SEQ ID NO 32
<211> LENGTH: 10
<212> TYPE: PRT
<213> ORGANISM: Artificial sequence
<220> FEATURE:
<223> OTHER INFORMATION: Synthetic Construct - peptide aldehyde
      MeO-P(OH)(O)-LGAL-H

<400> SEQUENCE: 32

Leu Glu Gly Leu Tyr Ala Leu Ala Leu Glu
1               5                   10
```